US007838235B2

(12) United States Patent
Caplin

(10) Patent No.: US 7,838,235 B2
(45) Date of Patent: Nov. 23, 2010

(54) SYSTEM AND METHOD FOR HIGH RESOLUTION ANALYSIS OF NUCLEIC ACIDS TO DETECT SEQUENCE VARIATIONS

(75) Inventor: Brian Erich Caplin, Park City, UT (US)

(73) Assignee: Signal Diagnostics, Park City, UT (US)

( * ) Notice: Subject to any disclaimer, the term of this patent is extended or adjusted under 35 U.S.C. 154(b) by 53 days.

(21) Appl. No.: 12/058,637

(22) Filed: Mar. 28, 2008

(65) Prior Publication Data

US 2009/0075269 A1 Mar. 19, 2009

Related U.S. Application Data

(60) Provisional application No. 60/908,604, filed on Mar. 28, 2007.

(51) Int. Cl.
*C12Q 1/68* (2006.01)

(52) U.S. Cl. ......................... 435/6; 435/91.1; 435/91.2; 536/24.33; 536/23.1; 536/22.1

(58) Field of Classification Search ....................... None
See application file for complete search history.

(56) References Cited

U.S. PATENT DOCUMENTS 6,506,568 B2 1/2003 Shriver et al.

FOREIGN PATENT DOCUMENTS

WO WO 00/43545 A2 7/2000

OTHER PUBLICATIONS

Lowe et al. Nucleic Acids Research vol. 18:1757-1761. 1990.*

McCammon et al. Antimicrobial Agents and Chemotherapy vol. 49:2200-2209. 2005.*

PCT International Search Report and Written Opinion, PCT Application No. PCT/US2008/058786, Aug. 29, 2008, 11 pages.

Edwards, K.J. et al., "Detection of *rpoB* Mutations in Mycobacterium Tuberculosis by Biprobe Analysis," Journal of Clinical Microbiology, Sep. 2001, pp. 3350-3352, vol. 39, No. 9.

European Supplementary Search Report, European Application No. 08744694.4, Jul. 26, 2010, 14 pages.

Torres, M.J. et al., "Improved Real-Time PCR for Rapid Detection of Rifampin and Isoniazid Resistance in *Mycobacterium Tuberculosis* Clinical Isolates," Diagnostic Microbiology and Infectious Disease, 2003, pp. 207-212, vol. 45.

* cited by examiner

*Primary Examiner*—Heather G Calamita
(74) *Attorney, Agent, or Firm*—Fenwick & West LLP

(57) ABSTRACT

Provided herein are methods for assaying a biological sample for microorganisms having drug resistant and/or drug sensitive phenotypes, wherein the methods are capable of detecting resistant and sensitive phenotypes associated with known and/or unknown mutations. In some aspects, methods are provided for detecting drug resistant *Myobacterium tuberculosis* (MTb), including multi-drug resistant MTb, wherein drug resistance is associated with one or more novel mutations. Also provided are systems, kits, and compositions related to such methods.

4 Claims, 22 Drawing Sheets

Figure 6A-C
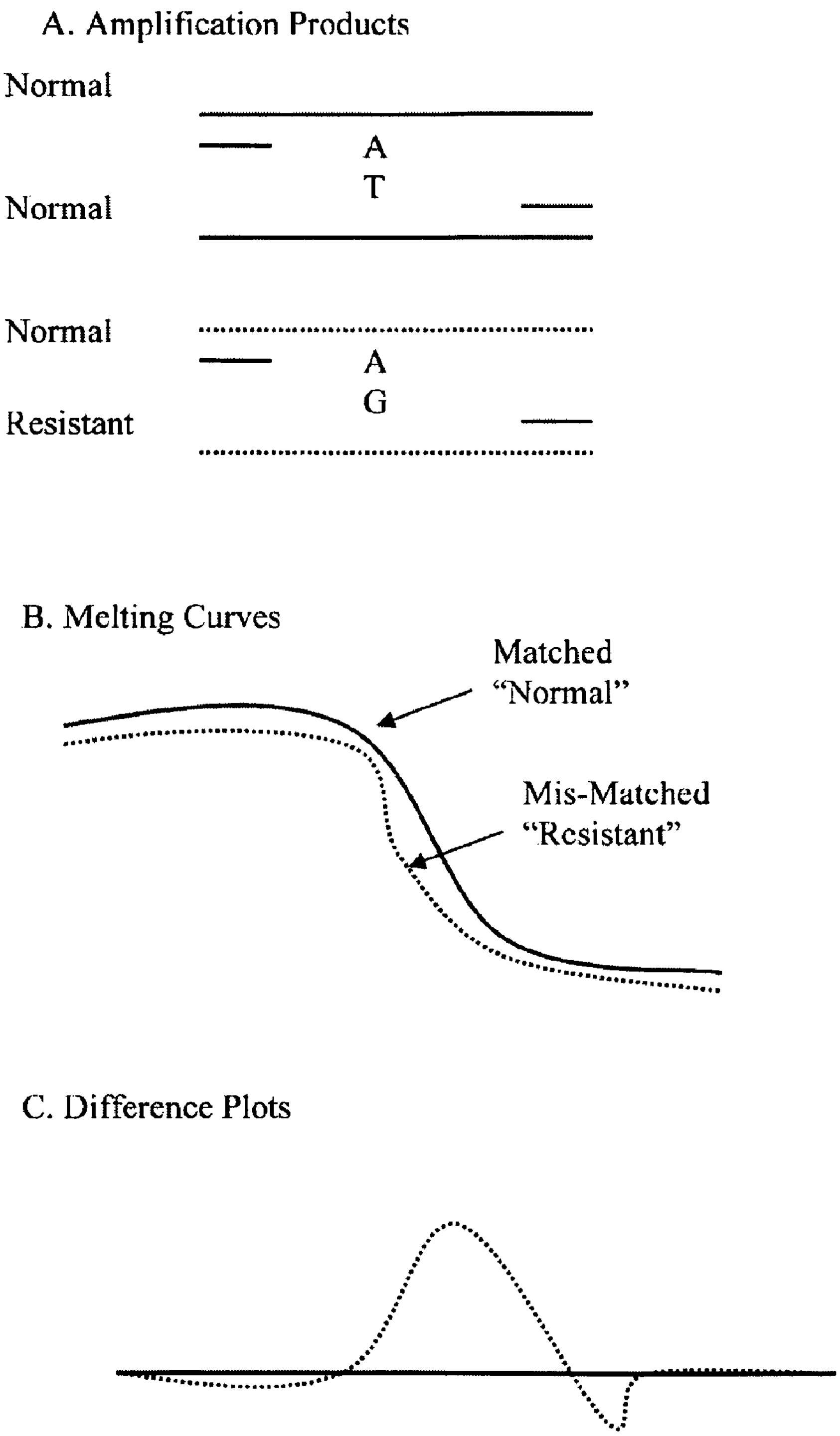

Figure 7
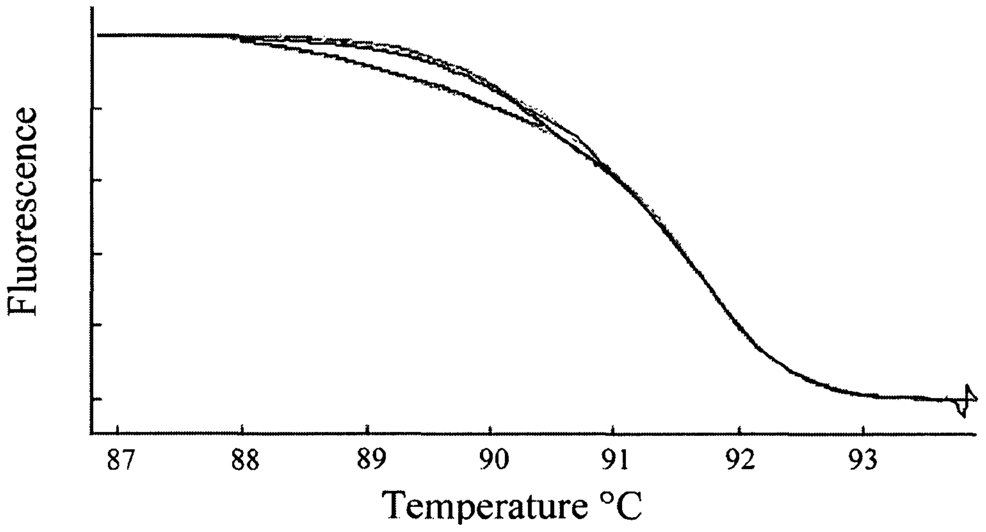
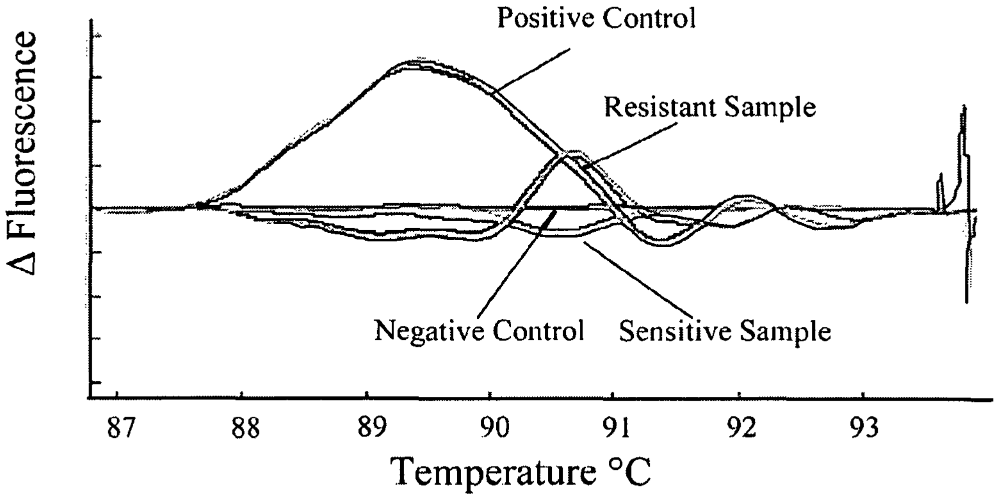

SEQUENCE LISTING

```
<160> NUMBER OF SEQ ID NOS: 215

<210> SEQ ID NO 1
<211> LENGTH: 21
<212> TYPE: DNA
<213> ORGANISM: Human immunodeficiency virus

<400> SEQUENCE: 1

aaggccaatg gacatatcaa a                                               21


<210> SEQ ID NO 2
<211> LENGTH: 17
<212> TYPE: DNA
<213> ORGANISM: Human immunodeficiency virus

<400> SEQUENCE: 2

gggcaccccct cattctt                                                   17


<210> SEQ ID NO 3
<211> LENGTH: 25
<212> TYPE: DNA
<213> ORGANISM: Malaria

<400> SEQUENCE: 3

tatttattta agtgtatgtg taatg                                           25


<210> SEQ ID NO 4
<211> LENGTH: 25
<212> TYPE: DNA
<213> ORGANISM: Malaria

<400> SEQUENCE: 4

caattttgtt taaagttctt ttagc                                           25


<210> SEQ ID NO 5
<211> LENGTH: 16
<212> TYPE: DNA
<213> ORGANISM: Homo Sapiens

<400> SEQUENCE: 5
```

-continued tcccacgtct ccattt 16

<210> SEQ ID NO 6
<211> LENGTH: 16
<212> TYPE: DNA
<213> ORGANISM: Homo Sapiens

<400> SEQUENCE: 6
tgagttccgg cactgt 16

<210> SEQ ID NO 7
<211> LENGTH: 22
<212> TYPE: DNA
<213> ORGANISM: S. cerevisiae

<400> SEQUENCE: 7
ttcaatgcta agaatcctgc tc 22

<210> SEQ ID NO 8
<211> LENGTH: 22
<212> TYPE: DNA
<213> ORGANISM: S. cerevisiae

<400> SEQUENCE: 8
agattggcat atgatcacta cc 22

<210> SEQ ID NO 9
<211> LENGTH: 20
<212> TYPE: DNA
<213> ORGANISM: Staphylococcus aureus

<400> SEQUENCE: 9
aaagctgcaa atattaagga 20

<210> SEQ ID NO 10
<211> LENGTH: 17
<212> TYPE: DNA
<213> ORGANISM: Staphylococcus aureus

<400> SEQUENCE: 10
ggcaatataa cctgcac 17

<210> SEQ ID NO 11
<211> LENGTH: 17
<212> TYPE: DNA
<213> ORGANISM: Mycobacterium tuberculosis

<400> SEQUENCE: 11
gagcgtgtgg tggtcag 17

<210> SEQ ID NO 12
<211> LENGTH: 17
<212> TYPE: DNA
<213> ORGANISM: Mycobacterium tuberculosis

<400> SEQUENCE: 12
cgtcttgtcg gtggact 17

<210> SEQ ID NO 13
<211> LENGTH: 19
<212> TYPE: DNA
<213> ORGANISM: Mycobacterium tuberculosis -continued

<400> SEQUENCE: 13
caaggagttc ttcggcacc 19

<210> SEQ ID NO 14
<211> LENGTH: 17
<212> TYPE: DNA
<213> ORGANISM: Mycobacterium tuberculosis

<400> SEQUENCE: 14
ggacctccag cccggca 17

<210> SEQ ID NO 15
<211> LENGTH: 16
<212> TYPE: DNA
<213> ORGANISM: Mycobacterium tuberculosis

<400> SEQUENCE: 15
ggtggcacag gccaat 16

<210> SEQ ID NO 16
<211> LENGTH: 16
<212> TYPE: DNA
<213> ORGANISM: Mycobacterium tuberculosis

<400> SEQUENCE: 16
gaagcgaccg tccgca 16

<210> SEQ ID NO 17
<211> LENGTH: 15
<212> TYPE: DNA
<213> ORGANISM: Mycobacterium tuberculosis

<400> SEQUENCE: 17
ccgcgcgtgc tggtc 15

<210> SEQ ID NO 18
<211> LENGTH: 19
<212> TYPE: DNA
<213> ORGANISM: Mycobacterium tuberculosis

<400> SEQUENCE: 18
tccatgtagt ccacctcag 19

<210> SEQ ID NO 19
<211> LENGTH: 16
<212> TYPE: DNA
<213> ORGANISM: Mycobacterium tuberculosis

<400> SEQUENCE: 19
cagtcgcccg aacgta 16

<210> SEQ ID NO 20
<211> LENGTH: 15
<212> TYPE: DNA
<213> ORGANISM: Mycobacterium tuberculosis

<400> SEQUENCE: 20
tggtagtccg ccgct 15

<210> SEQ ID NO 21
<211> LENGTH: 18
<212> TYPE: DNA
<213> ORGANISM: Mycobacterium tuberculosis -continued

<400> SEQUENCE: 21
caatcgaggc ggtgttct 18

<210> SEQ ID NO 22
<211> LENGTH: 13
<212> TYPE: DNA
<213> ORGANISM: Mycobacterium tuberculosis

<400> SEQUENCE: 22
cgacgccgcg ttg 13

<210> SEQ ID NO 23
<211> LENGTH: 14
<212> TYPE: DNA
<213> ORGANISM: Mycobacterium tuberculosis

<400> SEQUENCE: 23
gatgcgcacc gcca 14

<210> SEQ ID NO 24
<211> LENGTH: 16
<212> TYPE: DNA
<213> ORGANISM: Mycobacterium tuberculosis

<400> SEQUENCE: 24
gcggtgccat caggag 16

<210> SEQ ID NO 25
<211> LENGTH: 15
<212> TYPE: DNA
<213> ORGANISM: Mycobacterium tuberculosis

<400> SEQUENCE: 25
gcggcggact accat 15

<210> SEQ ID NO 26
<211> LENGTH: 18
<212> TYPE: DNA
<213> ORGANISM: Mycobacterium tuberculosis

<400> SEQUENCE: 26
gattgccgac gtgtccag 18

<210> SEQ ID NO 27
<211> LENGTH: 13
<212> TYPE: DNA
<213> ORGANISM: Mycobacterium tuberculosis

<400> SEQUENCE: 27
gcaacgcggc gtc 13

<210> SEQ ID NO 28
<211> LENGTH: 15
<212> TYPE: DNA
<213> ORGANISM: Mycobacterium tuberculosis

<400> SEQUENCE: 28
ccctggtggc caagc 15

<210> SEQ ID NO 29
<211> LENGTH: 15
<212> TYPE: DNA

-continued

<213> ORGANISM: Mycobacterium tuberculosis

<400> SEQUENCE: 29
gcttggccac caggg 15

<210> SEQ ID NO 30
<211> LENGTH: 15
<212> TYPE: DNA
<213> ORGANISM: Mycobacterium tuberculosis

<400> SEQUENCE: 30
ctggcggtgc gcatc 15

<210> SEQ ID NO 31
<211> LENGTH: 17
<212> TYPE: DNA
<213> ORGANISM: Mycobacterium tuberculosis

<400> SEQUENCE: 31
ccgcgtgtac accacca 17

<210> SEQ ID NO 32
<211> LENGTH: 16
<212> TYPE: DNA
<213> ORGANISM: Mycobacterium tuberculosis

<400> SEQUENCE: 32
agcgcacacc aggcag 16

<210> SEQ ID NO 33
<211> LENGTH: 20
<212> TYPE: DNA
<213> ORGANISM: Mycobacterium tuberculosis

<400> SEQUENCE: 33
ggattgacgg taggtggaga 20

<210> SEQ ID NO 34
<211> LENGTH: 21
<212> TYPE: DNA
<213> ORGANISM: Mycobacterium tuberculosis

<400> SEQUENCE: 34
acgctcgcac cctacgtatt a 21

<210> SEQ ID NO 35
<211> LENGTH: 14
<212> TYPE: DNA
<213> ORGANISM: Mycobacterium tuberculosis

<400> SEQUENCE: 35
cccgcctggg gagt 14

<210> SEQ ID NO 36
<211> LENGTH: 15
<212> TYPE: DNA
<213> ORGANISM: Mycobacterium tuberculosis

<400> SEQUENCE: 36
catgctccgc cgctt 15

<210> SEQ ID NO 37
<211> LENGTH: 20

-continued

<212> TYPE: DNA
<213> ORGANISM: Mycobacterium tuberculosis

<400> SEQUENCE: 37
tagccaaagt cttgactgat 20

<210> SEQ ID NO 38
<211> LENGTH: 16
<212> TYPE: DNA
<213> ORGANISM: Mycobacterium tuberculosis

<400> SEQUENCE: 38
gcgcattcac tgcttc 16

<210> SEQ ID NO 39
<211> LENGTH: 21
<212> TYPE: DNA
<213> ORGANISM: Mycobacterium tuberculosis

<400> SEQUENCE: 39
tgtgatatat cacctttgcc t 21

<210> SEQ ID NO 40
<211> LENGTH: 16
<212> TYPE: DNA
<213> ORGANISM: Mycobacterium tuberculosis

<400> SEQUENCE: 40
cggggaattg atcgcc 16

<210> SEQ ID NO 41
<211> LENGTH: 15
<212> TYPE: DNA
<213> ORGANISM: Mycobacterium tuberculosis

<400> SEQUENCE: 41
accagctcac cgctc 15

<210> SEQ ID NO 42
<211> LENGTH: 20
<212> TYPE: DNA
<213> ORGANISM: Mycobacterium tuberculosis

<400> SEQUENCE: 42
ggtgatagtg gtgaagtagt 20

<210> SEQ ID NO 43
<211> LENGTH: 16
<212> TYPE: DNA
<213> ORGANISM: Mycobacterium tuberculosis

<400> SEQUENCE: 43
gcgttcagca agctca 16

<210> SEQ ID NO 44
<211> LENGTH: 16
<212> TYPE: DNA
<213> ORGANISM: Mycobacterium tuberculosis

<400> SEQUENCE: 44
cgcgaattcg ctgtca 16

<210> SEQ ID NO 45

-continued

```
<211> LENGTH: 15
<212> TYPE: DNA
<213> ORGANISM: Mycobacterium tuberculosis

<400> SEQUENCE: 45

ctgtgcgcat gcaac                                                        15


<210> SEQ ID NO 46
<211> LENGTH: 15
<212> TYPE: DNA
<213> ORGANISM: Mycobacterium tuberculosis

<400> SEQUENCE: 46

tcccggttag gccga                                                        15


<210> SEQ ID NO 47
<211> LENGTH: 20
<212> TYPE: DNA
<213> ORGANISM: Mycobacterium tuberculosis

<400> SEQUENCE: 47

caaacggatt ctggttagcg                                                   20


<210> SEQ ID NO 48
<211> LENGTH: 17
<212> TYPE: DNA
<213> ORGANISM: Mycobacterium tuberculosis

<400> SEQUENCE: 48

ggttgatgcc catcccg                                                      17


<210> SEQ ID NO 49
<211> LENGTH: 17
<212> TYPE: DNA
<213> ORGANISM: Mycobacterium tuberculosis

<400> SEQUENCE: 49

caagtacggt gtgcgtt                                                      17


<210> SEQ ID NO 50
<211> LENGTH: 16
<212> TYPE: DNA
<213> ORGANISM: Mycobacterium tuberculosis

<400> SEQUENCE: 50

gccgacgatc gcactc                                                       16


<210> SEQ ID NO 51
<211> LENGTH: 18
<212> TYPE: DNA
<213> ORGANISM: Mycobacterium tuberculosis

<400> SEQUENCE: 51

gagccgattt cacgaacc                                                     18


<210> SEQ ID NO 52
<211> LENGTH: 17
<212> TYPE: DNA
<213> ORGANISM: Mycobacterium tuberculosis

<400> SEQUENCE: 52

ctcgtttacg cctcaga                                                      17
```

-continued

<210> SEQ ID NO 53
<211> LENGTH: 16
<212> TYPE: DNA
<213> ORGANISM: Mycobacterium tuberculosis

<400> SEQUENCE: 53
tgggccggat ggaatc 16

<210> SEQ ID NO 54
<211> LENGTH: 17
<212> TYPE: DNA
<213> ORGANISM: Mycobacterium tuberculosis

<400> SEQUENCE: 54
gacgacgaac gaaatgt 17

<210> SEQ ID NO 55
<211> LENGTH: 17
<212> TYPE: DNA
<213> ORGANISM: Mycobacterium tuberculosis

<400> SEQUENCE: 55
ctgctgcgca attcgta 17

<210> SEQ ID NO 56
<211> LENGTH: 16
<212> TYPE: DNA
<213> ORGANISM: Mycobacterium tuberculosis

<400> SEQUENCE: 56
gatcccccgg tttcct 16

<210> SEQ ID NO 57
<211> LENGTH: 15
<212> TYPE: DNA
<213> ORGANISM: Mycobacterium tuberculosis

<400> SEQUENCE: 57
gccgacagac catcc 15

<210> SEQ ID NO 58
<211> LENGTH: 16
<212> TYPE: DNA
<213> ORGANISM: Mycobacterium tuberculosis

<400> SEQUENCE: 58
gtcgtagccg tgatga 16

<210> SEQ ID NO 59
<211> LENGTH: 18
<212> TYPE: DNA
<213> ORGANISM: Mycobacterium tuberculosis

<400> SEQUENCE: 59
tccgacgatc cgttctac 18

<210> SEQ ID NO 60
<211> LENGTH: 17
<212> TYPE: DNA
<213> ORGANISM: Mycobacterium tuberculosis

<400> SEQUENCE: 60
gagcgcaaca ccgttcc 17

-continued

<210> SEQ ID NO 61
<211> LENGTH: 17
<212> TYPE: DNA
<213> ORGANISM: Mycobacterium tuberculosis

<400> SEQUENCE: 61
gacttcctcg acgaacc 17

<210> SEQ ID NO 62
<211> LENGTH: 18
<212> TYPE: DNA
<213> ORGANISM: Mycobacterium tuberculosis

<400> SEQUENCE: 62
gcctgcacga tcaatacc 18

<210> SEQ ID NO 63
<211> LENGTH: 19
<212> TYPE: DNA
<213> ORGANISM: Mycobacterium tuberculosis

<400> SEQUENCE: 63
ttcaacccga tgacctacg 19

<210> SEQ ID NO 64
<211> LENGTH: 17
<212> TYPE: DNA
<213> ORGANISM: Mycobacterium tuberculosis

<400> SEQUENCE: 64
ggtgatcacc ttggccg 17

<210> SEQ ID NO 65
<211> LENGTH: 17
<212> TYPE: DNA
<213> ORGANISM: Mycobacterium tuberculosis

<400> SEQUENCE: 65
tggggtctat gtcctga 17

<210> SEQ ID NO 66
<211> LENGTH: 19
<212> TYPE: DNA
<213> ORGANISM: Mycobacterium tuberculosis

<400> SEQUENCE: 66
gcagtacctt cagattgag 19

<210> SEQ ID NO 67
<211> LENGTH: 19
<212> TYPE: DNA
<213> ORGANISM: Mycobacterium tuberculosis

<400> SEQUENCE: 67
ggctcaatct gaaggtact 19

<210> SEQ ID NO 68
<211> LENGTH: 15
<212> TYPE: DNA
<213> ORGANISM: Mycobacterium tuberculosis

<400> SEQUENCE: 68
gggccagctg ttaag 15

-continued

<210> SEQ ID NO 69
<211> LENGTH: 15
<212> TYPE: DNA
<213> ORGANISM: Mycobacterium tuberculosis

<400> SEQUENCE: 69
ttcgcgccgc ttaac 15

<210> SEQ ID NO 70
<211> LENGTH: 16
<212> TYPE: DNA
<213> ORGANISM: Mycobacterium tuberculosis

<400> SEQUENCE: 70
ggttccggtg ccatac 16

<210> SEQ ID NO 71
<211> LENGTH: 16
<212> TYPE: DNA
<213> ORGANISM: Mycobacterium tuberculosis

<400> SEQUENCE: 71
gtatggcacc ggaacc 16

<210> SEQ ID NO 72
<211> LENGTH: 17
<212> TYPE: DNA
<213> ORGANISM: Mycobacterium tuberculosis

<400> SEQUENCE: 72
tccttggcgg tgtattg 17

<210> SEQ ID NO 73
<211> LENGTH: 15
<212> TYPE: DNA
<213> ORGANISM: Mycobacterium tuberculosis

<400> SEQUENCE: 73
cgctccccga cgatg 15

<210> SEQ ID NO 74
<211> LENGTH: 16
<212> TYPE: DNA
<213> ORGANISM: Mycobacterium tuberculosis

<400> SEQUENCE: 74
gacttgtggc tgcagg 16

<210> SEQ ID NO 75
<211> LENGTH: 15
<212> TYPE: DNA
<213> ORGANISM: Mycobacterium tuberculosis

<400> SEQUENCE: 75
cctgcagcca caagt 15

<210> SEQ ID NO 76
<211> LENGTH: 16
<212> TYPE: DNA
<213> ORGANISM: Mycobacterium tuberculosis

<400> SEQUENCE: 76

-continued gcaggttcgc cttgtc 16

<210> SEQ ID NO 77
<211> LENGTH: 15
<212> TYPE: DNA
<213> ORGANISM: Mycobacterium tuberculosis

<400> SEQUENCE: 77
cggccgagta catgc 15

<210> SEQ ID NO 78
<211> LENGTH: 16
<212> TYPE: DNA
<213> ORGANISM: Mycobacterium tuberculosis

<400> SEQUENCE: 78
ggctcccagg tgatac 16

<210> SEQ ID NO 79
<211> LENGTH: 15
<212> TYPE: DNA
<213> ORGANISM: Mycobacterium tuberculosis

<400> SEQUENCE: 79
ggcaaggatg gcagt 15

<210> SEQ ID NO 80
<211> LENGTH: 15
<212> TYPE: DNA
<213> ORGANISM: Mycobacterium tuberculosis

<400> SEQUENCE: 80
gcacgtcgaa cctgt 15

<210> SEQ ID NO 81
<211> LENGTH: 15
<212> TYPE: DNA
<213> ORGANISM: Mycobacterium tuberculosis

<400> SEQUENCE: 81
ggcgggcatg tttct 15

<210> SEQ ID NO 82
<211> LENGTH: 15
<212> TYPE: DNA
<213> ORGANISM: Mycobacterium tuberculosis

<400> SEQUENCE: 82
ggcgatgatc ggctc 15

<210> SEQ ID NO 83
<211> LENGTH: 17
<212> TYPE: DNA
<213> ORGANISM: Mycobacterium tuberculosis

<400> SEQUENCE: 83
ggcgatgatt tcccagt 17

<210> SEQ ID NO 84
<211> LENGTH: 16
<212> TYPE: DNA
<213> ORGANISM: Mycobacterium tuberculosis

<400> SEQUENCE: 84

-continued gccaaagcct gtaggt 16

<210> SEQ ID NO 85
<211> LENGTH: 15
<212> TYPE: DNA
<213> ORGANISM: Mycobacterium tuberculosis

<400> SEQUENCE: 85
tcggcgacaa cctcc 15

<210> SEQ ID NO 86
<211> LENGTH: 16
<212> TYPE: DNA
<213> ORGANISM: Mycobacterium tuberculosis

<400> SEQUENCE: 86
gccccggata ccagag 16

<210> SEQ ID NO 87
<211> LENGTH: 18
<212> TYPE: DNA
<213> ORGANISM: Mycobacterium tuberculosis

<400> SEQUENCE: 87
actcggttta tcacgacg 18

<210> SEQ ID NO 88
<211> LENGTH: 16
<212> TYPE: DNA
<213> ORGANISM: Mycobacterium tuberculosis

<400> SEQUENCE: 88
ccatggctac caggac 16

<210> SEQ ID NO 89
<211> LENGTH: 18
<212> TYPE: DNA
<213> ORGANISM: Mycobacterium tuberculosis

<400> SEQUENCE: 89
gtatacatcg gtgcttgc 18

<210> SEQ ID NO 90
<211> LENGTH: 16
<212> TYPE: DNA
<213> ORGANISM: Mycobacterium tuberculosis

<400> SEQUENCE: 90
gcaccagcgg tgaaca 16

<210> SEQ ID NO 91
<211> LENGTH: 15
<212> TYPE: DNA
<213> ORGANISM: Mycobacterium tuberculosis

<400> SEQUENCE: 91
gcgaccgatg gactg 15

<210> SEQ ID NO 92
<211> LENGTH: 16
<212> TYPE: DNA
<213> ORGANISM: Mycobacterium tuberculosis -continued

<400> SEQUENCE: 92
ccaccacggt gatcag 16

<210> SEQ ID NO 93
<211> LENGTH: 15
<212> TYPE: DNA
<213> ORGANISM: Mycobacterium tuberculosis

<400> SEQUENCE: 93
cgccatcacc gactc 15

<210> SEQ ID NO 94
<211> LENGTH: 15
<212> TYPE: DNA
<213> ORGANISM: Mycobacterium tuberculosis

<400> SEQUENCE: 94
ttgcggtccg atgtc 15

<210> SEQ ID NO 95
<211> LENGTH: 16
<212> TYPE: DNA
<213> ORGANISM: Mycobacterium tuberculosis

<400> SEQUENCE: 95
ttcggcttcc tgctct 16

<210> SEQ ID NO 96
<211> LENGTH: 15
<212> TYPE: DNA
<213> ORGANISM: Mycobacterium tuberculosis

<400> SEQUENCE: 96
ggtttgctgg cctcc 15

<210> SEQ ID NO 97
<211> LENGTH: 15
<212> TYPE: DNA
<213> ORGANISM: Mycobacterium tuberculosis

<400> SEQUENCE: 97
tcaacaacgg cctgc 15

<210> SEQ ID NO 98
<211> LENGTH: 16
<212> TYPE: DNA
<213> ORGANISM: Mycobacterium tuberculosis

<400> SEQUENCE: 98
atggaccgct cgatca 16

<210> SEQ ID NO 99
<211> LENGTH: 16
<212> TYPE: DNA
<213> ORGANISM: Mycobacterium tuberculosis

<400> SEQUENCE: 99
caccgtcatc ctgacc 16

<210> SEQ ID NO 100
<211> LENGTH: 15
<212> TYPE: DNA
<213> ORGANISM: Mycobacterium tuberculosis -continued

<400> SEQUENCE: 100
ttttggcgcg aaccc 15

<210> SEQ ID NO 101
<211> LENGTH: 15
<212> TYPE: DNA
<213> ORGANISM: Mycobacterium tuberculosis

<400> SEQUENCE: 101
ggctggtcca acgtg 15

<210> SEQ ID NO 102
<211> LENGTH: 18
<212> TYPE: DNA
<213> ORGANISM: Mycobacterium tuberculosis

<400> SEQUENCE: 102
gcattggtat caggctcg 18

<210> SEQ ID NO 103
<211> LENGTH: 15
<212> TYPE: DNA
<213> ORGANISM: Mycobacterium tuberculosis

<400> SEQUENCE: 103
ttcgcccgag caaag 15

<210> SEQ ID NO 104
<211> LENGTH: 15
<212> TYPE: DNA
<213> ORGANISM: Mycobacterium tuberculosis

<400> SEQUENCE: 104
ccgttagtgc cgtct 15

<210> SEQ ID NO 105
<211> LENGTH: 15
<212> TYPE: DNA
<213> ORGANISM: Mycobacterium tuberculosis

<400> SEQUENCE: 105
atgtcacgct gcaac 15

<210> SEQ ID NO 106
<211> LENGTH: 18
<212> TYPE: DNA
<213> ORGANISM: Mycobacterium tuberculosis

<400> SEQUENCE: 106
gatcctccgt cttctcca 18

<210> SEQ ID NO 107
<211> LENGTH: 16
<212> TYPE: DNA
<213> ORGANISM: Mycobacterium tuberculosis

<400> SEQUENCE: 107
cgcgaactga accaga 16

<210> SEQ ID NO 108
<211> LENGTH: 15
<212> TYPE: DNA

-continued

<213> ORGANISM: Mycobacterium tuberculosis

<400> SEQUENCE: 108
gcggtatgcg cctta 15

<210> SEQ ID NO 109
<211> LENGTH: 16
<212> TYPE: DNA
<213> ORGANISM: Mycobacterium tuberculosis

<400> SEQUENCE: 109
gagcaggtgc tttccc 16

<210> SEQ ID NO 110
<211> LENGTH: 15
<212> TYPE: DNA
<213> ORGANISM: Mycobacterium tuberculosis

<400> SEQUENCE: 110
ctctgttgcc gaacg 15

<210> SEQ ID NO 111
<211> LENGTH: 15
<212> TYPE: DNA
<213> ORGANISM: Mycobacterium tuberculosis

<400> SEQUENCE: 111
gggttcctat ggcgg 15

<210> SEQ ID NO 112
<211> LENGTH: 18
<212> TYPE: DNA
<213> ORGANISM: Mycobacterium tuberculosis

<400> SEQUENCE: 112
ggttgaacaa cccaagtc 18

<210> SEQ ID NO 113
<211> LENGTH: 18
<212> TYPE: DNA
<213> ORGANISM: Mycobacterium tuberculosis

<400> SEQUENCE: 113
cgatcccgat aggtgttt 18

<210> SEQ ID NO 114
<211> LENGTH: 17
<212> TYPE: DNA
<213> ORGANISM: Mycobacterium tuberculosis

<400> SEQUENCE: 114
ggcacccaga ttcagac 17

<210> SEQ ID NO 115
<211> LENGTH: 17
<212> TYPE: DNA
<213> ORGANISM: Mycobacterium tuberculosis

<400> SEQUENCE: 115
atcacaggag tggagtt 17

<210> SEQ ID NO 116
<211> LENGTH: 16

-continued

<212> TYPE: DNA
<213> ORGANISM: Mycobacterium tuberculosis

<400> SEQUENCE: 116
aagatgttgc gcgaat 16

<210> SEQ ID NO 117
<211> LENGTH: 17
<212> TYPE: DNA
<213> ORGANISM: Mycobacterium tuberculosis

<400> SEQUENCE: 117
tacgaaccac acgttgc 17

<210> SEQ ID NO 118
<211> LENGTH: 16
<212> TYPE: DNA
<213> ORGANISM: Mycobacterium tuberculosis

<400> SEQUENCE: 118
gttggctacc cgacag 16

<210> SEQ ID NO 119
<211> LENGTH: 15
<212> TYPE: DNA
<213> ORGANISM: Mycobacterium tuberculosis

<400> SEQUENCE: 119
gcttgacgcc gctac 15

<210> SEQ ID NO 120
<211> LENGTH: 18
<212> TYPE: DNA
<213> ORGANISM: Mycobacterium tuberculosis

<400> SEQUENCE: 120
gaagttgagt tcgcaggt 18

<210> SEQ ID NO 121
<211> LENGTH: 15
<212> TYPE: DNA
<213> ORGANISM: Mycobacterium tuberculosis

<400> SEQUENCE: 121
cagccgatgc cgctg 15

<210> SEQ ID NO 122
<211> LENGTH: 17
<212> TYPE: DNA
<213> ORGANISM: Mycobacterium tuberculosis

<400> SEQUENCE: 122
cgccgatgcg gtaagaa 17

<210> SEQ ID NO 123
<211> LENGTH: 15
<212> TYPE: DNA
<213> ORGANISM: Mycobacterium tuberculosis

<400> SEQUENCE: 123
acagcgccaa cgtca 15

<210> SEQ ID NO 124

-continued

<211> LENGTH: 16
<212> TYPE: DNA
<213> ORGANISM: Mycobacterium tuberculosis

<400> SEQUENCE: 124
gacgatcgga ggtcgt 16

<210> SEQ ID NO 125
<211> LENGTH: 15
<212> TYPE: DNA
<213> ORGANISM: Mycobacterium tuberculosis

<400> SEQUENCE: 125
tcgccgctag gctga 15

<210> SEQ ID NO 126
<211> LENGTH: 15
<212> TYPE: DNA
<213> ORGANISM: Mycobacterium tuberculosis

<400> SEQUENCE: 126
atctgctggc cgaac 15

<210> SEQ ID NO 127
<211> LENGTH: 15
<212> TYPE: DNA
<213> ORGANISM: Mycobacterium tuberculosis

<400> SEQUENCE: 127
cgggtacgcc caaat 15

<210> SEQ ID NO 128
<211> LENGTH: 16
<212> TYPE: DNA
<213> ORGANISM: Mycobacterium tuberculosis

<400> SEQUENCE: 128
ccagatggtg actccg 16

<210> SEQ ID NO 129
<211> LENGTH: 18
<212> TYPE: DNA
<213> ORGANISM: Mycobacterium tuberculosis

<400> SEQUENCE: 129
attccaatat cggttggc 18

<210> SEQ ID NO 130
<211> LENGTH: 16
<212> TYPE: DNA
<213> ORGANISM: Mycobacterium tuberculosis

<400> SEQUENCE: 130
ccacgatcgc cattgt 16

<210> SEQ ID NO 131
<211> LENGTH: 16
<212> TYPE: DNA
<213> ORGANISM: Mycobacterium tuberculosis

<400> SEQUENCE: 131
ggtgagcaca tcgacc 16

-continued

<210> SEQ ID NO 132
<211> LENGTH: 17
<212> TYPE: DNA
<213> ORGANISM: Mycobacterium tuberculosis

<400> SEQUENCE: 132
atagctggcg atgttga 17

<210> SEQ ID NO 133
<211> LENGTH: 15
<212> TYPE: DNA
<213> ORGANISM: Mycobacterium tuberculosis

<400> SEQUENCE: 133
cgccgacctg tttct 15

<210> SEQ ID NO 134
<211> LENGTH: 18
<212> TYPE: DNA
<213> ORGANISM: Mycobacterium tuberculosis

<400> SEQUENCE: 134
cggctagaag tagtttcg 18

<210> SEQ ID NO 135
<211> LENGTH: 16
<212> TYPE: DNA
<213> ORGANISM: Mycobacterium tuberculosis

<400> SEQUENCE: 135
gcaactacca cccgca 16

<210> SEQ ID NO 136
<211> LENGTH: 15
<212> TYPE: DNA
<213> ORGANISM: Mycobacterium tuberculosis

<400> SEQUENCE: 136
gtagcgcagc gacca 15

<210> SEQ ID NO 137
<211> LENGTH: 81
<212> TYPE: DNA
<213> ORGANISM: Human immunodeficiency virus

<400> SEQUENCE: 137
aaggccaatg gacatatcaa atttatcaag agccatttaa aaatctgaaa acaggaaaat 60
atgcaagaat gaggggtgcc c 81

<210> SEQ ID NO 138
<211> LENGTH: 62
<212> TYPE: DNA
<213> ORGANISM: Malaria

<400> SEQUENCE: 138
tatttattta agtgtatgtg taatgaataa aatttttgct aaaagaactt taaacaaaat 60
tg 62

<210> SEQ ID NO 139
<211> LENGTH: 90
<212> TYPE: DNA
<213> ORGANISM: Homo sapiens -continued

<400> SEQUENCE: 139
tcccacgtct ccatttcttt atgcctggct ttgcccctct caccagccgt ggaagccagc 60
agtatcgagc tctcacagtg ccggaactca 90

<210> SEQ ID NO 140
<211> LENGTH: 67
<212> TYPE: DNA
<213> ORGANISM: S. cerevisiae

<400> SEQUENCE: 140
ttcaatgcta agaatcctgc tcctatgcac ggtcacgtta ttcttggtag tgatcatatg 60
ccaatct 67

<210> SEQ ID NO 141
<211> LENGTH: 74
<212> TYPE: DNA
<213> ORGANISM: Staphylococcus aureus

<400> SEQUENCE: 141
aaagctgcaa atattaagga aaataatacc attgttgtta gacacatttt aggtaaagtg 60
caggttatat tgcc 74

<210> SEQ ID NO 142
<211> LENGTH: 81
<212> TYPE: DNA
<213> ORGANISM: Mycobacterium tuberculosis

<400> SEQUENCE: 142
gagcgtgtgg tggtcagcca gctggtgcgg tcgcccgggg tgtacttcga cgagaccatt 60
gacaagtcca ccgacaagac g 81

<210> SEQ ID NO 143
<211> LENGTH: 137
<212> TYPE: DNA
<213> ORGANISM: Mycobacterium tuberculosis

<400> SEQUENCE: 143
caaggagttc ttcggcacca gccagctgag ccaattcatg gaccagaaca acccgctgtc 60
ggggttgacc cacaagcgcc gactgtcggc gctggggccc ggcggtctgt cacgtgagcg 120
tgccgggctg gaggtcc 137

<210> SEQ ID NO 144
<211> LENGTH: 43
<212> TYPE: DNA
<213> ORGANISM: Mycobacterium tuberculosis

<400> SEQUENCE: 144
ggtggcacag gccaattcgc cgatcgatgc ggacggtcgc ttc 43

<210> SEQ ID NO 145
<211> LENGTH: 71
<212> TYPE: DNA
<213> ORGANISM: Mycobacterium tuberculosis

<400> SEQUENCE: 145
ccgcgcgtgc tggtccgccg caaggcgggc gaggtggagt acgtgccctc gtctgaggtg 60
gactacatgg a 71

-continued

<210> SEQ ID NO 146
<211> LENGTH: 151
<212> TYPE: DNA
<213> ORGANISM: Mycobacterium tuberculosis

<400> SEQUENCE: 146
cagtcgcccg aacgtatggt ggacgtatgc gggcgttgat catcgtcgac gtgcagaacg 60
acttctgcga gggtggctcg ctggcggtaa ccggtggcgc cgcgctggcc cgcgccatca 120
gcgactacct ggccgaagcg gcggactacc a 151

<210> SEQ ID NO 147
<211> LENGTH: 111
<212> TYPE: DNA
<213> ORGANISM: Mycobacterium tuberculosis

<400> SEQUENCE: 147
caatcgaggc ggtgttctac aagggtgcct acaccggagc gtacagcggc ttcgaaggag 60
tcgacgagaa cggcacgcca ctgctgaatt ggctgcggca acgcggcgtc g 111

<210> SEQ ID NO 148
<211> LENGTH: 49
<212> TYPE: DNA
<213> ORGANISM: Mycobacterium tuberculosis

<400> SEQUENCE: 148
gatgcgcacc gccagcgtcg agttggtttg cagctcctga tggcaccgc 49

<210> SEQ ID NO 149
<211> LENGTH: 159
<212> TYPE: DNA
<213> ORGANISM: Mycobacterium tuberculosis

<400> SEQUENCE: 149
gcggcggact accatcacgt cgtggcaacc aaggacttcc acatcgaccc gggtgaccac 60
ttctccggca caccggacta ttcctcgtcg tggccaccgc attgcgtcag cggtactccc 120
ggcgcggact tccatcccag tctggacacg tcggcaatc 159

<210> SEQ ID NO 150
<211> LENGTH: 101
<212> TYPE: DNA
<213> ORGANISM: Mycobacterium tuberculosis

<400> SEQUENCE: 150
gcaacgcggc gtcgatgagg tcgatgtggt cggtattgcc accgatcatt gtgtgcgcca 60
gacggccgag gacgcggtac gcaatggctt ggccaccagg g 101

<210> SEQ ID NO 151
<211> LENGTH: 88
<212> TYPE: DNA
<213> ORGANISM: Mycobacterium tuberculosis

<400> SEQUENCE: 151
gcttggccac cagggtgctg gtggacctga cagcgggtgt gtcggccgat accaccgtcg 60
ccgcgctgga ggagatgcgc accgccag 88

<210> SEQ ID NO 152
<211> LENGTH: 179
<212> TYPE: DNA
<213> ORGANISM: Mycobacterium tuberculosis -continued

<400> SEQUENCE: 152
ccgcgtgtac accaccactc cgaagaagcc gaactcggcg cttcggaagg ttgcccgcgt 60
gaagttgacg agtcaggtcg aggtcacggc gtacattccc ggcgagggcc acaacctgca 120
ggagcactcg atggtgctgg tgcgcggcgg ccgggtgaag gacctgcctg gtgtgcgct 179

<210> SEQ ID NO 153
<211> LENGTH: 76
<212> TYPE: DNA
<213> ORGANISM: Mycobacterium tuberculosis

<400> SEQUENCE: 153
ggattgacgg taggtggaga agaagcaccg gccaactacg tgccagcagc cgcggtaata 60
cgtagggtgc gagcgt 76

<210> SEQ ID NO 154
<211> LENGTH: 74
<212> TYPE: DNA
<213> ORGANISM: Mycobacterium tuberculosis

<400> SEQUENCE: 154
cccgcctggg gagtacggcc gcaaggctaa aactcaaagg aattgacggg ggcccgcaca 60
agcggcggag catg 74

<210> SEQ ID NO 155
<211> LENGTH: 142
<212> TYPE: DNA
<213> ORGANISM: Mycobacterium tuberculosis

<400> SEQUENCE: 155
tagccaaagt cttgactgat tccagaaaag ggagtcatat tgtctagtgt gtcctctata 60
ccggactacg ccgaacagct ccggacggcc gacctgcgcg tgacccgacc gcgcgtcgcc 120
gtcctggaag cagtgaatgc gc 142

<210> SEQ ID NO 156
<211> LENGTH: 125
<212> TYPE: DNA
<213> ORGANISM: Mycobacterium tuberculosis

<400> SEQUENCE: 156
tgtgatatat cacctttgcc tgacagcgac ttcacggcac gatggaatgt cgcaaccaaa 60
tgcattgtcc gctttgatga tgaggagagt catgccactg ctaaccattg gcgatcaatt 120
ccccg 125

<210> SEQ ID NO 157
<211> LENGTH: 80
<212> TYPE: DNA
<213> ORGANISM: Mycobacterium tuberculosis

<400> SEQUENCE: 157
accagctcac cgctctcatc ggcggtgacc tgtccaaggt cgacgccaag cagcccggcg 60
actacttcac cactatcacc 80

<210> SEQ ID NO 158
<211> LENGTH: 78
<212> TYPE: DNA
<213> ORGANISM: Mycobacterium tuberculosis

<400> SEQUENCE: 158

-continued gcgttcagca agctcaatga cgagttcgag gaccgcgacg cccagatcct gggggtttcg 60
attgacagcg aattcgcg 78

<210> SEQ ID NO 159
<211> LENGTH: 78
<212> TYPE: DNA
<213> ORGANISM: Mycobacterium tuberculosis

<400> SEQUENCE: 159
ctgtgcgcat gcaactggcg caagggcgac ccgacgctag acgctggcga actcctcaag 60
gcttcggcct aaccggga 78

<210> SEQ ID NO 160
<211> LENGTH: 299
<212> TYPE: DNA
<213> ORGANISM: Mycobacterium tuberculosis

<400> SEQUENCE: 160
caaacggatt ctggttagcg gaatcatcac cgactcgtcg atcgcgtttc acatcgcacg 60
ggtagcccag gagcagggcg cccagctggt gctcaccggg ttcgaccggc tgcggctgat 120
tcagcgcatc accgaccggc tgccggcaaa ggccccgctg ctcgaactcg acgtgcaaaa 180
cgaggagcac ctggccagct tggccggccg ggtgaccgag gcgatcgggg cgggcaacaa 240
gctcgacggg gtggtgcatt cgattgggtt catgccgcag accgggatgg gcatcaacc 299

<210> SEQ ID NO 161
<211> LENGTH: 120
<212> TYPE: DNA
<213> ORGANISM: Mycobacterium tuberculosis

<400> SEQUENCE: 161
aagtacggtg tgcgttcgaa tctcgttgcc gcaggcccta tccggacgct ggcgatgagt 60
gcgatcgtcg gcggtgcgct cggcgaggag gccggcgccc agatccagct gctcgaggag 120

<210> SEQ ID NO 162
<211> LENGTH: 80
<212> TYPE: DNA
<213> ORGANISM: Mycobacterium tuberculosis

<400> SEQUENCE: 162
gagccgattt cacgaaccgg tggggacgtt catggtcccc gccggtttgt gcgcataccg 60
tgatctgagg cgtaaacgag 80

<210> SEQ ID NO 163
<211> LENGTH: 260
<212> TYPE: DNA
<213> ORGANISM: Mycobacterium tuberculosis

<400> SEQUENCE: 163
tgggccggat ggaatcgaaa ccgctgcgcc ggggccataa aatgattatc ggcatgcggg 60
gttcctatgg cggcgtggtc atgattggca tgctgtcgtc ggtggtcgga cttgggttgt 120
tcaacccgct atcggtgggg gccgggttga tcctcggccg gatggcatat aaagaggaca 180
aacaaaaccg gttgctgcgg gtgcgcagcg aggccaaggc caatgtgcgg cgcttcgtcg 240
acgacatttc gttcgtcgtc 260

<210> SEQ ID NO 164

-continued

<211> LENGTH: 292
<212> TYPE: DNA
<213> ORGANISM: Mycobacterium tuberculosis

<400> SEQUENCE: 164
ctgctgcgca attcgtaggg cgtcaataca cccgcagcca gggcctcgct gcccagaaag 60
ggatccgtca tggtcgaagt gtgctgagtc acaccgacaa acgtcacgag cgtaacccca 120
gtgcgaaagt tcccgccgga aatcgcagcc acgttacgct cgtggacata ccgatttcgg 180
cccggccgcg gcgagacgat aggttgtcgg ggtgactgcc acagccactg aaggggccaa 240
acccccattc gtatcccgtt cagtcctggt taccggagga aaccggggga tc 292

<210> SEQ ID NO 165
<211> LENGTH: 79
<212> TYPE: DNA
<213> ORGANISM: Mycobacterium tuberculosis

<400> SEQUENCE: 165
gccgacagac catccggctg tctggaacca cccggtcgtt gacccacata ccgtcgagcc 60
cgatcatcac ggctacgac 79

<210> SEQ ID NO 166
<211> LENGTH: 68
<212> TYPE: DNA
<213> ORGANISM: Mycobacterium tuberculosis

<400> SEQUENCE: 166
tccgacgatc cgttctactt cccacctgcc ggctaccagc atgccgtgcc cggaacggtg 60
ttgcgctc 68

<210> SEQ ID NO 167
<211> LENGTH: 116
<212> TYPE: DNA
<213> ORGANISM: Mycobacterium tuberculosis

<400> SEQUENCE: 167
gacttcctcg acgaacccct tgaggacatt ctgtcgacgc cggaaatttc ccatgtcttc 60
ggcgacacca agctgggtag cgcggtgccc accccgccgg tattgatcgt gcaggc 116

<210> SEQ ID NO 168
<211> LENGTH: 63
<212> TYPE: DNA
<213> ORGANISM: Mycobacterium tuberculosis

<400> SEQUENCE: 168
ttcaacccga tgacctacgc cggcatggcg agactggccg tgatcgcggc caaggtgatc 60
acc 63

<210> SEQ ID NO 169
<211> LENGTH: 296
<212> TYPE: DNA
<213> ORGANISM: Mycobacterium tuberculosis

<400> SEQUENCE: 169
tggggtctat gtcctgattg ttcgatatcc gacacttcgc gatcacatcc gtgatcacag 60
cccgataaca ccaactcctg gaaggaatgc tgtgcccgag caacacccac ccattacaga 120
aaccaccacc ggagccgcta gcaacggctg tcccgtcgtg ggtcatatga aataccccgt 180
cgagggcggc ggaaaccagg actggtggcc caaccggctc aaagtatact ttatggggca 240

-continued gctcccgccg cctttggtcc tgaccaccgg gttggccgag tttctgaagg tactgc 296

<210> SEQ ID NO 170
<211> LENGTH: 284
<212> TYPE: DNA
<213> ORGANISM: Mycobacterium tuberculosis

<400> SEQUENCE: 170
ggctcaatct gaaggtactg caccaaaacc cggccgtcgc tgacccgatg ggtgcggcgt 60
tcgactatgc cgcggaggtc gcgaccatcg acgttgacgc cctgacgcgg gacatcgagg 120
aagtgatgac cacctcgcag ccgtggtggc ccgccgacta cggccactac gggccgctgt 180
ttatccggat ggcgtggcac gctgccggca cctaccgcat ccacgacggc cgcggcggcg 240
ccgggggcgg catgcagcgg ttcgcgccgc ttaacagctg gccc 284

<210> SEQ ID NO 171
<211> LENGTH: 660
<212> TYPE: DNA
<213> ORGANISM: Mycobacterium tuberculosis

<400> SEQUENCE: 171
ttcgcgccgc ttaacagctg gcccgacaac gccagcttgg acaaggcgcg ccggctgctg 60
tggccggtca agaagaagta cggcaagaag ctctcatggg cggacctgat tgttttcgcc 120
ggcaactgcg cgctggaatc gatgggcttc aagacgttcg ggttcggctt cggccgggtc 180
gaccagtggg agcccgatga ggtctattgg ggcaaggaag ccacctggct cggcgatgag 240
cgttacagcg gtaagcggga tctggagaac ccgctggccg cggtgcagat ggggctgatc 300
tacgtgaacc cggaggggcc gaacggcaac ccggacccca tggccgcggc ggtcgacatt 360
cgcgagacgt ttcggcgcat ggccatgaac gacgtcgaaa cagcggcccg ccagctgtaa 420
gcgctctgca aagccgcgta ccggtacttg ctgcagcttt gtcgccggct gatcgtcggc 480
ggtcacactt tcggtaagac ccatggcgcc ggcccggccg atctggtcgg ccccgaaccc 540
gaggctgctc cgctggagca gatgggcttg ggctggaaga gctcgtagcc ggggcttggg 600
ctccgacgag gcgacctcgt ctacccgaac ccgaccttct cgagcattgg caccggaacc 660

<210> SEQ ID NO 172
<211> LENGTH: 162
<212> TYPE: DNA
<213> ORGANISM: Mycobacterium tuberculosis

<400> SEQUENCE: 172
gtatggcacc ggaaccggta aggacgcgat caccagcggc atcgaggtcg tatggacgaa 60
caccccgacg aaatgggaca acagtttcct cgagatcctg tacggctacg agtgggagct 120
gacgaagagc cctgctggcg cttggcaata caccgccaag ga 162

<210> SEQ ID NO 173
<211> LENGTH: 393
<212> TYPE: DNA
<213> ORGANISM: Mycobacterium tuberculosis

<400> SEQUENCE: 173
cgctccccga cgatgctggc cactgacctc tcgctgcggg tggatccgat ctatgagcgg 60
atcacgcgtc gctggctgga acaccccgag gaattggccg acgagttcgc caaggcctgg 120
tacaagctga tccaccgaga catgggtccc gttgcgagat accttgggcc gctggtcccc 180

```
aagcagaccc tgctgtggca ggatccggtc cctgcggtca gccacgacct cgtcggcgaa    240

gccgagattg ccagccttaa gagccagatc cgggcatcgg gattgactgt ctcacagcta    300

gtttcgaccg catgggcggc ggcgtcgtcg ttccgtggta gcgacaagcg cggcggcgcc    360

aacggtggtc gcatccgcct gcagccacaa gtc                                 393

<210> SEQ ID NO 174
<211> LENGTH: 356
<212> TYPE: DNA
<213> ORGANISM: Mycobacterium tuberculosis

<400> SEQUENCE: 174

cctgcagcca caagtcgggt gggaggtcaa cgaccccgac ggggatctgc gcaaggtcat     60

tcgcaccctg gaagagatcc aggagtcatt caactccgcg gcgccgggga acatcaaagt    120

gtccttcgcc gacctcgtcg tgctcggtgg ctgtgccgcc atagagaaag cagcaaaggc    180

ggctggccac aacatcacgg tgcccttcac cccgggccgc acggatgcgt cgcaggaaca    240

aaccgacgtg gaatcctttg ccgtgctgga gcccaaggca gatggcttcc gaaactacct    300

cggaaagggc aacccgttgc cggccgagta catgctgctc gacaaggcga acctgc        356

<210> SEQ ID NO 175
<211> LENGTH: 196
<212> TYPE: DNA
<213> ORGANISM: Mycobacterium tuberculosis

<400> SEQUENCE: 175

cggccgagta catgctgctc gacaaggcga acctgcttac gctcagtgcc cctgagatga     60

cggtgctggt aggtggcctg cgcgtcctcg gcgcaaacta caagcgctta ccgctgggcg    120

tgttcaccga ggcctccgag tcactgacca acgacttctt cgtgaacctg ctcgacatgg    180

gtatcacctg ggagcc                                                    196

<210> SEQ ID NO 176
<211> LENGTH: 181
<212> TYPE: DNA
<213> ORGANISM: Mycobacterium tuberculosis

<400> SEQUENCE: 176

ggcaaggatg gcagtggcaa ggtgaagtgg accggcagcc gcgtggacct ggtcttcggg     60

tccaactcgg agttgcgggc gcttgtcgag gtctatggcg ccgatgacgc gcagccgaag    120

ttcgtgcagg acttcgtcgc tgcctgggac aaggtgatga acctcgacag gttcgacgtg    180

c                                                                    181

<210> SEQ ID NO 177
<211> LENGTH: 67
<212> TYPE: DNA
<213> ORGANISM: Mycobacterium tuberculosis

<400> SEQUENCE: 177

ggcgggcatg tttctggctg tctggctgcc gctggacaac ggccttcggc ccgagccgat     60

catcgcc                                                              67

<210> SEQ ID NO 178
<211> LENGTH: 59
<212> TYPE: DNA
<213> ORGANISM: Mycobacterium tuberculosis

<400> SEQUENCE: 178
```

-continued ggcgatgatt tcccagtacc cggcgtggtc ggttggccgg tctaacctac aggctttgg 59

<210> SEQ ID NO 179
<211> LENGTH: 263
<212> TYPE: DNA
<213> ORGANISM: Mycobacterium tuberculosis

<400> SEQUENCE: 179
tcggcgacaa cctccgcggc cccgcatcct caccgccctt aaccgcgtcg cctaccatcg 60
agcctcgtgc cccacgacgg taatgagcga tctcaccgga tcgcacgcct agcagccgtc 120
gtctcgggaa tcgcgggtct gctgctgtgc ggcatcgttc cgctgcttcc ggtgaaccaa 180
accaccgcga ccatcttctg gccgcagggc agcaccgccg acggcaacat cacccagatc 240
accgcccctc tggtatccgg ggc 263

<210> SEQ ID NO 180
<211> LENGTH: 79
<212> TYPE: DNA
<213> ORGANISM: Mycobacterium tuberculosis

<400> SEQUENCE: 180
actcggttta tcacgacgcc cggcgcgctc aagaaggccg tgatgctcct cggcgtgctg 60
gcggtcctgg tagccatgg 79

<210> SEQ ID NO 181
<211> LENGTH: 180
<212> TYPE: DNA
<213> ORGANISM: Mycobacterium tuberculosis

<400> SEQUENCE: 181
gtatacatcg gtgcttgccc agctggcggc ggtgagcacc gccggcgtct ggatgcgcct 60
gcccgccacc ctggccggaa tcgcctgctg gctgatcgtc agccgtttcg tgctgcggcg 120
gctgggaccg ggcccgggcg ggctggcgtc caaccgggtc gctgtgttca ccgctggtgc 180

<210> SEQ ID NO 182
<211> LENGTH: 67
<212> TYPE: DNA
<213> ORGANISM: Mycobacterium tuberculosis

<400> SEQUENCE: 182
gcgaccgatg gactgctggc gccgctggcg gtgctggccg cggcgttgtc gctgatcacc 60
gtggtgg 67

<210> SEQ ID NO 183
<211> LENGTH: 346
<212> TYPE: DNA
<213> ORGANISM: Mycobacterium tuberculosis

<400> SEQUENCE: 183
cgccatcacc gactccgcgg gcaccgccgg agggaagggc ccggtcggga tcaacgggtc 60
gcacgcggcg ctgccgttcg gattggaccc ggcacgtacc ccggtgatgg gcagctacgg 120
ggagaacaac ctggccgcca cggccacctc ggcctggtac cagttaccgc cccgcagccc 180
ggaccggccg ctggtggtgg tttccgcggc cggcgccatc tggtcctaca aggaggacgg 240
cgatttcatc tacggccagt ccctgaaact gcagtggggc gtcaccggcc cggacggccg 300
catccagcca ctggggcagg tatttccgat cgacatcgga ccgcaa 346

-continued

<210> SEQ ID NO 184
<211> LENGTH: 293
<212> TYPE: DNA
<213> ORGANISM: Mycobacterium tuberculosis

<400> SEQUENCE: 184
ttcggcttcc tgctctggca tgtcatcggc gcgaattcgt cggacgacgg ctacatcctg 60
ggcatggccc gagtcgccga ccacgccggc tacatgtcca actatttccg ctggttcggc 120
agcccggagg atcccttcgg ctggtattac aacctgctgg cgctgatgac ccatgtcagc 180
gacgccagtc tgtggatgcg cctgccagac ctggccgccg ggctagtgtg ctggctgctg 240
ctgtcgcgtg aggtgctgcc ccgcctcggg ccggcggtgg aggccagcaa acc 293

<210> SEQ ID NO 185
<211> LENGTH: 76
<212> TYPE: DNA
<213> ORGANISM: Mycobacterium tuberculosis

<400> SEQUENCE: 185
tcaacaacgg cctgcggccg gagggcatca tcgcgctcgg ctcgctggtc acctatgtgc 60
tgatcgagcg gtccat 76

<210> SEQ ID NO 186
<211> LENGTH: 77
<212> TYPE: DNA
<213> ORGANISM: Mycobacterium tuberculosis

<400> SEQUENCE: 186
caccgtcatc ctgaccgtgg tgttcgccga ccagaccctg tcaacggtgt tggaagccac 60
cagggttcgc gccaaaa 77

<210> SEQ ID NO 187
<211> LENGTH: 77
<212> TYPE: DNA
<213> ORGANISM: Mycobacterium tuberculosis

<400> SEQUENCE: 187
ggctggtcca acgtgcgggc gtttgtcggc ggctgcggac tggccgacga cgtactcgtc 60
gagcctgata ccaatgc 77

<210> SEQ ID NO 188
<211> LENGTH: 302
<212> TYPE: DNA
<213> ORGANISM: Mycobacterium tuberculosis

<400> SEQUENCE: 188
ttcgcccgag caaagatgcc cgccgatgcc gtcgcggtcc gggtggtggc cgaggatctg 60
tcgctgacac cggaggactg gatcgcggtg accccgccgc gggtaccgga cctgcgctca 120
ctgcaggaat atgtgggctc gacgcagccg gtgctgctgg actgggcggt cggtttggcc 180
ttcccgtgcc agcagccgat gctgcacgcc aatggcatcg ccgaaatccc gaagttccgc 240
atcacaccgg actactcggc taagaagctg gacaccgaca cgtgggaaga cggcactaac 300
gg 302

<210> SEQ ID NO 189
<211> LENGTH: 105
<212> TYPE: DNA
<213> ORGANISM: Mycobacterium tuberculosis

<400> SEQUENCE: 189
atgtcacgct gcaactggtg cgggtgggcg acccgcgggc attcggctgc gtacccaccg 60
acgaggagga ccgcgtagtc gcctttctgg agaagacgga ggatc 105

<210> SEQ ID NO 190
<211> LENGTH: 392
<212> TYPE: DNA
<213> ORGANISM: Mycobacterium tuberculosis

<400> SEQUENCE: 190
cgcgaactga accagatggg catttgccag gcggtggtgc cggtatccgg acttcttgcg 60
ctgaccgcgc gcacactgcg ccagaccgag ttcatcgcgc tgcgcaagct ggccggtgcc 120
gagcgcaccg agctcaatag ggccctgctg agcgtggacc gttttgtgcg ccgggacagt 180
ccgctaccgg tggacgcggg catccgtgcg caattgctcg agcggttcgg catgttcggc 240
atccggatgt cgattgccgt gctggcggcc ggcgtgaccg attcgaccgg gctggccgcc 300
gaactgctgg agcgcagcgg gctggtggcg ctgcgcaatg tgatagacca gcagttcgcg 360
cagcgctccg acatgcttaa ggcgcatacc gc 392

<210> SEQ ID NO 191
<211> LENGTH: 72
<212> TYPE: DNA
<213> ORGANISM: Mycobacterium tuberculosis

<400> SEQUENCE: 191
gagcaggtgc tttcccgcgc gacggagcga gtgcgtgctg gggtactcgg cgaaatacgt 60
tcggcaacag ag 72

<210> SEQ ID NO 192
<211> LENGTH: 68
<212> TYPE: DNA
<213> ORGANISM: Mycobacterium tuberculosis

<400> SEQUENCE: 192
gggttcctat ggcggcgtgg tcatgattgg catgctgtcg tcggtggtcg gacttgggtt 60
gttcaacc 68

<210> SEQ ID NO 193
<211> LENGTH: 300
<212> TYPE: DNA
<213> ORGANISM: Mycobacterium tuberculosis

<400> SEQUENCE: 193
cgatcccgat aggtgtttgg ccggcttgcg gatcagaccc cgatttcggg gtgaggcgga 60
atccatagcg tcgatggcac agcgccggtc acgccggcga acagcttctt cgattgaagg 120
gaaatgaaga tgacctcgct tatcgattac atcctgagcc tgttccgcag cgaagacgcc 180
gcccggtcgt tcgttgccgc tccgggacgg gccatgacca gtgccgggct gatcgatatc 240
gcgccgcacc aaatctcatc ggtggcggcc aatgtggtgc cgggtctgaa tctgggtgcc 300

<210> SEQ ID NO 194
<211> LENGTH: 292
<212> TYPE: DNA
<213> ORGANISM: Mycobacterium tuberculosis

<400> SEQUENCE: 194

-continued

```
atcacaggag tggagttttg aacgcaacga cggcaggtgc tgtgcaattc aacgtcttag     60

gaccactgga actaaacctc cggggcacca aactgccatt gggaacgccg aaacaacgtg    120

ccgtgctcgc catgctgttg ctatcccgga accaagtcgt agcggccgac gcactggtcc    180

aggcaatctg ggagaagtcg ccacctgcac gagcccgacg caccgtccac acgtacattt    240

gcaaccttcg ccggaccctg agcgatgcag gcgttgattc gcgcaacatc tt            292


<210> SEQ ID NO 195
<211> LENGTH: 68
<212> TYPE: DNA
<213> ORGANISM: Mycobacterium tuberculosis

<400> SEQUENCE: 195

tacgaaccac acgttgcgca gacatcacac tagactactt gtgtaacggc gccctgtcgg     60

gtagccaa                                                              68


<210> SEQ ID NO 196
<211> LENGTH: 70
<212> TYPE: DNA
<213> ORGANISM: Mycobacterium tuberculosis

<400> SEQUENCE: 196

gcttgacgcc gctacggcac tggcgcagcg cactggccac ggcgctggca gcacctgcga     60

actcaacttc                                                            70


<210> SEQ ID NO 197
<211> LENGTH: 80
<212> TYPE: DNA
<213> ORGANISM: Mycobacterium tuberculosis

<400> SEQUENCE: 197

cagccgatgc cgctgtcaag ggccaccgac ccggtacatc gcacggcgtg ccgagatcct     60

gggttcttac cgcatcggcg                                                 80


<210> SEQ ID NO 198
<211> LENGTH: 79
<212> TYPE: DNA
<213> ORGANISM: Mycobacterium tuberculosis

<400> SEQUENCE: 198

acagcgccaa cgtcagccgc caccacgccg tcatcgtcga cacgggcacc aactacgtca     60

tcaacgacct ccgatcgtc                                                  79


<210> SEQ ID NO 199
<211> LENGTH: 129
<212> TYPE: DNA
<213> ORGANISM: Mycobacterium tuberculosis

<400> SEQUENCE: 199

tcgccgctag gctgaccgcg tgtcaatcgt gacgccatac gaggacctgc tgcgcttcgt     60

gctcgaaacg ggtacgccca aatccgaccg caccggcacc ggaacccgca gcctgttcgg    120

ccagcagat                                                            129


<210> SEQ ID NO 200
<211> LENGTH: 200
<212> TYPE: DNA
<213> ORGANISM: Mycobacterium tuberculosis

<400> SEQUENCE: 200
```

-continued cgggtacgcc caaatccgac cgcaccggca ccggaacccg cagcctgttc ggccagcaga 60
tgcgctatga tttgtcggcc ggtttcccgc tgctcactac caagaaagtc catttcaaat 120
cggtagccta cgagctgctg tggtttttgc gcggcgattc caatatcggt tggctgcacg 180
agcacggagt caccatctgg 200

<210> SEQ ID NO 201
<211> LENGTH: 107
<212> TYPE: DNA
<213> ORGANISM: Mycobacterium tuberculosis

<400> SEQUENCE: 201
attccaatat cggttggctg cacgagcacg gagtcaccat ctgggacgaa tgggcaagtg 60
atacaggcga actcgggccg atctacggtg tacaatggcg atcgtgg 107

<210> SEQ ID NO 202
<211> LENGTH: 228
<212> TYPE: DNA
<213> ORGANISM: Mycobacterium tuberculosis

<400> SEQUENCE: 202
ggtgagcaca tcgaccagat cagcgcggcg ctggatttgc tgcgcaccga tcccgattcc 60
cggcgcatca tcgtgtcggc ctggaacgtc ggcgaaatcg agcggatggc gctgccgccc 120
tgtcatgcgt tcttccagtt ctacgtcgcc gatggccggc tgagctgtca gctctaccaa 180
cgcagcgccg acctgtttct gggtgtgccg ttcaacatcg ccagctat 228

<210> SEQ ID NO 203
<211> LENGTH: 200
<212> TYPE: DNA
<213> ORGANISM: Mycobacterium tuberculosis

<400> SEQUENCE: 203
cgccgacctg tttctgggtg tgccgttcaa catcgccagc tatgcgttgc tcacccacat 60
gatggccgcc caggccggct tgtcggtcgg cgagttcatc tggaccggtg gcgactgcca 120
catctacgac aatcacgtcg agcaagtacg gctgcagctc agccgcgagc cgcggccata 180
tccgaaacta cttctagccg 200

<210> SEQ ID NO 204
<211> LENGTH: 77
<212> TYPE: DNA
<213> ORGANISM: Mycobacterium tuberculosis

<400> SEQUENCE: 204
gcaactacca cccgcacggc gacgcgtcga tctacgacag cctggtgcgc atggcccagc 60
cctggtcgct gcgctac 77

<210> SEQ ID NO 205
<211> LENGTH: 25
<212> TYPE: DNA
<213> ORGANISM: Mycobacterium tuberculosis

<400> SEQUENCE: 205
ccggaaacgt cggcatcgca aactc 25

<210> SEQ ID NO 206
<211> LENGTH: 28
<212> TYPE: DNA

-continued

<213> ORGANISM: Mycobacterium tuberculosis

<400> SEQUENCE: 206
tgcccgtgtt gtagaagccc gtgttgaa 28

<210> SEQ ID NO 207
<211> LENGTH: 17
<212> TYPE: DNA
<213> ORGANISM: Mycobacterium tuberculosis

<400> SEQUENCE: 207
tcgttcatca ccgatcc 17

<210> SEQ ID NO 208
<211> LENGTH: 17
<212> TYPE: DNA
<213> ORGANISM: Mycobacterium tuberculosis

<400> SEQUENCE: 208
gtgagcagtt cgttcca 17

<210> SEQ ID NO 209
<211> LENGTH: 19
<212> TYPE: DNA
<213> ORGANISM: Mycobacterium tuberculosis

<400> SEQUENCE: 209
tcaacgagac gggcacgct 19

<210> SEQ ID NO 210
<211> LENGTH: 16
<212> TYPE: DNA
<213> ORGANISM: Mycobacterium tuberculosis

<400> SEQUENCE: 210
tgcgagcgta ggcgtc 16

<210> SEQ ID NO 211
<211> LENGTH: 15
<212> TYPE: DNA
<213> ORGANISM: Mycobacterium tuberculosis

<400> SEQUENCE: 211
gtccagcgcc gcttc 15

<210> SEQ ID NO 212
<211> LENGTH: 23
<212> TYPE: DNA
<213> ORGANISM: Mycobacterium tuberculosis

<400> SEQUENCE: 212
ctgctaccca cagccggtta ggt 23

<210> SEQ ID NO 213
<211> LENGTH: 15
<212> TYPE: DNA
<213> ORGANISM: Mycobacterium tuberculosis

<400> SEQUENCE: 213
gccagcattg aggat 15

<210> SEQ ID NO 214
<211> LENGTH: 18

-continued

```
<212> TYPE: DNA
<213> ORGANISM: Mycobacterium tuberculosis

<400> SEQUENCE: 214

caattcgggc accaataa                                                     18


<210> SEQ ID NO 215
<211> LENGTH: 19
<212> TYPE: DNA
<213> ORGANISM: Mycobacterium tuberculosis

<400> SEQUENCE: 215

tgcgatgccg acgtttccg                                                    19
```

SYSTEM AND METHOD FOR HIGH RESOLUTION ANALYSIS OF NUCLEIC ACIDS TO DETECT SEQUENCE VARIATIONS

CROSS REFERENCE TO RELATED APPLICATIONS

This application claims benefit under 35 U.S.C. §119(e) to U.S. Provisional Application No. 60/908,604 filed Mar. 28, 2007, hereby incorporated by reference in its entirety.

FIELD

The present invention relates generally to systems and methods for preparing and analyzing biological samples to detect nucleic acid sequence variations associated with phenotypes of interest. In certain embodiments, methods and systems are provided for amplifying nucleic acids of microorganisms from a biological sample, and detecting sequence variations associated with drug resistance and/or sensitivity.

BACKGROUND

Very few developments in the history of science have had such a profound impact upon human life as advances in controlling pathogenic microorganisms. It was not until the late $19^{th}$ and early $20^{th}$ centuries that the work of Pasteur and Koch established microorganisms as the cause of infectious diseases and provided strategies that led to rational prevention and control strategies. The sulphonamides were among the first groups of compounds discovered to suppress microorganism infections, and though little was known about their mechanism of action, the discovery stimulated a massive hunt for more effective antibiotic compounds. The isolation of an impure but highly active preparation of penicillin by Florey and Chain in 1940, and the subsequent success of penicillin diverted additional scientific effort towards the search for antibiotics, leading to the discovery of approximately 3,000 named antibiotics. However, despite rapid progress in the discovery of new compounds, only 50 of the named antibiotics have met with clinical use, and even fewer are commonly used in treating microorganism diseases.

The initial effectiveness of antibiotics against microorganism infections has been partly offset by the emergence of strains of microorganisms that are resistant to various antibiotics. Antibiotic resistance has proven difficult to overcome because of the accelerated evolutionary adaptability of microorganisms, the increasing overuse of antibiotics in the clinic, and lack of patient compliance in completing prescribed dosing regimens. Resistance issues have made many otherwise curable diseases, such as gonorrhea and typhoid, difficult to treat. In addition, microorganisms resistant to vancomycin, one of the last broadly effective antibiotics, are becoming increasingly prevalent in hospitals.

New antibiotic compounds are constantly being developed to keep infectious microorganisms at bay, and an understanding of the mechanisms of antibiotic resistance has proven valuable in the development process. Advances in genomics allow researchers to identify biochemical pathways that are susceptible to inhibition or modification, and to rationally design drugs targeted against such pathways. Many drugs exert a therapeutic effect by binding to a microorganism protein and modifying its structure and/or function. In such cases, microorganisms can develop immunity by physical modification of the target protein in a manner that interferes with drug binding or activity. For example, resistance to the antibiotic erythromycin in several microorganisms results from a variation of the 50S ribosome subunit that causes a reduced affinity of ribosomes for erythromycin. Since a protein's structure/function is determined by its primary sequence, which is in turn determined by the sequence of the nucleic acid encoding the protein, nucleic acid sequence variations associated with drug resistant phenotypes are useful diagnostic indicators of drug resistance.

While methods have been established to identify nucleic acid sequence variations in microorganisms, existing techniques are limited by the requirement for foreknowledge of the particular mutations or other variations being used as diagnostic indicators. As a result, known screening procedures often overlook newly developed and/or uncharacterized sequence variations associated with drug resistance or other characteristics of interest.

Accordingly, there is a need in the art for fast, affordable, and reliable methods for detecting both known and unknown nucleic acid sequence variations having diagnostic utility, including mutations associated with drug sensitivity and/or drug resistance patterns in a wide variety of organisms, such as yeasts, viruses, fungi, bacteria, parasites and even humans.

SUMMARY

In some aspects, methods are provided for determining the responsiveness of a microorganism to a drug, the methods comprising obtaining a biological sample from a patient, the sample containing an infectious microorganism; amplifying one or more segments of DNA of the microorganism, the one or more segments including at least one polymorphism associated with responsiveness of the microorganism to a drug of interest; and assaying the one or more amplified DNA segments for sequence variations relative to a reference sequence, wherein a variation in one or more of the amplified DNA segments indicates responsiveness of the microorganism to the drug.

In some preferred embodiments, amplified DNA is assayed for sequence variations using high resolution melting curve analysis. In various embodiments, melting curve analysis involves incubating the amplified DNA (target DNA) with a complementary reference sequence, such as a wild-type sequence, in the presence of a DNA-binding fluorescent dye that emits a substantially different level of fluorescence in the presence of double-stranded DNA (dsDNA) relative to single-stranded DNA (ssDNA). In some preferred embodiments, the DNA-binding dye is dsDNA-specific dye, such as SYBR Green I or SYBR Green II, and melting curve analysis involves monitoring the level of fluorescence as a function of time as the assay solution is slowly heated at a constant rate. Advantageously, melting curve analysis according to methods provided herein can accurately detect single base pair mismatches between a target DNA sequence and a reference sequence, and/or mismatches in two, three, four, five, or more bases.

In some embodiments, the reference sequence used in melting curve analyses of methods provided herein includes at least one polymorphism associated with drug responsiveness, such as drug resistance or drug sensitivity, and the analysis detects one or more additional polymorphisms in the DNA segment that includes the polymorphism associated with drug responsiveness.

In some aspects, methods are provided for determining if a patient is amenable to treatment with a drug, the methods comprising obtaining a biological sample from a patient, where the sample contains *Myobacterium tuberculosis* (MTb); amplifying one or more segments of MTb DNA of SEQ ID NOS: 142-204, each of the one or more segments including at least one polymorphism associated with sensitivity of the MTb to an antibiotic drug; and assaying the one or more amplified DNA segments for sequence variations relative to the corresponding sequence among SEQ ID NOS: 142-204, wherein a variation in one or more of the amplified DNA segments indicates sensitivity of MTb to the antibiotic drug. In some embodiments, variations in two or more of the amplified DNA segments indicates sensitivity of MTb to the antibiotic drug.

In some embodiments, the MTb DNA of SEQ ID NOS: 142-204 is amplified by PCR using the corresponding primers of SEQ ID NOS: 11-136.

In various embodiments, amplified MTb DNA comprises one or more of SEQ ID NOS: 142-145, and a variation in one or more of the amplified DNA segments indicates sensitivity of MTb to rifampicin; the amplified MTb DNA comprises one or more of SEQ ID NOS: 146-151, and a variation in one or more of the amplified DNA segments indicates sensitivity of MTb to pyrazinamide; the amplified MTb DNA comprises one or more of SEQ ID NOS: 152-154, and a variation in one or more of the amplified DNA segments indicates sensitivity of MTb to streptomycin; the amplified MTb DNA comprises one or more of SEQ ID NOS: 155-176, and a variation in one or more of the amplified DNA segments indicates sensitivity of MTb to isoniazid; the amplified MTb DNA comprises one or more of SEQ ID NOS: 177-198, and a variation in one or more of the amplified DNA segments indicates sensitivity of MTb to ethambutol; the amplified MTb DNA comprises one or more of SEQ ID NOS: 199-203, and a variation in one or more of the amplified DNA segments indicates sensitivity of MTb to one or both of capreomycin and viomycin; and/or the amplified MTb DNA comprises SEQ ID NO: 204; and a variation in the amplified DNA segment indicates sensitivity of MTb to one or more of oxifloxacin, moxifloxican, gatifloxican, sitafloxacin, ofloxacin, levofloxacin, and sparfloxacin.

In an additional aspect, kits are provided for determining whether a patient is amenable to treatment with a drug, where the kits comprise at least one primer pair of SEQ ID NOS: 1-136; at least one nucleotide probe complementary to an amplicon of SEQ ID NOS: 137-204; and instructions for using the at least one primer pair to amplify DNA from a biological sample of a patient infected with *Myobacterium tuberculosis* (MTb), and using the at least one nucleotide probe to detect sequence variations within the amplified DNA using high resolution melting curve analysis.

BRIEF DESCRIPTION OF THE DRAWINGS

FIG. 6: Graphical representations of the amplification products from a Rifampicin resistance screen. A—Homoduplex and heteroduplex amplification products. B—Melting curves of the homo- and heteroduplex products. C—Difference plot between the melting curves in B.

FIG. 7: Graphical representation of the curve analysis and difference curves of control and sensitive samples.

DETAILED DESCRIPTION OF ILLUSTRATIVE ASPECTS

Figure 1:
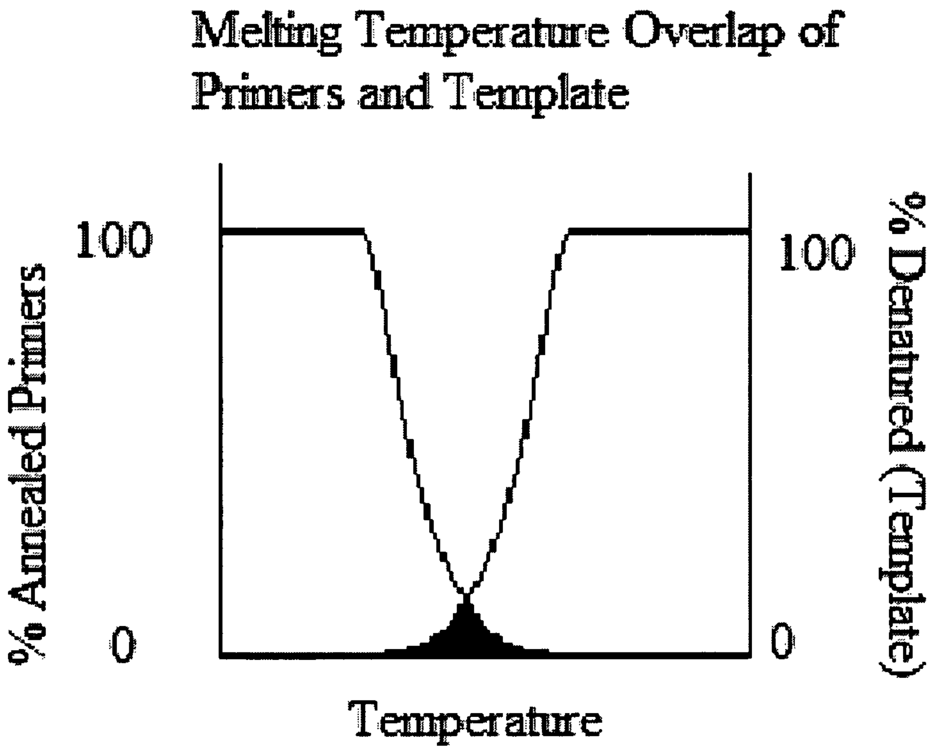
FIG. 1: A graphical representation of a design for overlapping primer annealing temperatures and template denaturation temperatures.

Provided herein are reliable, low-cost methods for detecting nucleic acid sequence variations associated with one or more phenotypic characteristics having diagnostic utility in the treatment of a disease, disorder, or condition. In some aspects, methods described herein are useful for detecting nucleic acid sequence variations associated with the responsiveness of a microorganism to one or more drugs. Also provided herein are compositions, systems, and kits related to the instant methods. While a number of aspects and advantages of the instant invention are described herein with respect to various methods, skilled artisans will recognize that such aspects and advantages are also applicable to related compositions, systems, kits, and the like.

The term "microorganism" as used herein can refer to bacteria, fungi, protozoa, parasites and/or viruses. In various preferred embodiments, the microorganism is a bacterial pathogen. In some preferred embodiments, the microorganism is *Mycobacterium tuberculosis*. However, while a number of aspects and advantages of the instant invention are described herein in relation to *Mycobacterium tuberculosis*, skilled artisans will recognize that such aspects and advantages are also applicable for other microorganisms, and for a variety of diseases and conditions. Non-limiting examples of microorganisms useful in the diagnostic methods provided herein are set forth in Table I, along with variable sequence elements related to the drug responsiveness of such microorganisms.

The "subject" referred to herein can be any organism capable of hosting a microorganism, including but not limited to, experimental animals (e.g., mice, rats, rabbits, and the like) and humans. In various preferred embodiments, the subject is a human patient suffering from an infectious disease. In some preferred embodiments, the patient suffers from tuberculosis.

A "biological sample" described herein can include any biological material taken from a subject, including but not limited to, expectorations (e.g., sputum), blood, blood cells (e.g., lymphocytes), tissue, biopsies, cultured cells, pleural, peritoneal, or cerebrospinal fluid, sweat, feces, and urine. In some embodiments, a biological sample from a subject is treated, e.g., to culture an infectious microorganism and/or amplify its genetic material, before being assayed according to methods provided herein.

As used herein, the term "drug" can refer to any compound, agent, treatment modality, or combination thereof. In some preferred aspects, the drug is an antibiotic compound.

The term "target nucleic acid(s)" as used herein refers to nucleic acids derived from an infectious microorganism, as distinguished from nucleic acids of the subject and/or foreign nucleic acids unrelated to the disease, disorder, or condition intended for treatment. In some aspects, a target nucleic acid is a nucleic acid of a microorganism that is assayed according to a method provided herein.

The term "reference nucleic acid" as used herein refers to a nucleic acid corresponding to a target nucleic acid (e.g., representing the same portion of genomic DNA), that differs from the target nucleic acid by one or more sequence variations. For example, in some aspects, a reference nucleic acid has the sequence of a wild-type microorganism (e.g., with respect to responsiveness to a drug of interest). In further aspects, a reference nucleic acid has the sequence of a wild-type human cell, such as a diseased cell, including, e.g., a human cancer cell.

The term "sequence variation" as used herein in relation to nucleic acids refers to a difference in the sequence of a nucleic acid relative to the sequence of a corresponding nucleic acid (e.g., a sequence representing the same gene or other portion of genomic DNA). In some preferred embodiments, sequence variations detected according to various methods provided herein are "Single Nucleotide Polymorphisms" ("SNPs"), resulting from a difference in the identity of a single nucleotide between a target nucleic acid and a reference nucleic acid. In further embodiments, sequence variations detected according to various methods provided herein include "Multiple Nucleotide Polymorphisms" ("MNPs") In some embodiments, the reference nucleic acid corresponds to a non-drug resistant phenotype and a drug resistant phenotype is detected according to a method provided herein by identifying a sequence variation between the reference nucleic acid and a target nucleic acid of a biological sample from a subject infected with the microorganism or diseased cell, such as a drug resistant cancer cell.

The terms "responsiveness" and "drug responsiveness" as used herein can refer to resistance, sensitivity, susceptibility, tolerance and/or other phenotypic characteristics of a microorganism or diseased cell, such as a cancer cell, related to the therapeutic effect of a drug, including non-responsiveness. Drug responsiveness can be assessed directly, according to the effect of the drug on a targeted microorganism or diseased cell, such as a cancer cell (e.g., a bacterial mortality or a cellular mortality), and/or indirectly, according to the effect of the drug on one or more aspects of an infectious disease caused by the microorganism (e.g., prevention, amelioration, alleviation, and/or elimination of the disease or one or more symptoms of the disease). In some preferred aspects, systems and methods are provided herein for detecting resistance to one or more drugs, where resistance refers to inheritable (genetic) resistance.

The term "variable sequence element" refers to a region of a nucleic acid (e.g., DNA or RNA) comprised of a string of adjacent nucleotides—for example, 2, 3, 5, 10, 15, 25, 50, 75, 100 or more consecutive bases—that includes at least one sequence variation known to be associated with a phenotypic characteristic of interest, such as resistance, sensitivity, and/or other aspects of drug responsiveness. Without being bound by a particular theory, it is believed that sequence variations associated with drug responsiveness, such as drug resistance and/or sensitivity, are likely to occur in regions of the nucleic acid that are important in determining the responsive phenotype, such that a variable sequence element that includes the variation (and surrounding nucleotides) is substantially more likely to contain additional, uncharacterized variations associated with the responsive (e.g., resistant or sensitive) phenotype. For example, a sequence variation associated with drug resistance will often occur in a region of a nucleic acid that encodes a site of the corresponding protein that is a structural and/or functional determinant of drug responsiveness, such as a drug binding site. A variable sequence element including the known variation (and surrounding nucleotides) will likely encode structurally and/or functionally related portions of the protein (e.g., a pocket, fold, or other structure that comprises the drug binding site), and additional, uncharacterized variations within the variable sequence element will likely be associated with the same phenotype as the known variation.

Methods are thus provided herein for assaying drug responsive phenotypes associated with known and/or unknown sequence variations. Advantageously, such methods are capable of detecting drug responsiveness without foreknowledge of specific nucleic acid sequence variations, allowing for rapid identification of new genetic mutations associated with drug resistance, drug sensitivity, and/or other drug responsive phenotypes. As such, methods provided herein can achieve greater sensitivity and diagnostic utility than existing methods based on characterized mutations.

Accordingly, variable sequence elements are provided herein which include one or more sequence variations known to be associated with a drug resistant phenotype, and assaying such variable sequence elements as described herein allows detection of the drug resistant phenotype due to known variations and/or an additional, uncharacterized variation. Advantageously, variable sequence elements provided herein are of a size that allows for a high degree of sensitivity together with a low level of false positives (e.g., a size sufficient to encode the portion of the protein altered by the known variation(s) and structurally and/or functionally related regions without including significant unrelated portions of the protein). In some embodiments, detection of a sequence variation within a variable sequence element provided herein is indicative of drug resistance with a false positive rate of less than about 25%, less than about 20%, less than about 15%, or more preferably less than about 10%, 5%, or 1%.

In various aspects, diagnostic methods are provided for determining whether a subject infected with a microorganism is amenable to treatment with a drug by measuring the responsiveness of the microorganism to the drug. In some aspects, responsiveness is measured by obtaining a biological sample from a subject, and assaying the sample for one or more sequence variations within a variable sequence element associated with responsiveness to the drug. In some preferred aspects, the variable sequence element is associated with resistance to the drug. In further preferred aspects, the variable sequence element is associated with sensitivity to the drug.

In some preferred aspects, methods are provided for detecting whether a subject is infected with drug-resistant Tb, wherein the method comprises obtaining a biological sample from the subject and assaying the sample for one or more nucleic acid sequence variations within a targeted DNA variable sequence element selected from the variable sequence elements set forth in Table 1. In some preferred embodiments, methods further comprise amplifying targeted variable sequence elements using primers set forth in Table 3.

In some aspects, methods provided herein involve a step of preparing a biological sample to facilitate detection and/or analysis of target nucleic acids. In some aspects, systems and methods are provided for preparing a biological sample for high resolution sequence analysis. In some preferred embodiments, biological samples are treated to amplify targeted DNA variable sequence elements by polymer chain reaction (PCR), or by other methods known in the art.

PCR amplification generally comprises the steps of initial denaturation, annealing, polymerization, and final extension. PCR amplification is generally conducted in a reaction chamber, which is provided with necessary PCR reagents, including the biological sample containing the target DNA, a DNA polymerase (e.g., Taq polymerase), nucleoside triphosphates, a first and second primer (comprising a primer pair) that hybridize to the target DNA and flank the sequence of the amplified DNA product (the "amplicon"). A PCR apparatus will typically include means for cycling the temperature of the reaction chamber as required for each step of the amplification cycle, including, e.g., "melting" of double stranded DNA to produce single stranded DNA; annealing of the primers to single stranded DNA templates; and extension of the amplified DNA via polymerase.

The precise conditions used to amplify a specific target DNA sequence can vary according to a number of factors which are within the knowledge of skilled artisans. In some embodiments, denaturation is conducted at between about 90-95° C. for about 10-30 seconds, annealing is conducted at about 45-65° C. for about 10-30 seconds; extension is conducted at about 70-75° C. for about 10-90 seconds; and a final extension is conducted at 72° C. for about 5 minutes. In some embodiments, the reaction mixture comprises genomic DNA, $MgCl_2$ and other physiological salts (e.g., $MnCl_2$), PCR buffer, 0.1-1.0 mM dNTPs, 0.04-1.5 μM of each primer, and 0.5-5.0 units of heat stable polymerase (e.g., Taq. polymerase).

Other amplification methods known in the art may also be utilized, including, for example, self-sustained sequence replication (3SR), strand-displacement amplification (SDA); "branched chain" DNA amplification (Chiron Corp.); ligase chain reaction (LCR), QB replicase amplification (QBR), ligation activated transcription (LAT), nucleic acid sequence-based amplification (NASBA), repair chain reaction (RCR), and cycling probe reaction (CPR) (reviewed, e.g., in *The Genesis Report*, DX; Vol. 3(4), pp. 2-7 (Feb. 1994)).

In some aspects, novel primers are provided for use in amplifying target nucleic acids for analysis according to methods provided herein. For example, in various embodiments, the primer pairs set forth in Table 2 can be used to amplify the corresponding amplicons set forth in Table 3. which can be used in various methods described herein for detecting sequence variations indicative of drug resistance.

In various aspects, sequence variations are detected within target nucleic acids according to methods provided herein using melting curve analysis (MCA). In various embodiments, MCA involves slowly heating DNA fragments in the presence of a dye that allows measurement of the relative amounts of double stranded DNA (dsDNA) and single stranded DNA (ssDNA) as a function of time and temperature, as described, e.g., in Morrison and Stols, Biochemistry, 32: 3095-3104 (1993). Suitable dyes include, but are not limited to, dsDNA-specific dyes, such as ethidium bromide, SYBR Green I, and SYBR Green II (Molecular Probes, Eugene, Oreg.), Eva Green (GENTAUR EUROPE) and ssDNA-specific dyes. In some preferred embodiments, the dye is a fluorescent dye, such as SYBR Green I, SYBR Green II, Eva Green, LC Green I, and LC Green Plus. In various embodiments, dyes can be saturating or non-saturating.

In various aspects, MCA used to detect sequence variations in methods provided herein involves incubating a sample containing a target nucleic acid with a nucleotide probe in the presence of a fluorescent DNA-binding dye, and monitoring the degree of hybridization (indicated by the level of fluorescence) as a function of time and temperature. For example, in some embodiments, a variable sequence element from Table 3 is amplified in a biological sample, and the amplified sample is incubated with a nucleotide probe complementary to the wild-type sequence set forth in Table 3 in the presence of a dsDNA-binding dye. The sample is then slowly heated at a constant rate (e.g., about 0.05 to 10.0° C. per minute) while measuring the level of fluorescence over time. In various preferred embodiments, a parallel control MCA is conducted, in which the target DNA is known to have the wild-type sequence set forth in Table 3. The target DNA is hybridized to the complementary nucleotide probes to form dsDNA at the initial low temperatures, while the dsDNA denatures as the temperature increases, converting the dsDNA to ssDNA. The conversion of dsDNA to ssDNA is accompanied by changes in fluorescence that are characteristic of the particular dye used. Advantageously, sequence variations in the biological sample can be detected by analyzing the change in fluorescence over time relative to that of the control sample.

In various preferred embodiments, MCA used in methods provided herein allows "high resolution" detection of sequence variations within a target sequence, which are detected as changes in one or more aspects of the fluorescence data. In some preferred aspects, high resolution MCA according to methods provided herein can distinguish between sample-probe and control-probe dsDNA species differing by a single base, and/or by 2, 3, 4, 5, or more bases.

In some aspects, the fluorescence data can be plotted as a function of time to determine maximum fluorescence, minimum fluorescence, the time at minimum fluorescence, and a second order rate constant for the known concentration of amplified product using the following equation:

$$F = F_{max} - \frac{F_{max} - F_{min}}{k(t - t_0)[DNA] + 1}$$

wherein F is fluorescence, $F_{max}$ is maximum fluorescence, $F_{min}$ is minimum fluorescence, k is the second order rate constant, $t_0$ is the time at $F_{min}$, and [DNA] is the known concentration of the amplified product. In some embodiments, multiple variables of the fluorescence versus time data are used to define a group of criteria that serves as an "MCA fingerprint" that uniquely identifies one or more sequences associated with a phenotype of interest, such as drug resistance. For example, in some embodiments, a drug resistant phenotype can be assayed by conducting MCA using DNA amplified from a biological sample, and comparing the fluorescence versus time data with an established MCA fingerprint.

In some preferred aspects, methods are provided for assaying a biological sample for drug-resistant tuberculosis, where the methods comprise amplifying one or more variable sequence elements selected from Table 3 using one or more of the corresponding primer pairs set forth in Table 2, and assaying the sample for sequence variations within the one or more amplified variable sequence elements using MCA. In various embodiments, the detection of one or more variations within a variable sequence element in the biological sample relative to the corresponding variable sequence element in a control sample or a known standard is indicative of drug resistance.

In various embodiments, amplified MTb DNA comprises one or more of SEQ ID NOS: 142-145, and a variation in one or more of the amplified DNA segments indicates sensitivity of MTb to rifampicin; the amplified MTb DNA comprises one or more of SEQ ID NOS: 146-151, and a variation in one or more of the amplified DNA segments indicates sensitivity of MTb to pyrazinamide; the amplified MTb DNA comprises one or more of SEQ ID NOS: 152-154, and a variation in one or more of the amplified DNA segments indicates sensitivity of MTb to streptomycin; the amplified MTb DNA comprises one or more of SEQ ID NOS: 155-176, and a variation in one or more of the amplified DNA segments indicates sensitivity of MTb to isoniazid; the amplified MTb DNA comprises one or more of SEQ ID NOS: 177-198, and a variation in one or more of the amplified DNA segments indicates sensitivity of MTb to ethambutol; the amplified MTb DNA comprises one or more of SEQ ID NOS: 199-203, and a variation in one or more of the amplified DNA segments indicates sensitivity of MTb to one or both of capreomycin and viomycin; and/or the amplified MTb DNA comprises SEQ ID NO: 204; and a variation in the amplified DNA segment indicates sensitivity of MTb to one or more of oxifloxacin, moxifloxican, gatifloxican, sitafloxacin, ofloxacin, levofloxacin, and sparfloxacin.

In some preferred aspects, methods are provided for assaying a biological sample for drug-resistant HIV, where the methods comprise amplifying the variable sequence element of SEQ ID NO: 1 using the corresponding primer pair of SEQ ID NOS: 1 and 2, and assaying the sample for sequence variations within the amplified sequence using MCA, and wherein the detection of one or more variations within the amplicon of the biological sample relative to a control sample or a known standard is indicative of drug resistant HIV. In some preferred embodiments, the detection of one or more variations within the amplicon is indicative of zidovudine and/or nevirapine resistant HIV.

In some preferred aspects, methods are provided for assaying a biological sample for drug-resistant malaria, where the methods comprise amplifying the variable sequence element of SEQ ID NO: 2 using the corresponding primer pair of SEQ ID NOS: 1 and 2, and assaying the sample for sequence variations within the amplified sequence using MCA, and wherein the detection of one or more variations within the amplicon of the biological sample relative to a control sample or a known standard is indicative of drug resistant malaria. In some preferred embodiments, the detection of one or more variations within the amplicon is indicative of chloroquine resistant malaria.

In some preferred aspects, methods are provided for assaying a biological sample for drug-resistant cancer cells, where the methods comprise amplifying the variable sequence element of SEQ ID NO: 1 using the corresponding primer pair of SEQ ID NOS: 1 and 2 and/or the variable sequence element of SEQ ID NO: 2 using the primer pair of SEQ ID NOS: 3 and 4, and assaying the sample for sequence variations within one or both of the amplified sequences using MCA, and wherein the detection of one or more variations within one or both of the amplicons of the biological sample relative to a control sample or a known standard is indicative of drug resistant cancer cells. In some preferred embodiments, the detection of one or more variations within the amplicons of SEQ ID NO: 1 and/or SEQ ID NO: 2 is indicative of epithilone and/or taxane resistant cancer cells.

In some preferred aspects, methods are provided for assaying a biological sample for drug-resistant *S. cerivisae*, where the methods comprise amplifying the variable sequence element of SEQ ID NO: 1 using the corresponding primer pair of SEQ ID NOS: 1 and 2, and assaying the sample for sequence variations within the amplified sequence using MCA, and wherein the detection of one or more variations within the amplicon of the biological sample relative to a control sample or a known standard is indicative of drug resistant *S. cerivisiae*. In some preferred embodiments, the detection of one or more variations within the amplicon is indicative of terbinafine resistant *S. cerivisiae.*

In some preferred aspects, methods are provided for assaying a biological sample for drug-resistant *S. aureus*, where the methods comprise amplifying the variable sequence element of SEQ ID NO: 1 using the corresponding primer pair of SEQ ID NOS: 1 and 2, and assaying the sample for sequence variations within the amplified sequence using MCA, and wherein the detection of one or more variations within the amplicon of the biological sample relative to a control sample or a known standard is indicative of drug resistant *S. aureus*. In some preferred embodiments, the detection of one or more variations within the amplicon is indicative of vancomycin and/or β-lactam resistant *S. aureus*.

TABLE 1A

MTb Nucleic Acid Regions associated with drug resistance

| Organism/Cells | Target Region (Gene or region) | Drug Resistance/Purpose |
|---|---|---|
| HIV | RT Connector N348I | Zidovudine/Nevirapine |
| Malaria | Chloroquine Resistance Transporter K76T | Chloroquine |
| Human cancer cells | tubulin Beta T274I | epothilone/taxanes |
| Human cancer cells | tubulin Beta R282N | epothilone/taxanes |
| *S. cerevisiae* | ERG1 F420L | Terbinafine |
| *Staphalococcus aureus* | SA1702 H164R | vancomycin/Beta-lactam |
| MTb v176F | RNA Polymerase B V176F | Rifampicin |
| MTb 80 bp HotSpot | RNA Polymerase B 80 bp hot spot | Rifampicin |
| MTb CIII a | RNA Polymerase B CIIIa | Rifampicin |
| MTb CIIIb | RNA Polymerase B CIIIb | Rifampicin |
| MTb | pncA −11 up to codon 105 | Pyrazinamide |
| MTb | pncA codons 254 to 359 | Pyrazinamide |
| MTb | pncA codons 537 to 545 | Pyrazinamide |

TABLE 1A-continued

| MTb Nucleic Acid Regions associated with drug resistance | | |
|---|---|---|
| Organism/Cells | Target Region (Gene or region) | Drug Resistance/Purpose |
| MTb | pncA codons 128 to 254 | Pyrazinamide |
| MTb | pncA codons 374 to 446 | Pyrazinamide |
| MTb | pncA codons 464 to 519 | Pyrazinamide |
| MTb | rpsL codons 43 to 88 | Streptomycin |
| MTb | rrs | Streptomycin |
| MTb | rrs | Streptomycin |
| MTb | furA detect codon 5 avoid codon 115 | Isoniazid |
| MTb | ahpC −67 ups to codon 5 | Isoniazid |
| MTb | ahpC codon 19 and 32 | Isoniazid |
| MTb | ahpC codon 73 | Isoniazid |
| MTb | ahpC codon 191 | Isoniazid |
| MTb | inhA codon 16-95 | isoniazid |
| MTb | inhA codon 194 | isoniazid |
| MTb | iniA codon 3 | isoniazid |
| MTb | iniA codons 481 and 537 | isoniazid |
| MTb | mabA −147 ups to codon 63 | isoniazid |
| MTb | Rv0340 codon 163 | isoniazid |
| MTb | Rv1592c codon 42 | isoniazid |
| MTb | Rv1592c codons 321 and 322 | isoniazid |
| MTb | Rv1592c codon 430 | isoniazid |
| MTb | katG −17 ups to codon 38 | isoniazid |
| MTb | katG codon 63 to 128 | isoniazid |
| MTb | katG codons 132 to 302 | isoniazid |
| MTb | katG codons 313 to 350 | isoniazid |
| MTb | katG codons 381 and 494 | isoniazid |
| MTb | katG codons 515 and 595 | isoniazid |
| MTb | katG codons 617 and 658 | isoniazid |
| MTb | katG codon | isoniazid |
| MTb | embC codon 394 | Ethambutol |
| MTb | embC codon 733 | Ethambutol |
| MTb | embA −43 ups to codon 14 | ethambutol |
| MTb | embA codon 210 | ethambutol |
| MTb | embA codons 321 and 350 | ethambutol |
| MTb | embA codon 462 | ethambutol |
| MTb | embA codons 833 to 913 | ethambutol |
| MTb | embB codons 297 to 332 | ethambutol |
| MTb | embB codon 406 | ethambutol |
| MTb | embB codon 497 | ethambutol |
| MTb | embB codon 745 | ethambutol |
| MTb | embB codons 955 to 1024 | ethambutol |
| MTb | rmlA2 codon 152 | ethambutol |
| MTb | iniC codons 245 to 251 | ethambutol |
| MTb | iniA codon 308 | ethambutol |
| MTb | iniA codon 501 | ethambutol |
| MTb | iniB −89 ups to codon 47 | ethambutol |
| MTb | Rv3124 −16 ups to codon 54 | ethambutol |
| MTb | RmlD −71 ups | ethambutol |
| MTb | RmlD codon 284 | ethambutol |
| MTb | embR −136 ups | ethambutol |
| MTb | embR codon 379 | ethambutol |
| MTb | thyA nt 7 to 64 | Capreomycin/Viomycin |
| MTb | thyA nt 200 to 310 | Capreomycin/Viomycin |
| MTb | thyA nt 353 to 400 | Capreomycin/Viomycin |
| MTb | thyA nt 477 to 586 | Capreomycin/Viomycin |
| MTb | thyA nt 653 to 758 | Capreomycin/Viomycin |
| MTb | gyrA codons 90 and 94 | oxifloxacin (Moxifloxacin/ Gatifloxacin/Sitafloxacin/ Ofloxacin/Levofloxacin/ Sparfloxacin) |

MTb—*Mycobacterium tuberculosis*

The isolation of suitable quantities of *Mycobacterium tuberculosis* from sputum samples poses a significant challenge to the molecular diagnostic community. Sputum samples often contain such low quantities of live MTb that isolates must be grown for up to 2 months to ensure sufficient quantities of genetic material for use in molecular diagnostic applications. Although many molecular diagnostic techniques can enable detection of very small quantities of starting materials, as low as single copy, it is often difficult to ensure that a particular sample in fact contains the desired quantity of starting material.

To enable the use of very rare or precious samples in molecular diagnostic procedures, a technique known as whole genome amplification has been employed to enrich the starting material for use in the downstream molecular diagnostic procedures. As such, some embodiments of methods described herein apply whole genome amplification methods to the problem of screening sputum samples containing MTb. Various methods provided herein can also be used for detecting the presence or absence of one or more nucleic acid sequences in a sample containing a nucleic acid or mixture of nucleic acids, or for distinguishing between two different sequences in such a sample.

In various embodiments, methods are provided for improving the detection of nucleic acid sequences in biological samples using real-time PCR, dsDNA binding dyes, and fluorescent probe-based approaches.

In some embodiments, methods are provided for preparing microorganism nucleic acids for amplification and high resolution analysis. Microorganisms, such as *Mycobacterium tuberculosis* (MTb), can be isolated using conventional sample fractionation protocols, and the nucleic acids of the microorganism can be extracted and amplified using well-known, novel, or yet to be established methods.

Following molecular enrichment and amplification, the nucleic acids are screened in various aspects for the presence of any of a variety of genetic markers using a quantitative method such as PCR. Nucleic acids may also be quantified for downstream analysis. Any method of quantification may be used, including but not limited to, qPCR analysis, UV analysis, gel analysis, and nucleic acid quantification kits. In some embodiments, a final amplification of nucleic acids is performed to amplify nucleic acids and segments thereof of interest, such as drug (e.g., antibiotic) susceptibility targets. Saturating dyes can be used to track amplification, hybridization, and denaturation of nucleic acids.

In some embodiments, amplified target nucleic acids can be monitored during hybridization and/or denaturation using high resolution monitoring techniques, such as those that measure changes in fluorescence associated with changes in the structure and/or conformation of the nucleic acids, such as those accompanying hybridization and melting. Control target nucleic acids may be similarly monitored in parallel. Variations detected between target nucleic acids (e.g., drug susceptibility region) and control nucleic acids can be indicative of reduced susceptibility (e.g., resistance) to drugs that target particular regions of the gene products formed from the target nucleic acids.

In various embodiments, methods are provided for isolating, amplifying, and analyzing target nucleic acids of a microorganism, such as MTb, as described below and throughout the specification. In other embodiments, target nucleic acids, such as those set forth in Table 1, can be isolated from cellular or clinical samples by methods established in the art.

In some embodiments, isolated MTb is fractionated from a sputum sample using a conventional live organism preparation method, such as the Petroff method, that leaves small quantities of the MTb organism in an aqueous suspension. MTb nucleic acids are isolated from the sample using a commercially available kit MycoBuffer, (RAOGene; Milford, Pa.) according to manufacturer's instruction, such that at least small quantities of MTb DNA are isolated in the residual material from the MycoBuffer product. Larger quantities of DNA may be isolated.

The DNA samples obtained from the use of the lysis solution are submitted to a primary screen for MTb DNA using any method of DNA amplification that inhibits or eliminates the formation of nonspecific nucleic acid products. Also, the amplification method can be performed for extended time periods to account for the low quantity of DNA typically present in primary lysates. Exemplary primers covering these regions of interest are presented in Table 2.

TABLE 2

Exemplary primers for amplification of target regions

| Organism | Target | Seq. No. | Forward | Reverse | Accession # |
|---|---|---|---|---|---|
| HIV | RT Connector N348I | 1 | AAGGCCAATGGACATATC AAA | GGGCACCCCT CATTCTT | NP_705927 |
| Malaria | Chloroquine Resistance Transporter K76T | 3 | TATTTATTTAAGTGTATGT GTAATG | CAATTTTGTTT AAAGTTCTTT TAGC | MAL7P1.27 |
| Human cancer cells | tubulin Beta T274I | 5 | TCCCACGTCTCCATTT | TGAGTTCCGG CACTGT | NP_821133 |
| Human cancer cells | tubulin Beta R282N | 5 | TCCCACGTCTCCATTT | TGAGTTCCGG CACTGT | NM_178014 |
| S. cerevisiae | ERG1 F420L | 7 | TTCAATGCTAAGAATCCTG CTC | AGATTGGCAT ATGATCACTA CC | M64994 |
| staph aureus | SA1702 H164R | 9 | AAAGCTGCAAATATTAAG GA | GGCAATATAA CCTGCAC | NC_002745 |
| MTb v176F | RNA Polymerase B V176F | 11 | GAGCGTGTGGTGGTCAG | CGTCTTGTCG GTGGACT | BX842579 |
| MTb 80bp HotSpot | RNA Polymerase B 80bp hot spot | 13 | CAAGGAGTTCTTCGGCAC C | GGACCTCCAG CCCGGCA | |
| MTb CIII a | RNA Polymerase B CIIIa | 15 | GGTGGCACAGGCCAAT | GAAGCGACCG TCCGCA | |

TABLE 2-continued

Exemplary primers for amplification of target regions

| Organism | Target | Seq. No. | Forward | Reverse | Accession # |
|---|---|---|---|---|---|
| MTb CIIIb | RNA Polymerase B CIIIb | 17 | CCGCGCGTGCTGGTC | TCCATGTAGT CCACCTCAG | |
| MTb | pncA -11 to 105 | 19 | CAGTCGCCCGAACGTA | TGGTAGTCCG CCGCT | NC_000962 |
| MTb | pncA 254 to 359 | 21 | CAATCGAGGCGGTGTTCT | CGACGCCGCG TTG | |
| MTb | pncA 537 to 545 | 23 | GATGCGCACCGCCA | GCGGTGCCAT CAGGAG | |
| MTb | pncA 128 to 254 | 25 | GCGGCGGACTACCAT | GATTGCCGAC GTGTCCAG | |
| MTb | pncA 374 to 446 | 27 | GCAACGCGGCGTC | CCCTGGTGGC CAAGC | |
| MTb | pncA 464 to 519 | 29 | GCTTGGCCACCAGGG | CTGGCGGTGC GCATC | |
| MTb | rpsL | 31 | CCGCGTGTACACCACCA | AGCGCACACC AGGCAG | AF367438 |
| MTb | rrs | 33 | GGATTGACGGTAGGTGGA GA | ACGCTCGCAC CCTACGTATT A | cp000717.1 |
| MTb | rrs | 35 | CCCGCCTGGGGAGT | CATGCTCCGC CGCTT | L15307.1 |
| MTb | furA detect codon 5 avoid codon 115 | 39 | TAGCCAAAGTCTTGACTG AT | GCGCATTCAC TGCTTC | Rv1909c |
| MTb | ahpC -67 ups to codon 5 | 39 | TGTGATATATCACCTTTGC CT | CGGGGAATTG ATCGCC | Rv2428 |
| MTb | ahpC codon 19 and 32 | 41 | ACCAGCTCACCGCTC | GGTGATAGTG GTGAAGTAGT | |
| MTb | ahpC condon 73 | 43 | GCGTTCAGCAAGCTCA | CGCGAATTCG CTGTCA | |
| MTb | ahpC cond 191 | 45 | CTGTGCGCATGCAAC | TCCCGGTTAG GCCGA | |
| MTb | inhA codon 16-95 | 47 | CAAACGGATTCTGGTTAG CG | GGTTGATGCC CATCCCG | Rv1484 |
| MTb | inhA codon 194 | 49 | CAAGTACGGTGTGCGTT | GCCGACGATC GCACTC | Rv1484 |
| MTb | iniA codon 3 | 51 | GAGCCGATTTCACGAACC | CTCGTTTACG CCTCAGA | |
| MTb | iniA codons 481 537 | 53 | TGGGCCGGATGGAATC | GACGACGAAC GAAATGT | Rv0342 |
| MTb | mabA -147 ups to codon 63 | 55 | CTGCTGCGCAATTCGTA | GATCCCCCGG TTTCCT | Rv1483 |
| MTb | Rv0340 condone 163 | 57 | GCCGACAGACCATCC | GTCGTAGCCG TGATGA | Rv0340 |
| MTb | Rv1592c aa42 | 59 | TCCGACGATCCGTTCTAC | GAGCGCAACA CCGTTCC | Rv1592c |
| MTb | Rv1592c aa321 322 | 61 | GACTTCCTCGACGAACC | GCCTGCACGA TCAATACC | rv1592c |
| MTb | Rv1592c aa430 | 63 | TTCAACCCGATGACCTAC G | GGTGATCACC TTGGCCG | rv1592c |

TABLE 2-continued

Exemplary primers for amplification of target regions

| Organism | Target | Seq. No. | Forward | Reverse | Accession # |
|---|---|---|---|---|---|
| MTb | katG -17 ups to codon 38 | 65 | TGGGGTCTATGTCCTGA | GCAGTACCTT CAGATTGAG | Rv1908c |
| MTb | katG codon 63 to 128 | 67 | GGCTCAATCTGAAGGTAC T | GGGCCAGCTG TTAAG | rv1908c |
| MTb | katG codon 132 to 302 | 69 | TTCGCGCCGCTTAAC | GGTTCCGGTG CCATAC | rv1908c |
| Mtb | katG codon 313 to 350 | 71 | GTATGGCACCGGAACC | TCCTTGGCGG TGTATTG | rv1908c |
| Mtb | katG codon 381 494 | 73 | CGCTCCCCGACGATG | GACTTGTGGC TGCAGG | rv1908c |
| MTb | katG codon 515 595 | 75 | CCTGCAGCCACAAGT | GCAGGTTCGC CTTGTC | rv1908c |
| Mtb | katG codon 617 658 | 77 | CGGCCGAGTACATGC | GGCTCCCAGG TGATAC | rv1908c |
| Mtb | katG cddon | 79 | GGCAAGGATGGCAGT | GCACGTCGAA CCTGT | rv1908c |
| MTb | embC394 | 81 | GGCGGGCATGTTTCT | GGCGATGATC GGCTC | embC |
| MTb | embC733 | 83 | GGCGATGATTTCCCAGT | GCCAAAGCCT GTAGGT | embC |
| MTb | embA-4314 | 85 | TCGGCGACAACCTCC | GCCCCGGATA CCAGAG | embA |
| MTb | embA 210 | 87 | ACTCGGTTTATCACGACG | CCATGGCTAC CAGGAC | embA |
| MTb | embA321350 | 89 | GTATACATCGGTGCTTGC | GCACCAGCGG TGAACA | embA |
| MTb | embA462 FOR | 91 | GCGACCGATGGACTG | CCACCACGGT GATCAG | embA |
| MMTb | embA833913 | 93 | CGCCATCACCGACTC | TTGCGGTCCG ATGTC | embA |
| MMTb | embB 297 & 332 | 95 | TTCGGCTTCCTGCTCT | GGTTTGCTGG CCTCC | embB |
| MTb | emb 406 | 97 | TCAACAACGGCCTGC | ATGGACCGCT CGATCA | embB |
| MMTb | emb 497 | 99 | CACCGTCATCCTGACC | TTTTGGCGCG AACCC | embB |
| MTb | embB 745 | 101 | GGCTGGTCCAACGTG | GCATTGGTAT CAGGCTCG | embB |
| Mtb | embB 9551024 | 103 | TTCGCCCGAGCAAAG | CCGTTAGTGC CGTCT | embB |
| MTb | rm1A2 152 | 105 | ATGTCACGCTGCAAC | GATCCTCCGT CTTCTCCA | rm1A2 |
| MTb | iniC 245 251 | 107 | CGCGAACTGAACCAGA | GCGGTATGCG CCTTA | iniC |
| MTb | iniA 308 | 109 | GAGCAGGTGCTTTCCC | CTCTGTTGCC GAACG | iniA |
| MTb | iniA 501 | 111 | GGGTTCCTATGGCGG | GGTTGAACAA CCCAAGTC | iniA |

TABLE 2-continued

Exemplary primers for amplification of target regions

| Organism | Target | Seq. No. | Forward | Reverse | Accession # |
|---|---|---|---|---|---|
| MTb | iniB -89 47 | 113 | CGATCCCGATAGGTGTTT | GGCACCCAGA TTCAGAC | iniB |
| MTb | Rv3124-16 54 | 115 | ATCACAGGAGTGGAGTT | AAGATGTTGC GCGAAT | Rv3124 |
| MTb | RmlD -71 | 117 | TACGAACCACACGTTGC | GTTGGCTACC CGACAG | RmlD |
| MTb | RmlD 284 | 119 | GCTTGACGCCGCTAC | GAAGTTGAGT TCGCAGGT | rmlD |
| MTb | embR -136 | 121 | CAGCCGATGCCGCTG | CGCCGATGCG GTAAGAA | embR |
| MTb | embR 379 | 123 | ACAGCGCCAACGTCA | GACGATCGGA GGTCGT | embR |
| MTb | thyA nt7to64 | 125 | TCGCCGCTAGGCTGA | ATCTGCTGGC CGAAC | thyA |
| MTb | thyA ntnt200to310 | 127 | CGGGTACGCCCAAAT | CCAGATGGTG ACTCCG | thyA |
| MTb | thyA nt353to400 | 129 | ATTCCAATATCGGTTGGC | CCACGATCGC CATTGT | thyA |
| MTb | thyA nt477 to 586 | 131 | GGTGAGCACATCGACC | ATAGCTGGCG ATGTTGA | thyA |
| MTb | thyA nt 653 to 758 | 133 | CGCCGACCTGTTTCT | CGGCTAGAAG TAGTTTCG | thyA |
| MTb | gyrA 9094 | 135 | GCAACTACCACCCGCA | GTAGCGCAGC GACCA | gyrA |

MTb—Mycobacterium tuberculosis

In further embodiments, DNA samples obtained from the use of the lysis solution are combined, either following the results from the primary screen or simultaneous to the screen, with reaction ingredients similar to those used in whole genome amplification procedures.

However, other suitable amplification procedures can be utilized that enables the DNA samples to be amplified to a suitable amount of genomic nucleic acid. Whole genome amplification procedures can provide molecular enrichment of the DNA samples with increases in quantities of the MTb genome in excess of 30 fold in less than 16 hours of incubation time. Whole genome amplification need only be used if there is not enough template to obtain a primary amplification.

The enriched DNA is subsequently purified using any of a variety of methods for purifying DNA. For example, a filter plate system capable of accommodating 96 or more simultaneous samples can be used to purify an array of samples of enriched DNA. The enriched and purified DNA is subjected to a MTb or general mycobacterium-specific PCR amplification protocol, and the amount or concentration of the DNA is determined. For example, real-time quantitative PCR can be used to amplify and determine the amount of MTb DNA in the sample. Purification is not necessary if whole genome amplification is not used.

The sample concentration is adjusted in order to match the concentration of the enriched MTb DNA with control MTb DNA so as to achieve a ratio of approximately 1:1 or another pre-determined and fixed ratio. This allows for a near equivalent ratio of the enriched MTb DNA with that of the control DNA to be used in subsequent detection steps. The enriched MTb DNA that has been normalized for concentration is co-amplified with the control MTb DNA that contains the reference gene sequence for the target region of the nucleic acid. That is, the control MTb DNA contains a gene region (e.g., sequence) that if variant, is indicative of a reduced susceptibility (e.g., resistance) of the MTb organism to drugs (e.g., antibiotic or antimycotic drugs) targeting the gene region. Exemplary gene regions and corresponding drug sensitivities amplified by the primer pairs presented in Table 2 are provided in Table 3. These regions enabled the determination of drug resistance or sensitivity in *Mycobacterium tuberculosis* infection as well as for examples of Zidovudine sensitivity in HIV, taxane sensitivity in human cancers, chloroquine sensitivity in malaria, terbinafine sensitivity in *S. cerivisiae*, and Vancomycin sensitivity in *S. aureus*.

TABLE 3

Exemplary regions for drug sensitivity testing of MTb

| Organism | Drug | Amplicon-Sensitive | SEQ ID NO | Design Tm | Reference |
|---|---|---|---|---|---|
| HIV | Zidovudine/ Nevirapine | **AAGGCCAATGGACAT ATCAAA**TTTATCAAGA GCCATTTAAAAATCTG AAAACAGGAAAATAT GCAAGAATGAGGGGT GCCC | 137 | 75.1 | www.plosmedicine.org 1890 December 2007 volume 4, Issue 12 |
| Malaria | Chloroquine | **TATTTATTTAAGTGTA TGTGTAATG**AATAAA ATTTTTGCTAAAAGAA CTTTAAACAAAATTG | 138 | 64.5 | The Journal of Infectious Diseases 2001; 183: 1413-6 |
| Human cancer cells | epothilone/ taxanes | TCCCACGTCTCCATTTC TTTATGCCTGGCTTTGC CCCTCTCACCAGCCGT GGAAGCCAGCAGTATC GAGCTCTCACAGTGCC GGAACTCA | 139 | 84.4 | PNAS Mar. 14, 2000 vol. 97 no. 6, pages 2904-2909 |
| Human cancer cells | epothilone/ taxanes | TCCCACGTCTCCATTTC TTTATGCCTGGCTTTGC CCCTCTCACCAGCCGT GGAAGCCAGCAGTATC GAGCTCTCACAGTGCC GGAACTCA | 139 | 84.4 | PNAS Mar. 14, 2000 vol. 97 no. 6, pages 2904-2909 |
| S. cerevisiae | Terbinafine | TTCAATGCTAAGAATC CTGCTCCTATGCACGG TCACGTTATTCTTGGTA GTGATCATATGCCAAT CT | 140 | 75.3 | ANTIMICROBIAL AGENTS AND CHEMOTHERAPY, December 2003, p. 3890-3900 Vol. 47, No. 12 |
| S. aureus | vancomycin/ Beta-lactam | **AAAGCTGCAAATATT AAGGA**AAATAATACC ATTGTTGTTAGACACA TTTTAGGTAAAGTGCA GGTTATATTGCC | 141 | 71.4 | PNAS May 29, 2007 vol. 104 no. 22 9451-9456 |
| MTb v176F | Rifampicin | **GAGCGTGTGGTGGTC AG**CCAGCTGGTGCGGT CGCCCGGGGTGTACTT CGACGAGACCATTGAC AAGTCCACCGACAAGA CG | 142 | 85.7 | ANTIMICROBIAL AGENTS AND CHEMOTHERAPY, June 2005, p. 2200-2209 Vol. 49, No. 6 |
| MTb 80bp HotSpot | Rifampicin | **CAAGGAGTTCTTCGG CACC**AGCCAGCTGAGC CAATTCATGGACCAGA ACAACCCGCTGTCGGG GTTGACCCACAAGCGC CGACTGTCGGCGCTGG GGCCCGGCGGTCTGTC ACGTGAGCGTGCCGGG CTGGAGGTCC | 143 | 90.8 | JOURNAL OF CLINICAL MICROBIOLOGY, May 2003, p. 2209-2212 Vol. 41, No.5 ANTIMICROBIAL AGENTS AND CHEMOTHERAPY, October 1994, p. 2380-2386 Vol. 38, No. 10 |
| MTb CIIIa | Rifampicin | **GGTGGCACAGGCCAA TT**CGCCGATCGATGCG GACGGTCGCTTC | 144 | 80.9 | ANTIMICROBIAL AGENTS AND CHEMOTHERAPY, June 2005, p. 2200-2209 Vol. 49, No. 6 |
| MTb CIIIb | Rifampicin | **CCGCGCGTGCTGGTC** CGCCGCAAGGCGGGCG AGGTGGAGTACGTGCC TCGTCTGAGGTGGAC TACATGGA | 145 | 8738 | ANTIMICROBIAL AGENTS AND CHEMOTHERAPY, June 2005, p. 2200-2209 Vol. 49, No. 6 |
| MTb | Pyrazinamide | **CAGTCGCCCGAACGT AT**GGTGGACGTATGCG GGCGTTGATCATCGTC GACGTGCAGAACGACT TCTGCGAGGGTGGCTC | 146 | 91.2 | ANTIMICROBIAL AGENTS AND CHEMOTHERAPY, August 2004, p. 3209-3210 Vol. 48, No. 8; |

TABLE 3-continued

Exemplary regions for drug sensitivity testing of MTb

| Organism | Drug | Amplicon-Sensitive | SEQ ID NO | Design Tm | Reference |
|---|---|---|---|---|---|
| | | GCTGGCGGTAACCGGTGGCGCCGCGCTGGCCCGCGCCATCAGCGACTACCTGGCCGAAGCGGCGGACTACCA | | | Microbiology (1997), 143, 3367-3373; JOURNAL OF CLINICAL MICROBIOLOGY, February 2007, p. 595-599 Vol. 45, No. 2 |
| MTb | Pyrazinamide | **CAATCGAGGCGGTGTTCT**ACAAGGGTGCCTACACCGGAGCGTACAGCGGCTTCGAAGGAGTCGACGAGAACGGCACGCCACTGCTGAATTGGCTGCGGCAACGCGGCGTCG | 147 | 87.9 | As above |
| MTb | Pyrazinamide | **GATGCGCACCGCCAG**CGTCGAGTTGGTTTGCAGCTCCTGATGGCACCGC | 148 | 83.1 | As above |
| MTb | Pyrazinamide | **GCGGCGGACTACCAT**CACGTCGTGGCAACCAAGGACTTCCACATCGACCCGGGTGACCACTTCTCCGGCACACCGGACTATTCCTCGTCGTGGCCACCGCATTGCGTCAGCGGTACTCCCGGCGCGGACTTCCATCCCAGTCTGGACACGTCGGCAATC | 149 | 89.5 | As above |
| MTb | Pyrazinamide | **GCAACGCGGCGTC**GATGAGGTCGATGTGGTCGGTATTGCCACCGATCATTGTGTGCGCCAGACGGCCGAGGACGCGGTACGCAATGGCTTGGCCACCAGGG | 150 | 88.3 | As above |
| MTb | Pyrazinamide | **GCTTGGCCACCAGGG**TGCTGGTGGACCTGACAGCGGGTGTGTCGGCCGATACCACCGTCGCCGCGCTGGAGGAGATGCGCACCGCCAG | 151 | 90.1 | As above |
| MTb | Streptomycin | **CCGCGTGTACACCACCA**CTCCGAAGAAGCCGAACTCGGCGCTTCGGAAGGTTGCCCGCGTGAAGTTGACGAGTCAGGTCGAGGTCACGGCGTACATTCCCGGCGAGGGCCACAACCTGCAGGAGCACTCGATGGTGCTGGTGCGCGGCGGCCGGGTGAAGGACCTGCCTGGTGTGCGCT | 152 | 91.5 | ANTIMICROBiAL AGENTS AND CHEMOTHERAPY, February 1994, p. 228-233 Vol. 38, No.2; ANTIMICROBIAL AGENTS AND CHEMOTHERAPY, October 2001, p. 2877-2884 Vol. 45, No. 10; JOURNAL OF BACTERIOLOGY, May 2005, p. 3548-3550 Vol. 187, No. 10; |
| MTb | Streptomycin | **GGATTGACGGTAGGTGGAGA**AGAAGCACCGGCCAACTACGTGCCAGCAGCCGCGGTAATACGTAGGGTGCGAGCGT | 153 | 84.5 | As above |
| MTb | Streptomycin | **CCCGCCTGGGGAGT**ACGGCCGCAAGGCTAAAACTCAAAGGAATTGACGGGGGCCCGCACAAGCGGCGGAGCATG | 154 | 86.7 | As above |

TABLE 3-continued

Exemplary regions for drug sensitivity testing of MTb

| Organism | Drug | Amplicon-Sensitive | SEQ ID NO | Design Tm | Reference |
|---|---|---|---|---|---|
| MTb | Isoniazid | **TAGCCAAAGTCTTGA CTGAT**TCCAGAAAAG GGAGTCATATTGTCTA GTGTGTCCTCTATACC GGACTACGCCGAACAG CTCCGGACGGCCGACC TGCGCGTGACCCGACC GCGCGTCGCCGTCCTG GAAGCAGTGAATGCGC | 155 | 86.82 | ANTIMICROBIAL AGENTS AND CHEMOTHERAPY, April 2003, p. 1241-1250 Vol. 47, No.4; |
| MTb | Isoniazid | **TGTGATATATCACCT TTGCCT**GACAGCGACT TCACGGCACGATGGAA TGTCGCAACCAAATGC ATTGTCCGCTTTGATG ATGAGGAGAGTCATGC CACTGCTAACCATTGG CGATCAATTCCCCG | 156 | 83 | ANTIMICROBIAL AGENTS AND CHEMOTHERAPY, March 1997, p. 600-606 Vol. 41, No.3; ANTIMICROBIAL AGENTS AND CHEMOTHERAPY, August 2006, p. 2640-2649 Vol. 50, No. 8; |
| MTb | Isoniazid | **ACCAGCTCACCGCTC** TCATCGGCGGTGACCT GTCCAAGGTCGACGCC AAGCAGCCCGGCGACT ACTTCACCACTATCAC C | 157 | 85.7 | As above |
| MTb | Isoniazid | **GCGTTCAGCAAGCTC A**ATGACGAGTTCGAGG ACCGCGACGCCCAGAT CCTGGGGGTTTCGATT GACAGCGAATTCGCG | 158 | 84 | As above |
| MTb | Isoniazid | **CTGTGCGCATGCAAC** TGGCGCAAGGGCGACC CGACGCTAGACGCTGG CGAACTCCTCAAGGCT TCGGCCTAACCGGGA | 159 | 87.4 | As above |
| MTb | isoniazid | **CAAACGGATTCTGGT TAGCG**GAATCATCACC GACTCGTCGATCGCGT TTCACATCGCACGGGT AGCCCAGGAGCAGGG CGCCCAGCTGGTGCTC ACCGGGTTCGACCGGC TGCGGCTGATTCAGCG CATCACCGACCGGCTG CCGGCAAAGGCCCCGC TGCTCGAACTCGACGT GCAAAACGAGGAGCA CCTGGCCAGCTTGGCC GGCCGGGTGACCGAGG CGATCGGGGCGGGCAA CAAGCTCGACGGGGTG GTGCATTCGATTGGGT TCATGCCGCAGACCGG GATGGGCATCAACC | 160 | 92.6 | ANTIMICROBIAL AGENTS AND CHEMOTHERAPY, August 2006, p. 2640-2649 Vol. 50, No. 8 |
| MTb | isoniazid | **AAGTACGGTGTGCGT T**CGAATCTCGTTGCCG CAGGCCCTATCCGGAC GCTGGCGATGAGTGCG ATCGTCGGCGGTGCGC TCGGCGAGGAGGCCGG CGCCCAGATCCAGCTG CTCGAGGAG | 161 | 90.4 | As above |
| MTb | isoniazid | **GAGCCGATTTCACGA ACC**GGTGGGGACGTTC ATGGTCCCCGCCGGTT | 162 | 84.5 | ANTIMICROBIAL AGENTS AND CHEMOTHERAPY, |

TABLE 3-continued

| Exemplary regions for drug sensitivity testing of MTb | | | | | |
|---|---|---|---|---|---|
| Organism | Drug | Amplicon-Sensitive | SEQ ID NO | Design Tm | Reference |
| | | TGTGCGCATACCGTGA TCTGAGGCGTAAACGA G | | | April 2003, p. 1241-1250 Vol. 47, No. 4 |
| Mtb | isoniazid | **TGGGCCGGATGGAAT C**GAAACCGCTGCGCCG GGGCCATAAAATGATT ATCGGCATGCGGGGTT CCTATGGCGGCGTGGT CATGATTGGCATGCTG TCGTCGGTGGTCGGAC TTGGGTTGTTCAACCC GCTATCGGTGGGGGCC GGGTTGATCCTCGGCC GGATGGCATATAAAGA GGACAAACAAAACCG GTTGCTGCGGGTGCGC AGCGAGGCCAAGGCC AATGTGCGGCGCTTCG TCGACGACATTTCGTT CGTCGTC | 163 | 90.2 | ANTIMICROBIAL AGENTS AND CHEMOTHERAPY, Aprir 2003, p. 1241-1250 Vol. 47, No. 4 |
| MTb | isoniazid | **CTGCTGCGCAATTCG TA**GGGCGTCAATACAC CCGCAGCCAGGGCCTC GCTGCCCAGAAAGGGA TCCGTCATGGTCGAAG TGTGCTGAGTCACACC GACAAACGTCACGAGC GTAACCCCAGTGCGAA AGTTCCCGCCGGAAAT CGCAGCCACGTTACGC TCGTGGACATACCGAT TTCGGCCCGGCCGCGG CGAGACGATAGGTTGT CGGGGTGACTGCCACA GCCACTGAAGGGGCCA AACCCCCATTCGTATC CCGTTCAGTCCTGGTT ACCGGAGGAAACCGG GGGATC | 164 | 90.5 | ANTIMICROBIAL AGENTS AND CHEMOTHERAPY, April 2003, p. 124 1-1250 Vol. 47, No. 4 |
| MTb | isoniazid | **GCCGACAGACCATCC** GGCTGTCTGGAACCAC CCGGTCGTTGACCCAC ATACCGTCGAGCCCGA TCATCACGGCTACGAC | 165 | 85.3 | ANTIMICROBIAL AGENTS AND CHEMOTHERAPY, April 2003, p. 1241-1250 Vol. 47, No. 4 |
| MTb | isoniazid | **TCCGACGATCCGTTC TAC**TTCCCACCTGCCG GCTACCAGCATGCCGT GCCCGGAACGGTGTTG CGCTC | 166 | 85.8 | ANTIMICROBIAL AGENTS AND CHEMOTHERAPY, April 2003, p. 1241-1250 Vol. 47, No. 4 |
| MTb | isoniazid | **GACTTCCTCGACGAA CC**CCTTGAGGACATTC TGTCGACGCCGGAAAT TTCCCATGTCTTCGGC GACACCAAGCTGGGTA GCGCGGTGCCCACCCC GCCGGTATTGATCGTG CAGGC | 167 | 87.4 | As above |
| Mtb | isoniazid | **TTCAACCCGATGACC TACG**CCGGCATGGCGA GACTGGCCGTGATCGC GGCCAAGGTGATCACC | 168 | 84.7 | As above |
| MTb | isoniazid | **TGGGGTCTATGTCCT GA**TTGTTCGATATCCG ACACTTCGCGATCACA TCCGTGATCACAGCCC GATAACACCAACTCCT GGAAGGAATGCTGTGC | 169 | 88.9 | ANTIMICROBIAL AGENTS AND CHEMOTHERAPY, August 2006, p. 2640-2649 Vol. 50, No. 8; ANTIMICROBIAL |

TABLE 3-continued

| Exemplary regions for drug sensitivity testing of MTb | | | | | |
|---|---|---|---|---|---|
| Organism | Drug | Amplicon-Sensitive | SEQ ID NO | Design Tm | Reference |
| | | CCGAGCAACACCCACC CATTACAGAAACCACC ACCGGAGCCGCTAGCA ACGGCTGTCCCGTCGT GGGTCATATGAAATAC CCCGTCGAGGGCGGCG GAAACCAGGACTGGTG GCCCAACCGGCTCAAA GTATACTTTATGGGGC AGCTCCCGCCGCCTTT GGTCCTGACCACCGGG TTGGCC**GAGTT**TCTGA AGGTACTGC | | | AGENTS AND CHEMOTHERAPY, October 2005, p. 4068-4074 Vol. 49, No. 10; JOURNAL OF CLINICAL MICROBIOLOGY, October 2003, p. 4630-4635 Vol. 41, No. 10 |
| Mtb | isoniazid | **GGCTCAATCTGAAGG TACT**GCACCAAAACCC GGCCGTCGCTGACCCG ATGGGTGCGGCGTTCG ACTATGCCGCGGAGGT CGCGACCATCGACGTT GACGCCCTGACGCGGG ACATCGAGGAAGTGAT GACCACCTCGCAGCCG TGGTGGCCCGCCGACT ACGGCCACTACGGGCC GCTGTTTATCCGGATG GCGTGGCACGCTGCCG GCACCTACCGCATCCA CGACGGCCGCGGCGGC GCCGGGGGCGGCATGC AGCGGTTCGCGCCGCT TAACAGCTGGCCC | 170 | 94.1 | As above |
| MTb | isoniazid | **TTCGCGCCGCTTAAC** AGCTGGCCCGACAACG CCAGCTTGGACAAGGC GCGCCGGCTGCTGTGG CCGGTCAAGAAGAAGT ACGGCAAGAAGCTCTC ATGGGCGGACCTGATT GTTTTCGCCGGCAACT GCGCGCTGGAATCGAT GGGCTTCAAGACGTTC GGGTTCGGCTTCGGCC GGGTCGACCAGTGGGA GCCCGATGAGGTCTAT TGGGGCAAGGAAGCC ACCTGGCTCGGCGATG AGCGTTACAGCGGTAA GCGGGATCTGGAGAAC CCGCTGGCCGCGGTGC AGATGGGGCTGATCTA CGTGAACCCGGAGGGG CCGAACGGCAACCCGG ACCCCATGGCCGCGGC GGTCGACATTCGCGAG ACGTTTCGGCGCATGG CCATGAACGACGTCGA AACAGCGGCCCGCCAG CTGTAAGCGCTCTGCA AAGCCGCGTACCGGTA CTTGCTGCAGCTTTGTC GCCGGCTGATCGTCGG CGGTCACACTTTCGGT AAGACCCATGGCGCCG GCCCGGCCGATCTGGT CGGCCCCGAACCCGAG GCTGCTCCGCTGGAGC AGATGGGCTTGGGCTG GAAGAGCTCGTAGCCG GGGCTTGGGCTCCGAC GAGGCGACCTCGTCTA | 171 | 93.6 | As above |

TABLE 3-continued

Exemplary regions for drug sensitivity testing of MTb

| Organism | Drug | Amplicon-Sensitive | SEQ ID NO | Design Tm | Reference |
|---|---|---|---|---|---|
| | | CCCGAACCCGACCTTC<br>TCGAG**CAT**TGGCACCG<br>GAACC | | | |
| Mtb | isoniazid | **GTATGGCACCGGAAC**<br>**C**GGTAAGGACGCGATC<br>ACCAGCGGCATCGAGG<br>TCGTATGGACGAACAC<br>CCCGACGAAATGGGAC<br>AACAGTTTCCTCGAGA<br>TCCTGTACGGCTACGA<br>GTGGGAGCTGACGAAG<br>AGCCCTGCTGGCGCTT<br>GGCAATACACCGCCAA<br>GGA | 172 | 87.8 | |
| Mtb | isoniazid | **CGCTCCCCGACGATG**<br>CTGGCCACTGACCTCT<br>CGCTGCGGGTGGATCC<br>GATCTATGAGCGGATC<br>ACGCGTCGCTGGCTGG<br>AACACCCCGAGGAATT<br>GGCCGACGAGTTCGCC<br>AAGGCCTGGTACAAGC<br>TGATCCACCGAGACAT<br>GGGTCCCGTTGCGAGA<br>TACCTTGGGCCGCTGG<br>TCCCCAAGCAGACCCT<br>GCTGTGGCAGGATCCG<br>GTCCCTGCGGTCAGCC<br>ACGACCTCGTCGGCGA<br>AGCCGAGATTGCCAGC<br>CTTAAGAGCCAGATCC<br>GGGCATCGGGATTGAC<br>TGTCTCACAGCTAGTT<br>TCGACCGCATGGGCGG<br>CGGCGTCGTCGTTCCG<br>TGGTAGCGACAAGCGC<br>GGCGGCGCCAACGGTG<br>GTCGCATCCGCCTGCA<br>GCCACAAGTC | 173 | 92.5 | As above |
| MTb | isoniazid | **CCTGCAGCCACAAGT**<br>CGGGTGGGAGGTCAAC<br>GACCCCGACGGGGATC<br>TGCGCAAGGTCATTCG<br>CACCCTGGAAGAGATC<br>CAGGAGTCATTCAACT<br>CCGCGGCGCCGGGGAA<br>CATCAAAGTGTCCTTC<br>GCCGACCTCGTCGTGC<br>TCGGTGGCTGTGCCGC<br>CATAGAGAAAGCAGC<br>AAAGGCGGCTGGCCAC<br>AACATCACGGTGCCCT<br>TCACCCCGGGCCGCAC<br>GGATGCGTCGCAGGAA<br>CAAACCGACGTGGAAT<br>CCTTTGCCGTGCTGGA<br>GCCCAAGGCAGATGGC<br>TTCCGAAACTACCTCG<br>GAAAGGGCAACCCGTT<br>GCCGGCCGAGTACATG<br>CTGCTCGACAAGGCGA<br>ACCTGC | 174 | 91.7 | As above |
| Mtb | isoniazid | **CGGCCGAGTACATGC**<br>TGCTCGACAAGGCGAA<br>CCTGCTTACGCTCAGT<br>GCCCCTGAGATGACGG<br>TGCTGGTAGGTGGCCT<br>GCGCGTCCTCGGCGCA<br>AACTACAAGCGCTTAC<br>CGCTGGGCGTGTTCAC | 175 | 89.4 | As above |

TABLE 3-continued

Exemplary regions for drug sensitivity testing of MTb

| Organism | Drug | Amplicon-Sensitive | SEQ ID NO | Design Tm | Reference |
|---|---|---|---|---|---|
| | | CGAGGCCTCCGAGTCA<br>CTGACCAACGACTTCT<br>TCGTGAACCTGCTCGA<br>CATGGGTATCACCTGG<br>GAGCC | | | |
| Mtb | isoniazid | **GGCAAGGATGGCAGT**<br>GGCAAGGTGAAGTGG<br>ACCGGCAGCCGCGTGG<br>ACCTGGTCTTCGGGTC<br>CAACTCGGAGTTGCGG<br>GCGCTTGTCGAGGTCT<br>ATGGCGCCGATGACGC<br>GCAGCCGAAGTTCGTG<br>CAGGACTTCGTCGCTG<br>CCTGGGACAAGGTGAT<br>GAACCTCGACAGGTTC<br>GACGTGC | 176 | 90.3 | As above |
| MTb | Ethambutol | **GGCGGGCATGTTTCT**<br>GGCTGTCTGGCTGCCG<br>CTGGACAACGGCCTTC<br>GGCCCGAGCCGATCAT<br>CGCC | 177 | 87.6 | ANTIMICROBIAL AGENTS AND CHEMOTHERAPY, February 2000, p. 326-336 Vol. 44, No. 2 |
| MTb | Ethambutol | **GGCGATGATTTCCCA**<br>**GT**ACCCGGCGTGGTCG<br>GTTGGCCGGTCTAACC<br>TACAGGCTTTGG | 178 | 82.2 | ANTIMICROBIAL AGENTS AND CHEMOTHERAPY, February 2000, p. 326-336 Vol. 44, No. 2 |
| MTb | ethambutol | **TCGGCGACAACCTCC**<br>GCGGCCCCGCATCCTC<br>ACCGCCCTTAACCGCG<br>TCGCCTACCATCGAGC<br>CTCGTGCCCCACGACG<br>GTAATGAGCGATCTCA<br>CCGGATCGCACGCCTA<br>GCAGCCGTCGTCTCGG<br>GAATCGCGGGTCTGCT<br>GCTGTGCGGCATCGTT<br>CCGCTGCTTCCGGTGA<br>ACCAAACCACCGCGAC<br>CATCTTCTGGCCGCAG<br>GGCAGCACCGCCGACG<br>GCAACATCACCCAGAT<br>CACCGCCCCTCTGGTA<br>TCCGGGGC | 179 | 92.9 | ANTIMICROBIAL AGENTS AND CHEMOTHERAPY, February 2000, p. 326-336 Vol. 44, No. 2 |
| MTb | ethambutol | **ACTCGGTTTATCACG**<br>**ACG**CCCGGCGCGCTCA<br>AGAAGGCCGTGATGCT<br>CCTCGGCGTGCTGGCG<br>GTCCTGGTAGCCATGG | 180 | 87.5 | ANTIMICROBIAL AGENTS AND CHEMOTHERAPY, February 2000, p. 326-336 Vol. 44, No. 2 |
| MTb | ethambutol | **GTATACATCGGTGCT**<br>**TGC**CCAGCTGGCGGCG<br>GTGAGCACCGCCGGCG<br>TCTGGATGCGCCTGCC<br>CGCCACCCTGGCCGGA<br>ATCGCCTGCTGGCTGA<br>TCGTCAGCCGTTTCGT<br>GCTGCGGCGGCTGGGA<br>CCGGGCCCGGGCGGGC<br>TGGCGTCCAACCGGGT<br>CGCTGTGTTCACCGCT<br>GGTGC | 181 | 94.7 | ANTIMICROBIAL AGENTS AND CHEMOTHERAPY, February 2000, p. 326-336 Vol. 44, No. 2 |
| MTb | ethambutol | **GCGACCGATGGACTG**<br>CTGGCGCCGCTGGCGG<br>TGCTGGCCGCGGCGTT<br>GTCGCTGATCACCGTG<br>GTGG | 182 | 89.6 | ANTIMICROBIAL AGENTS AND CHEMOTHERAPY, February 2000, p. 326-336 Vol. 44, No. 2 |

TABLE 3-continued

Exemplary regions for drug sensitivity testing of MTb

| Organism | Drug | Amplicon-Sensitive | SEQ ID NO | Design Tm | Reference |
|---|---|---|---|---|---|
| MMTb | ethambutol | **CGCCATCACCGACTC** CGCGGGCACCGCCGGA GGGAAGGGCCCGGTCG GGATCAACGGGTCGCA CGCGGCGCTGCCGTTC GGATTGGACCCGGCAC GTACCCCGGTGATGGG CAGCTACGGGGAGAAC AACCTGGCCGCCACGG CCACCTCGGCCTGGTA CCAGTTACCGCCCCGC AGCCCGGACCGGCCGC TGGTGGTGGTTTCCGC GGCCGGCGCCATCTGG TCCTACAAGGAGGACG GCGATTTCATCTACGG CCAGTCCCTGAAACTG CAGTGGGGCGTCACCG GCCCGGACGGCCGCAT CCAGCCACTGGGGCAG GTATTTCCGATCGACA TCGGACCGCAA | 183 | 94.8 | ANTIMICROBIAL AGENTS AND 94.8 CHEMOTHERAPY, February 2000, p. 326-336 Vol. 44, No. 2 |
| MMTb | ethambutol | **TTCGGCTTCCTGCTC** TGGCATGTCATCGGCG CGAATTCGTCGGACGA CGGCTACATCCTGGGC ATGGCCCGAGTCGCCG ACCACGCCGGCTACAT GTCCAACTATTTCCGC TGGTTCGGCAGCCCGG AGGATCCCTTCGGCTG GTATTACAACCTGCTG GCGCTGATGACCCATG TCAGCGACGCCAGTCT GTGGATGCGCCTGCCA GACCTGGCCGCCGGGC TAGTGTGCTGGCTGCT GCTGTCGCGTGAGGTG CTGCCCCGCCTCGGGC CGGCGGTGGAGGCCAG CAAACC | 184 | 92.9 | ANTIMICROBIAL AGENTS AND CHEMOTHERAPY, February 2000, p. 326-336 Vol. 44, No.2; |
| MTb | ethambutol | **TCAACAACGGCCTGC** GGCCGGAGGGCATCAT CGCGCTCGGCTCGCTG GTCACCTATGTGCTGA TCGAGCGGTCCAT | 185 | 87.5 | ANTIMICROBIAL AGENTS AND CHEMOTHERAPY, February 2000, p. 326-336 Vol. 44, No.2; |
| MMTb | ethambutol | **CACCGTCATCCTGAC** CGTGGTGTTCGCCGAC CAGACCCTGTCAACGG TGTTGGAAGCCACCAG GGTTCGCGCCAAAA | 186 | 85.4 | ANTIMICROBIAL AGENTS AND CHEMOTHERAPY, February 2000, p. 326-336 Vol. 44, No.2; |
| MTb | ethambutol | **GGCTGGTCCAACGTG** CGGGCGTTTGTCGGCG GCTGCGGACTGGCCGA CGACGTACTCGTCGAG CCTGATACCAATGC | 187 | 87.1 | ANTIMICROBIAL AGENTS AND CHEMOTHERAPY, February 2000, p. 326-336 Vol. 44, No.2; |
| Mtb | ethambutol | **TTCGCCCGAGCAAAG** ATGCCCGCCGATGCCG TCGCGGTCCGGGTGGT GGCCGAGGATCTGTCG CTGACACCGGAGGACT GGATCGCGGTGACCCC GCCGCGGGTACCGGAC CTGCGCTCACTGCAGG AATATGTGGGCTCGAC GCAGCCGGTGCTGCTG GACTGGGCGGTCGGTT TGGCCTTCCCGTGCCA GCAGCCGATGCTGCAC | 188 | 92.8 | ANTIMICROBIAL AGENTS AND CHEMOTHERAPY, February 2000, p. 326-336 Vol. 44, No.2; |

TABLE 3-continued

Exemplary regions for drug sensitivity testing of MTb

| Organism | Drug | Amplicon-Sensitive | SEQ ID NO | Design Tm | Reference |
|---|---|---|---|---|---|
| | | GCCAATGGCATCGCCG AAATCCCGAAGTTCCG CATCACACCGGACTAC TCGGCTAAGAAGCTGG ACACCGACACGTGGGA AGACGGCACTAACGG | | | |
| MTb | ethambutol | **ATGTCACGCTGCAAC** TGGTGCGGGTGGGCGA CCCGCGGGCATTCGGC TGCGTACCCACCGACG AGGAGGACCGCGTAGT CGCCTTTCTGGAGAAG ACGGAGGATC | 189 | 88.9 | ANTIMICROBIAL AGENTS AND CHEMOTHERAPY, February 2000, p. 326-336 Vol. 44, No.2; |
| MTb | ethambutol | **CGCGAACTGAACCAG** **A**TGGGCATTTGCCAGG CGGTGGTGCCGGTATC CGGACTTCTTGCGCTG ACCGCGCGCACACTGC GCCAGACCGAGTTCAT CGCGCTGCGCAAGCTG GCCGGTGCCGAGCGCA CCGAGCTCAATAGGGC CCTGCTGAGCGTGGAC CGTTTTGTGCGCCGGG ACAGTCCGCTACCGGT GGACGCGGGCATCCGT GCGCAATTGCTCGAGC GGTTCGGCATGTTCGG CATCCGGATGTCGATT GCCGTGCTGGCGGCCG GCGTGACCGATTCGAC CGGGCTGGCCGCCGAA CTGCTGGAGCGCAGCG GGCTGGTGGCGCTGCG CAATGTGATAGACCAG CAGTTCGCGCAGCGCT CCGACATGCTTAAGGC GCATACCGC | 190 | 93.9 | ANTIMICROBIAL AGENTS AND CHEMOTHERAPY, February 2000, p. 326-336 Vol. 44, No.2; |
| MTb | ethambutol | **GAGCAGGTGCTTTCC** **C**GCGCGACGGAGCGA GTGCGTGCTGGGGTAC TCGGCGAAATACGTTC GGCAACAGAG | 191 | 85.5 | ANTIMICROBIAL AGENTS AND CHEMOTHERAPY, February 2000, p. 326-336 Vol. 44, No.2; |
| MTb | ethambutol | **GGGTTCCTATGGCGG** CGTGGTCATGATTGGC ATGCTGTCGTCGGTGG TCGGACTTGGGTTGTT CAACC | 192 | 82.9 | ANTIMICROBIAL AGENTS AND CHEMOTHERAPY, February 2000, p. 326-336 Vol. 44, No.2; |
| MTb | ethambutol | **CGATCCCGATAGGTG** **TTT**GGCCGGCTTGCGG ATCAGACCCCGATTTC GGGGTGAGGCGGAATC CATAGCGTCGATGGCA CAGCGCCGGTCACGCC GGCGAACAGCTTCTTC GATTGAAGGGAAATGA AGATGACCTCGCTTAT CGATTACATCCTGAGC CTGTTCCGCAGCGAAG ACGCCGCCCGGTCGTT CGTTGCCGCTCCGGGA CGGGCCATGACCAGTG CCGGGCTGATCGATAT CGCGCCGCACCAAATC TCATCGGTGGCGGCCA ATGTGGTGCCGGGTCT GAATCTGGGTGCC | 193 | 93.2 | ANTIMICROBIAL AGENTS AND CHEMOTHERAPY, February 2000, p. 326-336 Vol. 44, No.2; |

TABLE 3-continued

Exemplary regions for drug sensitivity testing of MTb

| Organism | Drug | Amplicon-Sensitive | SEQ ID NO | Design Tm | Reference |
|---|---|---|---|---|---|
| MTb | ethambutol | **ATCACAGGAGTGGAGTT**TTGAACGCAACGACGGCAGGTGCTGTGCAATTCAACGTCTTAGGACCACTGGAACTAAACCTCCGGGGCACCAAACTGCCATTGGGAACGCCGAAACAACGTGCCGTGCTCGCCATGCTGTTGCTATCCCGGAACCAAGTCGTAGCGGCCGACGCACTGGTCCAGGCAATCTGGGAGAAGTCGCCACCTGCACGAGCCCGACGCACCGTCCACACGTACATTTGCAACCTTCGCCGGACCCTGAGCGATGCAGGCGTTGATTCGCGCAACATCTT | 194 | 92 | ANTIMICROBIAL AGENTS AND CHEMOTHERAPY, February 2000, p. 326-336 Vol. 44, No.2; |
| MTb | ethambutol | **TACGAACCACACGTTGC**GCAGACATCACACTAGACTACTTGTGTAACGGCGCCCTGTCGGGTAGCCAA | 195 | 83.6 | ANTIMICROBIAL AGENTS AND CHEMOTHERAPY, February 2000, p. 326-336 Vol. 44, No.2; |
| MTb | ethambutol | **GCTTGACGCCGCTAC**GGCACTGGCGCAGCGCACTGGCCACGGCGCTGGCAGCACCTGCGAACTCAACTTC | 196 | 90.5 | ANTIMICROBIAL AGENTS AND CHEMOTHERAPY, February 2000, p. 326-336 Vol. 44, No.2; |
| MTb | ethambutol | **CAGCCGATGCCGCTG**TCAAGGGCCACCGACCCGGTACATCGCACGGCGTGCCGAGATCCTGGGTTCTTACCGCATCGGCG | 197 | 90.2 | ANTIMICROBIAL AGENTS AND CHEMOTHERAPY, February 2000, p. 326-336 Vol. 44, No.2; |
| MTb | ethambutol | **ACAGCGCCAACGTCA**GCCGCCACCACGCCGTCATCGTCGACACGGGCACCAACTACGTCATCAACGACCTCCGATCGTC | 198 | 88.5 | ANTIMICROBIAL AGENTS AND CHEMOTHERAPY, February 2000, p. 326-336 Vol. 44, No.2; |
| MTb | Capreomycin/ Viomycin | **TCGCCGCTAGGCTGA**CCGCGTGTCAATCGTGACGCCATACGAGGACCTGCTGCGCTTCGTGCTCGAAACGGGTACGCCCAAATCCGACCGCACCGGCACCGGAACCCGCAGCCTGTTCGGCCAGCAGAT | 199 | 90.3 | ANTIMICROBIAL AGENTS AND CHEMOTHERAPY, August 2005, p. 3192-3197 Vol. 49, No. 8 |
| MTb | Capreomycin/ Viomycin | **CGGGTACGCCCAAAT**CCGACCGCACCGGCACCGGAACCCGCAGCCTGTTCGGCCAGCAGATGCGCTATGATTTGTCGGCCGGTTTCCCGCTGCTCACTACCAAGAAAGTCCATTTCAAATCGGTAGCCTACGAGCTGCTGTGGTTTTTGCGCGGCGATTCCAATATCGGTTGGCTGCACGAGCACGGAGTCACCATCTGG | 200 | 88.8 | ANTIMICROBIAL AGENTS AND CHEMOTHERAPY, August 2005, p. 3192-3197 Vol. 49, No. 8 |
| MTb | Capreomycin/ Viomycin | **ATTCCAATATCGGTTGGC**TGCACGAGCACGGAGTCACCATCTGGGACGAATGGGCAAGTGAT | 201 | 84.7 | ANTIMICROBIAL AGENTS AND CHEMOTHERAPY, August 2005, p. 3192- |

TABLE 3-continued

Exemplary regions for drug sensitivity testing of MTb

| Organism | Drug | Amplicon-Sensitive | SEQ ID NO | Design Tm | Reference |
|---|---|---|---|---|---|
| | | ACAGGCGAACTCGGGC CGATCTACGGTGTACA ATGGCGATCGTGG | | | 3197 Vol. 49, No. 8 |
| MTb | Capreomycin/ Viomycin | **GGTGAGCACATCGAC C**AGATCAGCGCGGCGC TGGATTTGCTGCGCAC CGATCCCGATTCCCGG CGCATCATCGTGTCGG CCTGGAACGTCGGCGA AATCGAGCGGATGGCG CTGCCGCCCTGTCATG CGTTCTTCCAGTTCTAC GTCGCCGATGGCCGGC TGAGCTGTCAGCTCTA CCAACGCAGCGCCGAC CTGTTTCTGGGTGTGC CGTTCAACATCGCCAG CTAT | 202 | 90.9 | ANTIMICROBIAL AGENTS AND CHEMOTHERAPY, August 2005, p. 3192-3197 Vol. 49, No. 8 |
| MTb | Capreomycin/ Viomycin | **CGCCGACCTGTTTCT GGGTGTGCCGTTCAA CATCGCCAGCTATGC GTTGCTCACCCACAT GATGGCCGCCCAGGC CGGCTTGTCGGTCGG CGAGTTCATCTGGAC CGGTGGCGACTGCCA CATCTACGACAATCA CGTCGAGCAAGTACG GCTGCAGCTCAGCCG CGAGCCGCGGCCATA TCCGAAACTACTTCT AGCCG** | 203 | 89.9 | ANTIMICROBIAL AGENTS AND CHEMOTHERAPY, August 2005, p. 3192-3197 Vol. 49, No. 8 |
| MTb | oxifloxacin Moxifloxacin/ Gatifloxacin/ Sitafloxacin/ Ofloxacin/ Levofloxacin/ Sparfioxacin) | **GCAACTACCACCCGC A**CGGCGACGCGTCGAT CTACGACAGCCTGGTG CGCATGGCCCAGCCCT GGTCGCTGCGCTAC | 204 | 88.3 | ANTIMICROBIAL AGENTS AND CHEMOTHERAPY, August 2005, p. 3192-3197 Vol. 49, No. 8 |

MTb—Mycobacterium tuberculosis

The co-amplified sequences of enriched MTb DNA and control MTb DNA are simultaneously denatured, and then annealed to produce homoduplexes of amplified control MTb DNA and enriched MTb DNA, and also produce heteroduplexes of the control and enriched MTb DNAs. A saturating double-stranded DNA binding dye, such as a dye that fluoresces when interacting with a duplexed nucleic acid, is included in the amplification mixture to enable the generation of high resolution melting curve data from these homoduplexes and heteroduplexes. As such, the annealed samples of homoduplexes and heteroduplexes as well as the control MTb DNA are subjected to high resolution melting curve analysis that is monitored using fluorescence or other methods of detecting the binding dye.

The data obtained from monitoring the high resolution melt of the homoduplexes, heteroduplexes, and control MTb DNA are input into a computing system to analyze the data. A mathematical comparison of the control MTb DNA sample data without added enriched sample DNA is then computed against the sample containing the co-amplified homoduplexes and heteroduplexes. The mathematical comparison, after normalization of the curves by temperature and beginning and ending points, allows the subtraction of each data point along the melting curve of the sample containing the co-amplified product from the control MTb DNA sample data. The resulting graph for invariant samples that have sequences that are not substantially different from the control MTb DNA is essentially a flat line with minor variation about zero. A graph for samples that have heteroduplex DNA (e.g., control DNA with enriched sample DNA) that contains base pairing mismatches will show a change in the melting curve, and when subjected to the subtraction algorithm will produce a distinctly different graph than the flat graph of control and invariant sequences.

Samples that contain variant graphs from the control sample graphs are scored as variant in the drug target region (e.g., nucleic acid target), and microorganisms are likely to be less susceptible (e.g., resistant) to the action of the drug for this genetic region. Also, several drug target nucleic acid regions can be amplified simultaneously in different reaction chambers for a single patient or for multiple patients.

In various aspects, the systems and methods enable rapid screening for suitable drugs for the treatment of individual cases of MTb. Using such an approach, a rapid personalized pharmaceutical regimen can be prescribed to a MTb patient, which can result in fewer drugs per patient, higher rates of compliance to treatment regimens, and/or an ultimate reduction in the rate of MDR-MTb generation.

II. Novel Primers

In some embodiments, methods are provided for improving the detection of nucleic acid sequences by utilizing rational oligonucleotide primer designs and rational target sequence designs in combination to produce narrow temperature ranges for both the annealing of primers with the target nucleic acid, amplification of the target nucleic acid, and denaturation of the amplified target nucleic acid product. As such, narrowed temperature ranges compared to the temperature range normally employed can result in an amplified target nucleic acid product that contains fewer nonspecific products. Thus, the amplified target nucleic acids products can be overall more specific and sensitive for quantitative PCR and genotyping target detection applications as described herein.

Rational design of oligonucleotide primers can include the selection via calculation, experiment, or computation of primers that have the desired melting temperature (Tm). The rational design can include selection of a specific primer sequences with the appropriate CG % to obtain the desired Tm. Also, the rational design can include modifications to the primers that include internucleotide modifications, base modifications, and nucleotide modifications.

In some embodiments, methods are provided for selecting primers for PCR that flank a variable sequence element of interest on a target nucleic acid. In some embodiments, primers are selected to have a Tm with the target nucleic acid (primer:target Tm) that is within a narrow range of the Tm of the target nucleic acid (target:target Tm). The specific, narrow temperature range used for such an amplification of the target nucleic acids is dependent on the melting profile of the target nucleic acid, and thereby the sequence of the target nucleic acid being amplified. As such, the narrow temperature range can be used as a target temperature range in order to identify and/or generate specific primers that have sufficiently high Tm values when hybridized with the target nucleic acid. Accordingly, the Tm values of the primers can be overlapping within the temperature range of annealing and/or denaturing of the target nucleic acid (see, FIG. 1).

Figure 2:
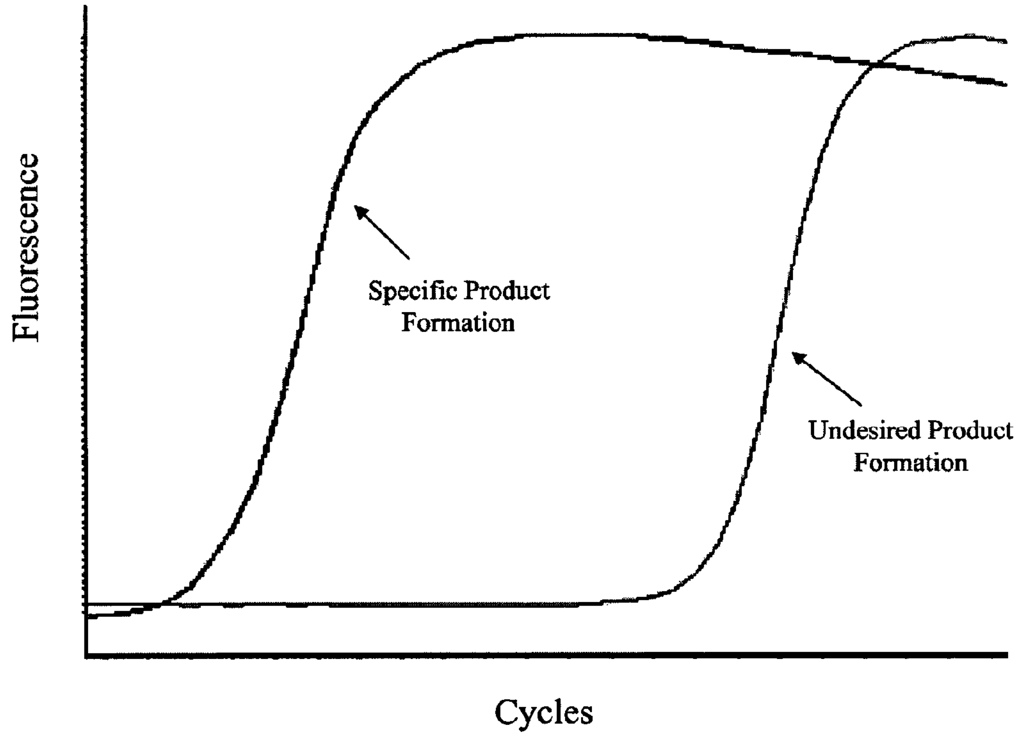
FIG. 2: An illustration of conventional amplification products by real time PCR.

FIG. 1 can be contrasted with FIG. 2 to illustrate the design of the primers to have the Tm within a range of the Tm of the target nucleic acid. FIG. 2 shows that conventional amplification with primers and a target nucleic acid are devoid of having a temperature overlap (as shown in FIG. 1) and require extreme temperature variations during amplification, corresponding to denaturation, annealing and extension cycles, to produce an amplified product. Such extreme temperature ranges allow for the formation of undesired products.

In some embodiments, an iterative design process is provided to select and/or optimize primers for specific target nucleic acid sequences to be amplified and/or detected. Advantageously, the iterative method enables the formation of a specific target nucleic acid by using a narrow range of thermal conditions where both the target nucleic acid and the oligonucleotide primers hybridized with the target nucleic acid are in a dynamic flux of annealing and denaturing. Such a dynamic flux of annealing and denaturing can result in a specific amplification of the target nucleic acid with a commensurate decrease in the formation of nonspecific amplification products.

The implications of such iterative methods for selecting and/or optimizing primers provides for the use of low cost dyes in lieu of more expensive custom oligonucleotide probes, such as those having fluorescent labels, can allow for quantitative PCR or high resolution denaturation to be used in analyzing the sequence of the target nucleic acid. Also, the iterative method can provide primers that function in the absence of exquisite thermally-controlled instruments for the formation of amplification products. That is, the primers can operate within a narrow temperature range in order to amplify the target nucleic acid, allowing nucleic acid amplification to be used in a much broader range of uses.

A number methods have been described in the art for calculating the theoretical Tm of DNA of known sequence, including, e.g., methods described by Rychlik and Rhoads, Nucleic Acids Res. 17:8543-8551 (1989); Sambrook, J. et al., Molecular Cloning: A Laboratory Manual, Cold Spring Harbor Laboratory Press, Cold Spring Harbor, N.Y. (1989); and Breslauer et al., Proc Natl Acad. Sci. 83: 3746-3750 (1986).

In some embodiments, primers can be configured to have a Tm with the target nucleic acid that is within a narrow range of the Tm of the target nucleic acid by chemically modifying the oligonucleotides. Well known oligonucleotide synthesis chemistries may be used to increase the Tm values of the primers so they correspond to the temperature range of the Tm of the target nucleic acid. Such chemistries may use modified bases (e.g., Super G, A, T, C), LNA, or PNA, or other such oligonucleotide stabilizing chemistries. Also, additional oligonucleotide hybridization stabilizing chemistries may be developed that can be used for this application.

For example, primers synthesized with both conventional phosphodiester linkage chemistry, and LNA chemistries have been used to provide primer Tm values close to the Tm values of the target nucleic acid sequence. However, it is possible that certain target nucleic acids may have Tm values lower than that of the primers, and a hybridization destabilizing chemistry may need to be included to decrease the primer Tm values so that the primer Tm value is within a range of the Tm values of the target nucleic acid sequence.

In some embodiments, methods are provided for refining the design of the primers to minimize the temperature range for the specific amplification of the target nucleic acid sequence. As such, the target nucleic acid is amplified with standard reaction thermal cycling conditions to ensure the target nucleic acid sequence is amplified. The amplification is monitored using real-time PCR with a double-stranded DNA binding dye, such as SYBR, LCGreen, LCGreen+, Eva dye, or the like. The amplified target nucleic acid is subjected to a melting curve analysis to determine the actual Tm value of the target nucleic acid sequence. The melting peak, which can be expressed as −dF/dT, is generated from melting the amplified target nucleic acid and can have a range similar to a distribution curve across a defined temperature range. At the low temperature end, the amplified target nucleic acid template is partially denatured. At the uppermost temperature the entire sample of amplified target nucleic acid is denatured. The temperature necessary to denature the target nucleic acid during the amplification procedure is within this temperature distribution. Initially, the uppermost temperature is recommended to ensure more complete denaturation. Subsequently, the lowermost temperature of the distribution curve can be used as the initial Tm for a set of designed primers for use in amplification before any iterative changes are made to the primers. Confirmation of the narrow temperature range that the initial primers may be used with can be performed either in serial or in parallel experiments of ever increasing annealing temperatures. Alternatively, the individual primers can be added to the amplified template and an additional melting curve analysis can be performed on the combined primer and template melting curves. In any event, the Tm of the primers can be configured to overlap with a narrow temperature range that contains the Tm of the target nucleic acid sequence.

The highest annealing temperature from these experiments where the target nucleic acid sequence is amplified specifically and efficiently can be considered the temperature which defines the optimal annealing temperature for the existing primers (e.g., primers that were tested). These same primers or slightly modified primers can then be re-synthesized with additional hybridization stabilizing chemistries. Modifications to the primers to change the Tm in the desired direction so that the primer Tm overlaps with a narrow temperature range that contains the Tm of the target nucleic acid sequence. This can be accomplished using online design tools, such as the LNA design tool available from Integrated DNA Technologies. Such design tools can be used to estimate the number of necessary LNA modifications required to raise the Tm of the primer to better overlap with the melting curve of the target nucleic acid sequence.

In the instance the primer Tm values are greater than the highest melting temperature of the target nucleic acid sequence, it may be necessary to redesign the primers to have a lower Tm. Alternatively, the quantity of divalent and/or monovalent cation salts or other destablizing agents (e.g., AgCl, DMSO, etc.) that are used in the amplification protocol (e.g., PCR) may be reduced to destabilize the hybridization of these oligonucleotides to the template. In any event, a reduction in the primer Tm may be needed in some instances.

Figure 3:
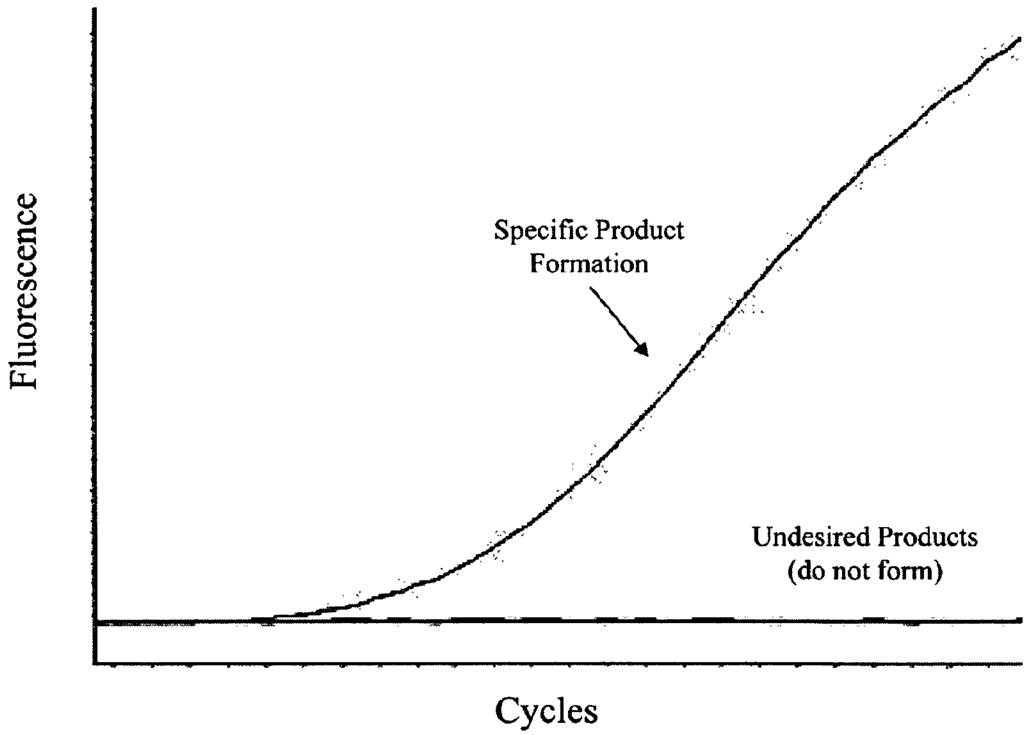
FIG. 3: A graph showing high temperature PCR amplification of the same template used in FIG. 2.

In some embodiments, the primers can be prepared so that the target nucleic acid amplification or enrichment protocols can be performed at minimized temperature differences during the thermal cycling. This allows the thermal cycling to be done within a narrow temperature range so as to promote the formation of a specific product. One range of thermal cycling can be within about 15° C. of the target nucleic acid Tm, more preferably within 10° C., even more preferably within 5° C., still more preferably within 2.5° C., and most preferably substantially the same Tm as that of the target nucleic acid Tm. For example, the thermal cycling conditions for the amplification of the target nucleic acid spans the range of the Tm peak +/− about 5 to 10° C. of the target nucleic acid sequence. Such narrow temperature ranges make it possible to amplify specific target nucleic acids without thermal cycling between temperatures corresponding to the normal stages of PCR amplification (denaturation, annealing and extension). Also, it makes it possible to perform amplifications and enrichments in commercial temperature-controlled instruments that can be set at selected temperatures or be varied within narrow temperature ranges, such as an oven, heating block, or the like. FIG. 3 illustrates the graph of a narrow temperature range PCR amplification with the same target nucleic acid sequence as shown in FIG. 2, which shows more specific product formation and less undesired products are formed.

In some embodiments, the temperatures of the thermocycling can be selected in a narrow temperature range to substantially limit amplification to amplifying the target nucleic acid sequence. As such, the thermal cycling conditions can be modified to amplify the target nucleic acid sequence by modifying the annealing temperature to be substantially the same as the lower temperature base of the melting peak for the amplicon. Also, the thermal cycling conditions can be modified to amplify the target nucleic acid sequence by modifying the annealing temperature to be substantially the same as the higher temperature base for the melting peak of the amplicon.

In some embodiments, the primer Tm can be selected so that the amplification of the target nucleic acid can be performed at a temperature that ranges between about 75 to about 90° C. Such a temperature range, or narrowed 5 to 10° C. range therein, can be used for the amplification of DNA and/or RNA target nucleic acid sequences to reduce the formation of non-specific products during the amplification (e.g., PCR) process.

In some embodiments, the primer Tm can be selected so that the amplification is performed at isothermal amplification conditions in the Tm range of the target nucleic acid sequence to ensure appropriate product formation.

In some embodiments, the present invention includes a method of designing a primer set having a Tm with a target nucleic acid that is within a narrow range from the Tm of the target nucleic acid sequence. As such, the primer set can be designed so that the primer Tm overlaps the distribution curve of the Tm of the target nucleic acid sequence. For example, the primer set can be used in real-time PCR assays so that the primer Tm overlaps the distribution curve of the Tm for the target nucleic acid sequence so that a narrow temperature range can be used to amplify the target nucleic acid sequence. For example, the primer can be designed so as to have a primer Tm that is within about 15° C. of the target nucleic acid Tm, more preferably within 10° C., even more preferably within 5° C., still more preferably within 2.5° C., and most preferably substantially the same Tm as that of the target nucleic acid Tm. Also, this can include primer Tm values that overlap with the amplicon Tm curve.

In some embodiments, the present invention includes an iterative process for designing primers. Such an iterative process can include identifying an initial target nucleic acid sequence as the target amplicon, wherein the target nucleic acid sequence can be associated with a particular biological activity, such as possible drug resistance. The target nucleic acid sequence is then amplified in order to produce an amplified product, and the Tm value of the amplified product (e.g., amplicon) is determined using conventional melting curve analysis. The melting curve analysis is then utilized to determine or compute new primers or primer sets for use in the amplification of the target nucleic acid. The determined or computed primers are then designed with primer Tm values within the range of the melting peak generated by the melt of the amplified product. The primers are then prepared or synthesized to have the designed primer Tm values.

In some embodiments, the conditions of the protocol for amplifying the target nucleic acid sequence can be modified to an appropriate pH to increase the specificity of selectively amplifying the target nucleic acid over other nucleic acids. As such, the use of an appropriate pH can increase the ability to selectively amplify the target nucleic acid sequence. This can include the use of an amplification buffer that can enable the activation of chemically inactivated thermal stable DNA polymerases. Also, adjusting the pH with selected amplification buffers can allow for the amplification protocol to be performed at reduced temperatures, such as those temperatures ranges that have been recited herein.

In some embodiments, the pH of the amplification buffer can be adjusted so as to allow for the conversion of a chemically inactivated enzyme to the activated state. As such, an enzyme may be activated in a slightly acidic condition; however, basic pH values may be used for some enzymes. For acid-activated enzymes, standard Tris-based PCR buffers can have significant temperature dependence (e.g., reducing by 0.028 pH units per degree C.). Complete activation of the enzyme (e.g., chemically inactivated thermal stable DNA polymerases) from the inactivated state of can require the pH to be less than about 7, more preferably less than about 6.75, and most preferably less than 6.5.

In some embodiments, the amplification protocol includes the use of lower pH buffers so that the amplification can be performed at lower activation temperatures. For example, for every 10° C. below 95° C., the enzyme activation temperature can be lowered by 0.3 pH units. However, limits to this approach are entirely a function of the dye chemistry used for the real-time detection of the amplified template (e.g., Fluorescein-based detection has significantly reduced fluorescence below pH 7.3).

In some embodiments, the primer Tm can be modified by altering the GC % of the primer sequence. By changing the GC %, the primer Tm can be selectively changed. Usually, increasing the GC % can increase the Tm, and decreasing the GC % can decrease the Tm. However, there are instances that a high GC % is desired that will overly increase the Tm. In such instances, destabilizers can be used to enable the inclusion of high GC % content primers or for the use of high GC % target nucleic acid sequences. The de-stabilizers can selectively decrease the temperature of the amplification procedure. Examples of destabilizers include DMSO, AgCl, and others.

In some embodiments, the design of the primers and/or amplification conditions can be modulated so as to modulate the size of the target nucleic acid sequence being amplified. This can include modulating the design of the primers and/or amplification conditions so that the size of the amplicon is significantly larger than that of the combined primers only. This can include the amplicon being 1-3 nucleotides longer than the primers, or 2 times larger than the primers, or 5 times larger than the primers, and more preferably 10 times larger than the primers.

Figure 4:
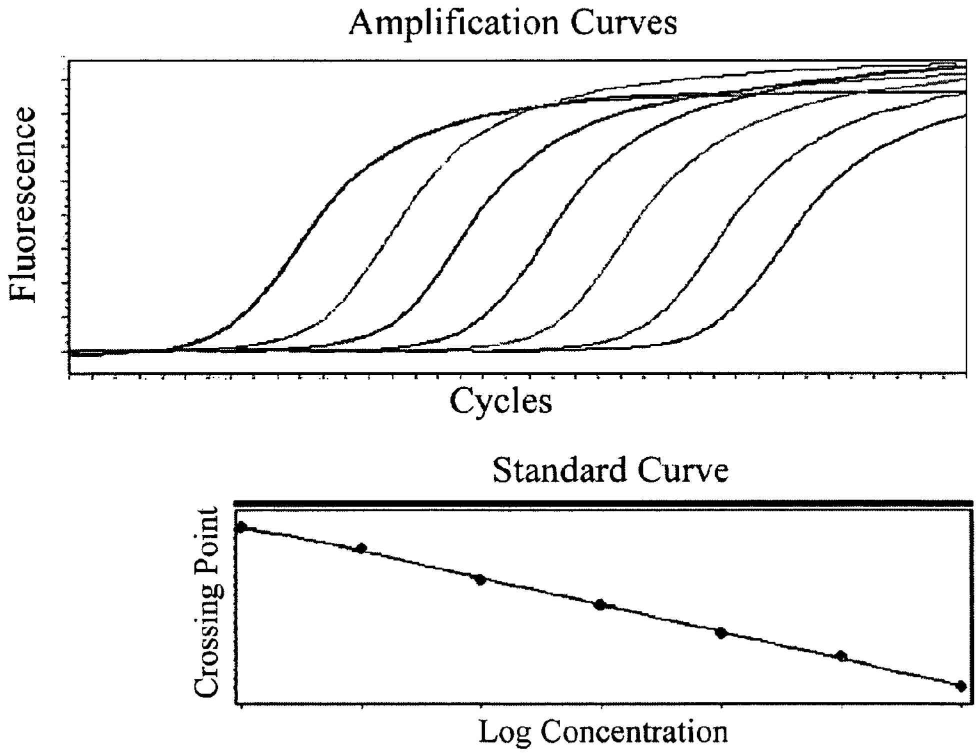
FIG. 4: Graph showing the HTPCR amplification of the same template material using different starting material concentrations

In some embodiments, the primers designed as described herein can be employed in an array of amplification procedures with different concentrations of starting material. That is, the starting material can be partitioned into an array at varying concentrations, and the primers can be used therewith for the narrow temperature amplification protocol as described herein. The use of the primers and narrow temperature amplification protocol with an array of varying concentrations of starting material can be used for quantification of the amount of target nucleic acid in the starting material. FIG. 4 is a graph that shows the use of the primers and protocol with an array of varying concentrations of starting material so that the amount of target material can be quantified.

III. Target Nucleic Acid Amplification/Enrichment

In some embodiments, methods provided herein include a step of amplifying or enriching the target nucleic acid. Such a method can include a procedure substantially similar to well-known methods of whole genome amplification and whole transcriptome amplification. This can include amplifying a genome with a genome library generation step, which can be followed by a library amplification step. Also, the library generating step can utilize the specific primers or mixtures of the specific primers described herein with a DNA polymerase or Reverse Transcriptase. The specific primer mixtures can be designed with the primers so as to eliminate ability to self-hybridize and/or hybridize to other primers within a mixture, but allow the primers to efficiently and frequently prime the target nucleic acid sequence, wherein the primers can be designed as described herein.

In some embodiments, methods are provided for simultaneously determining a genetic expression profile for an individual member of a species relative to an entire standard genome for the species. The methods can comprise distributing a liquid sample of genomic material into an array of reaction chambers of a substrate. The array can comprise a primer set and a probe for each target nucleic acid sequence along the entire standard genome. The liquid sample can comprise substantially all genetic material of the member. Each of the reaction chambers can comprise the primer set and the probe for at least one of the target nucleic acid sequences and a polymerase. The methods can further comprise amplifying the liquid sample in the array, detecting a signal emitted by at least one of the probes, and identifying the genetic expression profile in response to the signal.

Since the isolation of suitable quantities of microorganisms, such as MTb, from sputum samples can be a significant challenge, the genome amplification techniques described herein can be used instead of traditional culturing and purification protocols. Although many molecular diagnostic techniques enable the detection of very small quantities of starting genetic material (e.g., as low as a single copy of a target nucleic acid sequence), it is often difficult to ensure that a particular sample actually contains the desired single copy of the target nucleic acid sequence. To enable very rare or precious samples to be tested accurately in molecular diagnostic procedures, a technique known as whole genome amplification has been employed to enrich the starting material for use in the downstream molecular diagnostic procedures. The method described here applies the whole genome amplification method to the problem of MTb screening of sputum samples which often contain such low quantities of live organism. Otherwise, standard procedures may use isolates of MTb that must be grown for up to 2 months to ensure sufficient quantities of genetic material can be obtained from the sample for molecular diagnostic applications.

Using whole genome amplification techniques developed for the in vitro enrichment of rare and precious DNA and/or RNA samples, a novel genetic material enrichment method has been developed to enrich samples containing a microorganism DNA, such as MTb DNA. This technique enables the circumvention of conventional culturing methods that have heretofore been used to increase concentrations of microorganisms, which are often required for downstream molecular diagnostics. Such a whole genome amplification technique uses small quantities of genomic DNA from directly lysed microorganism samples. Samples containing live microorganism that have been isolated using the Petroff method can be directly lysed by a commercially available product, and the resulting small quantities of microorganism DNA can be subjected to the whole genome amplification techniques to provide an amplicon for use in downstream molecular diagnostic applications. While the procedure for employing the whole genome amplification technique is described with respect to MTb, it is recognized that such a technique can be applied to any microorganism.

Using a conventional live organism preparation method, the Petroff method, the isolated MTb is fractionated from the sputum sample leaving small quantities of the organism in a suspension of water. Following the protocol of the manufacturer of the mycobacterium lysis solution, MycoBuffer, (RAOGene; Milford, Pa.), small quantities of MTb DNA are isolated in the residual material from the MycoBuffer product. Using this directly lysed DNA sample and combining it with reaction ingredients similar to those used in whole genome amplification procedures enables molecular enrichment of the sample DNA. Such a procedure can provide increased quantities of the MTb genome, for example, in excess of 30 fold in less than 16 hours of incubation time. This level of sample enrichment can produce sufficient quantities of MTb genomic material to enable the use of this enriched material in downstream molecular diagnostic procedures in less than a day compared to current methods that may take more than 2 months of MTb culturing of the MTb isolates prior to diagnostic testing.

The whole genome amplification technique may be used with one or many DNA polymerases in order to improve the enrichment results either by reducing the time required for enrichment or by increasing the quantity of resultant enriched material. This can be used for amplifying RNA and/or DNA. Also, the amplification technique may be used with reverse transcriptase enzymes either alone or in combination with DNA polymerase enzymes to enrich samples for RNA components of the lysed material. Additionally, the amplification technique may be used with one or many different target nucleic acid priming parameters. Examples of the priming parameters that can be modulated include the following: the size primers; random primers; quantity of random primers; specific target primers; region specific primers; and combinations thereof. Modulation of such priming parameters can improve the whole genome amplification or specific region amplification within the samples. Further, the amplification technique may be used with various buffer mixes to improve the enrichment of the sample. Furthermore, the amplification technique may be used with various concentrations of nucleic acid building blocks, which may come from natural or synthetic sources. Further still, the amplification technique may be performed in any instrument capable of maintaining a constant temperature or varying temperature through a narrow temperature range (e.g., an instrument capable of maintaining a set temperature, either stably or with programmable thermal profiles). The reaction conditions can include some temperature variation within the temperature range during the enrichment process in order to improve the quantity of enriched genetic material or to specify the enrichment of specific regions of the genetic material, such as the target nucleic acid sequence.

For example, the sample genomic material may be isolated using any method that will release the microorganism (e.g., MTb) nucleic acids into solution or into a solid phase collector. The sample genomic material may be isolated from samples other than sputum, such as, but not limited to, blood, cerebral spinal fluid, skin lesions, organ lesions, or from environmental samples. The sample genomic material may be enriched using an enrichment method similar to whole genome amplification or nested PCR amplification. This can allow for regions surrounding the target nucleic acid sequence to be amplified using a thermal cycling method in combination with specific primers (e.g., primers having a Tm as described herein) to amplify the target nucleic acid sequence. Also, non-specific primers may be used to amplify the genome in a type of genome wide nested PCR.

*Mycobacterium tuberculosis* nucleic acid sample in the Mycobuffer solution can be prepared from the nucleic acid extraction protocol provided by the vendor or by any standard method. The nucleic acid may be either DNA or RNA from the microorganism sample to be enriched, where the nucleic acid can be intact, fragmented, or portions of the entire organisms nucleic acid. The enrichment mixture can include suitable DNA and/or RNA polymerase buffers, deoxynucleotide triphosphates, salts appropriate for the specific enzyme and buffer system, and random oligonucleotide primers. Examples of primer length can include 6 base, 11 base, and 22 base primers (Should we expand this?). The primers can be phosphodiester oligonucleotides, LNA oligonucleotides, PNA oligonucleotides, or any combination of thereof; however, future chemistries that can produce amplification or an enrichment of the interrogated target DNA or RNA are also expected to function properly in this technique. Also included in the mix may be a single-stranded DNA or RNA binding protein to improve the overall performance of the enrichment step.

An exemplary amplification technique can be performed as follows: the test sample target nucleic acids are combined in a suitable polymerization buffer with appropriate salts, with a random oligonucleotide primer (e.g., 6, 11, or 22 bases, or any of the primers or lengths of primers presented in Table 2), and the nucleic acids are denatured at a temperature high enough to ensure that denaturation is at least substantially complete, preferably complete; the denatured samples are maintained at near denaturing conditions, or in a temperature environment that will enable the target nucleic acid sequence of the sample to experience destabilized hybridization conditions; the samples are then cooled sufficiently to allow the primers to anneal to the target sequence, wherein the target sequence is contained within either the whole genome or fragments thereof; appropriate nucleic acid building blocks are added to the mix, which are either deoxynucleotide triphosphates, or ribonucleotide triphosphates, or possibly unnatural or artificial nucleic acid bases which can be incorporated with the products formed; appropriate enzymes (e.g., DNA polymerase, RNA polymerase, reverse transcriptase, any combination thereof, or the like) for the enrichment objectives are then combined; and the amplification is conducted at the narrow temperature in order to selectively amplify the target nucleic acid sequence.

IV. Screening Target Nucleic Acid to Determine Drug Resistance

In some embodiments, the amplified nucleic acids described herein can be employed in a method for screening the target nucleic acid sequence for the presence and/or absence of nucleic acid sequences or change in nucleic acid sequence indicative of drug resistance. That is, the amplified nucleic acids can be screened for a selected nucleic acid sequence by using high resolution denaturation in order to determine whether the microorganism may be drug resistant to a selected drug. As such, molecular diagnostics of nucleic acids can be used to detect genetic changes in target nucleic acid sequences, where changes in the sequence can be an indication that the microorganism is resistant to a drug. Accordingly, known genetic sequences that are altered in drug resistant strains can be analyzed to determine whether there are any such alterations in the gene sequences. Such genetic alterations are often indicative of altered susceptibility of the pathogen to treatment by drugs, which is often manifest by being drug resistant.

Typically, existing techniques require a foreknowledge of the specific mutations in the genetic nucleic acids that are related to drug targets (e.g., the nucleic acid is either the drug target or produces a gene product that is the drug target). This information is used to screen for drug resistance, and any changes in the pathogen's genetic material that is not being tested for specifically may be overlooked during the screening process. The method described herein does not require any foreknowledge of the specific changes. As such, a general region of the pathogen's genetic nucleic acids (e.g., DNA, RNA, etc.) is studied to see whether there are any variations in the sequence that is either the direct target of the drug or encodes for the direct target of the drug. Also, changes in the genetic material in such a region of the pathogen's genetic nucleic acids may render individual therapeutic drugs ineffective or reduce their efficacy. This technique allows the rapid identification of any genetic changes to drug target nucleic acid sequences, and can provide greater sensitivity in being capable of detecting expected as well as unexpected changes in the drug target nucleic acid sequences. Accordingly, the methods of the present invention can be used to generate drug sensitivity profiles of any particular microorganism isolate so that the likelihood of drug resistance can be established.

In some embodiments, the method of screening includes determining whether a specific microorganism is present in a sample. Also, the amount of the microorganism genetic material can be determined. Any positive samples are then processed herein in order to amplify the amount of genetic material. This can include combining the sample with primers or primer sets that hybridize with a target nucleic acid under conditions that amplify the target sequence. Also, the sample genetic material can be combined with a normal target nucleic acid sequence or a normal sequence probe (e.g., fluorescent or non-fluorescent) control that does not have any genetic variation so as to prepare a ratio of ~1:1, which is near equivalent test and control genetic material. However, it is possible to vary this ratio substantially, such as from 1:10 to 10:1.

The normal target nucleic acid sequence or normal probe sequence (e.g., control nucleic acid) are combined with the genetic material of the sample (e.g., sample nucleic acid), and then amplified in a single reaction tube. Alternatively the control nucleic acid and sample nucleic acid can be mixed after separate amplification procedures. A control nucleic acid of the normal target nucleic acid alone is also amplified simultaneously (however, with improvements to distinguishing individual strands of nucleic acids, it may be possible to run the control within the same reaction as the sample that is being interrogated). The denaturation profiles of the control nucleic acid and the sample nucleic acid can then be determined by high resolution melting curve analysis of the control and sample nucleic acids. Exemplary normal, or wild type, nucleic acid regions with known mutations that correspond to a change in drug resistance are listed in Table 3.

The denaturation profile data for these tests can be stored electronically. As such, the control or sample data may be retrieved from a previous analysis so that it can be used for a comparison of the results. The ability to save the denaturation profile data can eliminate the need to always perform a control reaction with each run of the test sample. The data for samples is compared data for the normal target control, and any differences or variations between the two data sets are scored as a variation in the target region for the unknown sample. When the sample includes a variation, the sample (i.e., microorganism) is classified as being potentially resistant to the drug that targets the genetic region (e.g., target nucleic acid sequence) that is the subject of the test.

In some embodiments, a sample target nucleic acid (e.g. DNA or RNA) is prepared with control target nucleic acid so as to obtain a mixture of sample and control target nucleic acid at about a 1:1 ratio. This can be achieved by mixing the sample and control nucleic acids, or co-amplifying the sample and control nucleic acids (e.g., by PCR) at about a 1:1 ratio of starting material. These sample and control nucleic acids are initially denatured at a temperature high enough to ensure the sample target nucleic acids and the normal control target nucleic acids are all denatured. The nucleic acids in the mixture (e.g., sample and control) are then annealed at some temperature below the melting temperature where they begin to denature (e.g., Tm). For example, the annealing temperature can be 10° C. or more below the Tm of the target control nucleic acid. The mixture is then subjected to slow heating, and the amount of hybridized sample and control nucleic acids present in the tube are monitored. The monitoring can be performed by fluorescence of the double-stranded nucleic acid product, wherein the fluorescence is generated by the inclusion of a dye which binds only to double-stranded nucleic acids. The dye can be included in an amount that saturates the template. The fluorescent signal is lost as the double-stranded nucleic acids begin to denature, and less sites are available for binding to the saturating dye. The denaturation procedure is continued until no double-stranded nucleic acid is present, and the fluorescence is nearly zero. The fluorescent data obtained during the denaturation procedure is then saved for computing and comparing against control denaturation data that is prepared with a similar protocol using only the control target nucleic acid. As such, a high resolution melting curve analysis can be performed with the mixture of the sample and control nucleic acids and the composition having only the control nucleic acids, and a comparison can be made between the two melting curves. A difference between the melting curves can be an indication that the sample nucleic acids are from a microorganism that has drug resistance to the drug that interacts with the target nucleic acid or gene product thereof.

In some embodiments, any protocol or instrument that can distinguish between the hybridized sample and control nucleic acids from the denatured sample and control nucleic acids can be used. The denaturation data obtained from the sample denaturation curves that were generated from the mixture having the sample and control nucleic acids are compared to denaturation data of the control nucleic acid. The denaturation data of the control nucleic acid can be either stored control denaturation data or the control nucleic acid can be denatured and monitored in a separate reaction chamber along with the experimental sample. The melting profiles of the normal control target are compared with the experimental sample so that any differences in these melting profiles can indicate the presence of a variation in the target region. When the control is a normal control target nucleic acid, variations in the sequences can indicate the microorganism is resistant to the drug that interacts with the target nucleic acid or gene product thereof.

In some embodiments, the co-amplified sequences of enriched MTb DNA and control MTb DNA are simultaneously denatured, and then annealed to produce homoduplexes of amplified control MTb DNA and enriched MTb DNA, and also produce heteroduplexes of the control and enriched MTb DNAs. A saturating double-stranded DNA binding dye, such as a dye that fluoresces when interacting with a duplexed nucleic acid, is included in the amplification mixture to enable the generation of high resolution melting curve data from these homoduplexes and heteroduplexes. As such, the annealed samples of homoduplexes and heteroduplexes as well as the control MTb DNA are subjected to high resolution melting curve analysis that is monitored using fluorescence or other method of detecting the binding dye.

The data obtained from monitoring the high resolution melt of the homoduplexes, heteroduplexes, and control MTb DNA are input into a computing system so that computing methods can be employed to analyze the data. A mathematical comparison of the control MTb DNA sample data without added enriched sample DNA is then computed against the sample containing the co-amplified homoduplexes and heteroduplexes. The mathematical comparison, after normalization of the curves by temperature and beginning and ending points, allows the subtraction of each data point along the melting curve of the sample containing the co-amplified product from the control MTb DNA sample data. The resulting graph for invariant samples that have sequences that are not substantially different from the control MTb DNA is essentially a flat line with minor variation about zero. A graph for samples that have heteroduplex DNA (e.g., control DNA with enriched sample DNA) that contains base pairing mismatches will show a change in the melting curve, and when subjected to the subtraction algorithm will produce a distinctly different graph than the flat graph of control and invariant sequences.

Samples that contain variant graphs from the control sample graphs are scored as variant in the drug target region (e.g., nucleic acid target), and microorganisms are likely to be less susceptible (e.g., resistant) to the action of the drug for this genetic region. Also, several drug target nucleic acid regions can be amplified simultaneously in different reaction chambers for a single patient or for multiple patients.

FIGS. 6A-6C provide illustrations that show results of methods of high resolution melting curve profiles for determining the presence of a variation in a sample target nucleic acid sequence from a normal target nucleic acid sequence. The presence of the variation is an indication that the microorganism is resistant to a drug, such as rifampicin. More particularly, FIG. 6A depicts the hybridization products, either by PCR amplification or alternative template enrichment method, of normal (e.g., non-resistant strains nucleic acids) and resistant strains. The normal template (e.g., control target nucleic acid) is included in the mixture with the sample target nucleic acid to produce an imperfect match between the nucleic acids that are hybridizing. FIG. 6B shows melting curves that have slight differences between the two melting curves, which are differences in melting profiles of the control target nucleic acid and the mixture with the sample target nucleic acid. FIG. 6C shows a difference in the melting curves between the control and the sample. The normal control target nucleic acid profile is plotted as the solid line sample, which has no difference from the "normal" nucleic acid of microorganisms that are sensitive to the drug. The dashed line shows a distinct difference between the "normal" and the mismatched sample, which indicates the microorganism is a resistant strain.

FIG. 7 is a graphical representation of high resolution melting curve analysis between +/− control nucleic acid, nucleic acids from a resistant strain, and nucleic acids from a strain that is sensitive to the drug. The graph was prepared using an automated curve difference calling software (Idaho Technology, LightScanner), and shows the ability to distinguish resistant samples from sensitive samples. Any sample which is called, by the software, as the same as the negative control is sensitive to the drug, and any sample called as different from the negative control is classified as resistant to the drug. The analysis package can be configured in any arrangement desired. Alternatively, any method that can graphically represent the difference between the shapes of the curves, especially in the upper region of the curve, can be used to differentiate between the 'normal' sequence and the test sequence potentially containing a mismatch. Further, the differences can be observed directly from the melting curves without further analysis.

In some embodiments, the high resolution melting curve analysis may be used in any genetic test for the detection of variation or similarities between sample nucleic acids and normal control nucleic acids.

In some embodiments, the amplification and/or denaturation can be used to screen for normal samples by using various altered probes instead of probes of a normal sequence.

In some embodiments, the amplification and/or denaturation can be to screen for mutated, non-normal, target nucleic acids using properly designed altered probes.

In some embodiments, the amplification and/or denaturation can be used for detecting commonalities between samples, such as forensic identification testing.

In some embodiments, the amplification and/or denaturation can be used for epidemiological surveying of different samples.

In some embodiments, the probes used in the amplification may be either DNA or RNA (e.g., natural, or synthetic, or from amplified sources).

In some embodiments, the amplification and/or denaturing can be used to confirm the presence of wild type sequences.

In some embodiments, the amplification and/or denaturing can be used to confirm the presence of wild type sequences to further demonstrate that the test sample comes from an organism that will be sensitive to the drug represented by that region.

In some embodiments, the amplification can be performed with real-time or conventional PCR methods. Also, any amplification method can be used that will produce sufficient quantities of normal control nucleic acids and/or target region genetic material to allow detection by an instrument with suitable detection capabilities.

In some embodiments, the denaturation or melting curve analysis detection system may be any high resolution melting instrument or an appropriately adapted instrument capable of generating sufficient resolution with basic sample heating and detection capabilities.

In some embodiments, the normal and sample nucleic acids can be amplified by PCR in a single tube. Alternatively, the normal and sample nucleic acids can be amplified in separate tubes and then mixed prior to the high resolution melting curve analysis.

In some embodiments, the normal nucleic acids may be retrieved from stock solutions, and then mixed with the amplified sample nucleic acids in appropriate ratios to generate similar results.

In some embodiments, the normal nucleic acids that are used as the control can be distinguished from mixtures with the sample nucleic acids by using a variety of chemistries in order to produce an internal control. This can include the use of different chemistries, such as using fluorescently labeled normal control nucleic acids. As such, only duplexes that are formed from the labeled control nucleic acids can generate a fluorescent melting signal, which is specific to the normal control template.

In some embodiments, the sample nucleic acids and the control nucleic acids may be compared after both the sample and control are amplified and/or denatured in different runs, which could be on different days.

In some embodiments, the high resolution melting curve analysis can be performed on any instrument capable of denaturing and/or annealing nucleic acids, and capable of detecting the amount of hybridized nucleic acids compared to the denatured nucleic acids.

In some embodiments, sufficient instrument sensitivity can allow for the analysis of the samples as described herein without having to amplify the sample nucleic acids. That is, the instrument has sufficient sensitivity so that the sample nucleic acids are detectable without amplification.

In some embodiments, the analysis of the sample nucleic acids is performed with high resolution annealing that monitors the nucleic acids as they anneal. In part, this is possible because the annealing of target nucleic acids of the sample and control can be used as the means to identify differences between the control template and the test samples rather than only using the melting curve analysis or denaturation.

In some embodiments, the present invention can study DNA and/or RNA from a microbiological or other biological sample for genetic variations. The nucleic acids can be intact, fragmented, or portions of the entire organism nucleic acid or the target region of the nucleic acid. The primers can be selected from a region of or adjacent to the portion of the target nucleic acid that is to be interrogated. The primers can be non-fluorescent, fluorescent, or capable of producing either an electrostatic or electrochemical signal.

The amplification compositions can include the following: polymerase chain reaction ingredients, include reverse transcriptase, and/or DNA polymerase; appropriate buffers, salts, and deoxynucleotide and/or deoxyribonucleotide triphosphates to amplify the target sequence; a fluorescent double-stranded DNA binding dye, fluorescent probe, fluorescence resonance energy transfer probes, or other similar probe may be used to detect the formation of the annealed versus the denatured RNA, or DNA/RNA homoduplex and/or heteroduplexes; oligonucleotide primers designed to specifically amplify the target region of the sample nucleic acid and the normal control nucleic acid, wherein the primers can be phosphodiester oligonucleotides, LNA oligonucleotides, PNA oligonucleotides, or any combination of these.

The instruments that can be used for the analysis of the sample nucleic acid can be any instrument capable of detecting the formation and dissolution of DNA/DNA, RNA/RNA, or DNA/RNA duplexes, and in further embodiments, DNA/protein or RNA/protein duplexes, or DNA homotriplexes// homoquadruplexes. Such an instrument should be capable of generating strong fluorescent signals when the targets are annealed and monitor the change in fluorescence as the target nucleic acids denature. The instrument data can be recorded in a computing system having software configured for performing data analysis. Also, the instrument can be configured to perform both the nucleic acid amplification and the hybridization/denaturation. However, it is possible to perform these functions in several distinct instruments without any detriment to the results. An alternate configuration would be an instrument that could monitor the annealed and denatured status of the target sequences by ultraviolet light, electrochemical signal generation, solution viscosity, or other as yet undeveloped techniques.

The data obtained from the analysis of amplification and the hybridization/denaturation can be analyzed with any software package configured to determine the differences between data. For example, a software package, currently available from Idaho Technology, or Corbett Research, and soon from Roche Applied Science, that is designed to compare the melting profiles of a normal target from those of the samples where the normal target is hybridized can be used to identify no changes, or minor or major differences. The exact format of the software output is unimportant; however, the software must simply be able to identify those samples which have variations from normal melting curve profiles compared to those that are normal.

The following Exemplary Aspects of specific aspects for carrying out the present invention are offered for illustrative purposes only, and are not intended to limit the scope of the present invention in any way.

EXEMPLARY ASPECTS

Example 1

Amplification and Analysis of Drug Sensitivity Regions of *Mycobacterium Tuberculosis*

A. Whole Genome Amplification of *M. tuberculosis* Genomic DNA

If sample DNA quantities are insufficient to obtain an amplified product from a drug sensitive region, then whole genome enrichment may be used to amplify the sample DNA before amplification of specific regions, or amplicons. The whole genome enrichment in the MycoBuffer sample was performed in the parallel with an identical starting copy number of template DNA that was suspended in water alone. To monitor the overall whole genome enrichment of the *mycobacterium tuberculosis,* 3 distinct target regions of the mycobacterium genome were chosen to evaluate each for enrichment. A real-time PCR assay method was used to screen each of these distinct target regions for enrichment compared to the un-enriched control samples. The point on the X-axis that the sample line begins to trend upward is indicative of the quantity of starting genetic material in the sample, the earlier on the X-axis that the signal begins to change the higher the quantity of starting material.

Figure 5A:
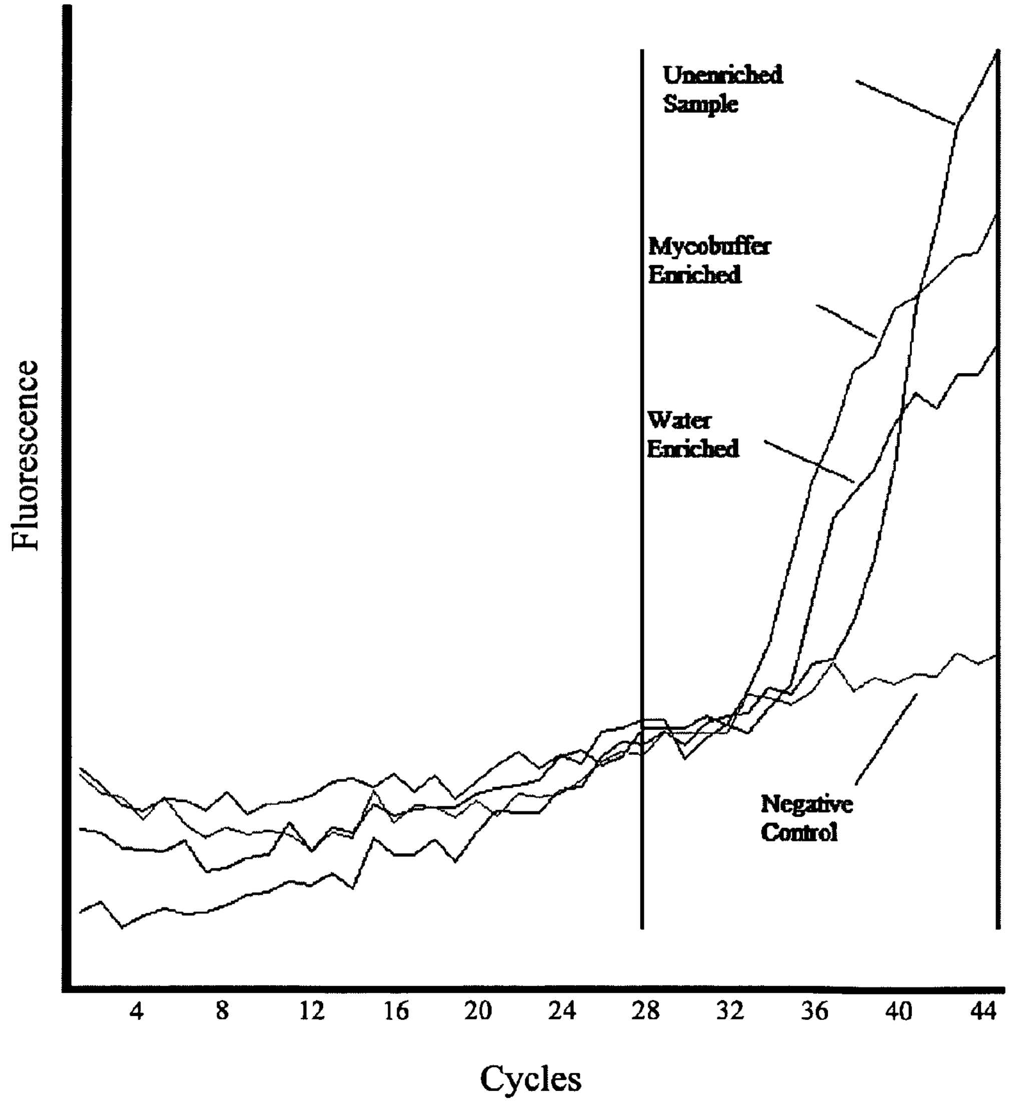
FIG. 5: A—Comparison of HTPCR products from the CFP32 gene of *M. tuberculosis* in water and MycoBuffer. B—Comparison of HTPCR products from the IS6110 gene region of *M. tuberculosis* in water and MycoBuffer. C—Comparison of HTPCR products from the btMTb gene region of *M. tuberculosis* in water and MycoBuffer. D—Comparison of HTPCR products from the IS6110 Transposase target gene region of *M. tuberculosis* in water and MycoBuffer. E—Comparison of HTPCR products from the BTTb gene region of *M. tuberculosis* in water and MycoBuffer.

FIG. 5A is a graph that shows the results obtained from the CFP32 target region of *Mycobacterium tuberculosis*, which compares the 22 base random primer mixed with samples in water or MycoBuffer. The graph shows the MycoBuffer enriched sample trends upwards earlier and indicates a higher amount of starting material.

Figure 5B:
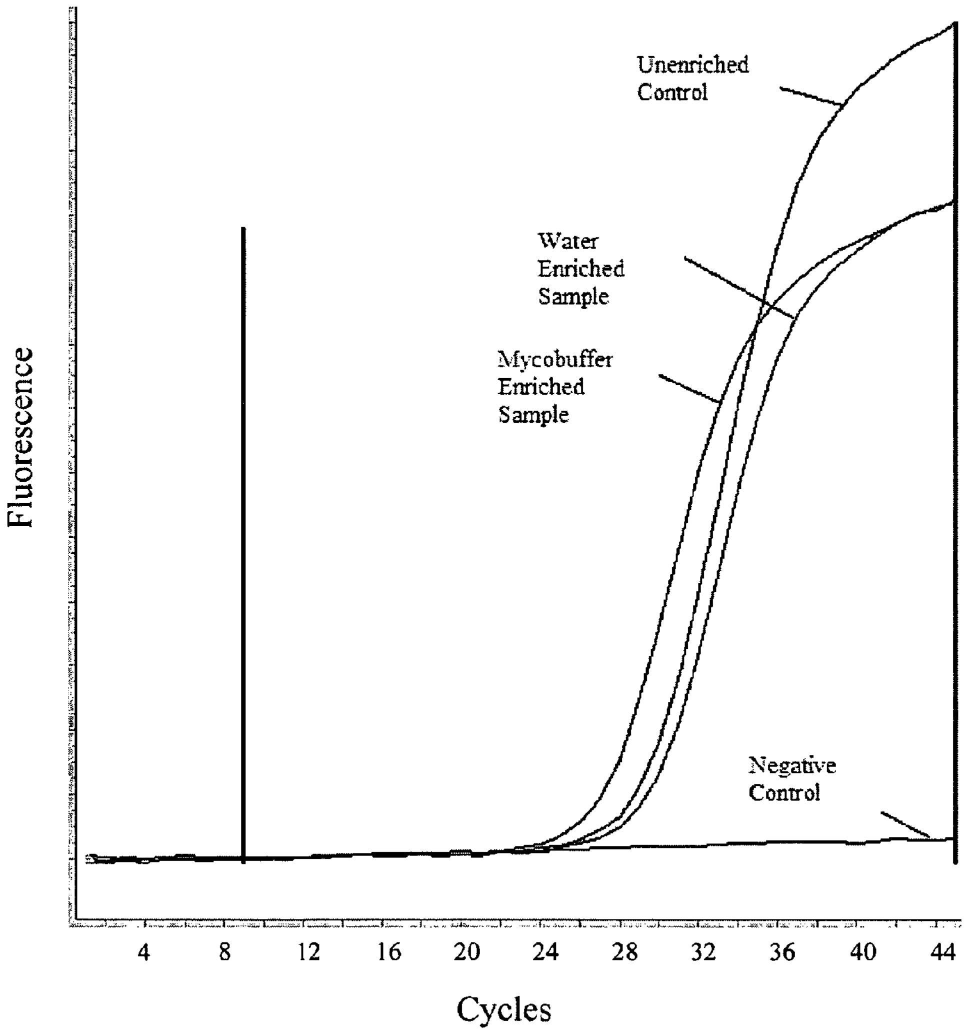

FIG. 5B is a graph that shows the results obtained from the IS6110 target region of *Mycobacterium tuberculosis*, which compares the 22 base random primer mixed with samples in water or MycoBuffer. Again, the graph shows the MycoBuffer enriched sample trends upwards earlier and indicates a higher amount of starting material.

Figure 5C:
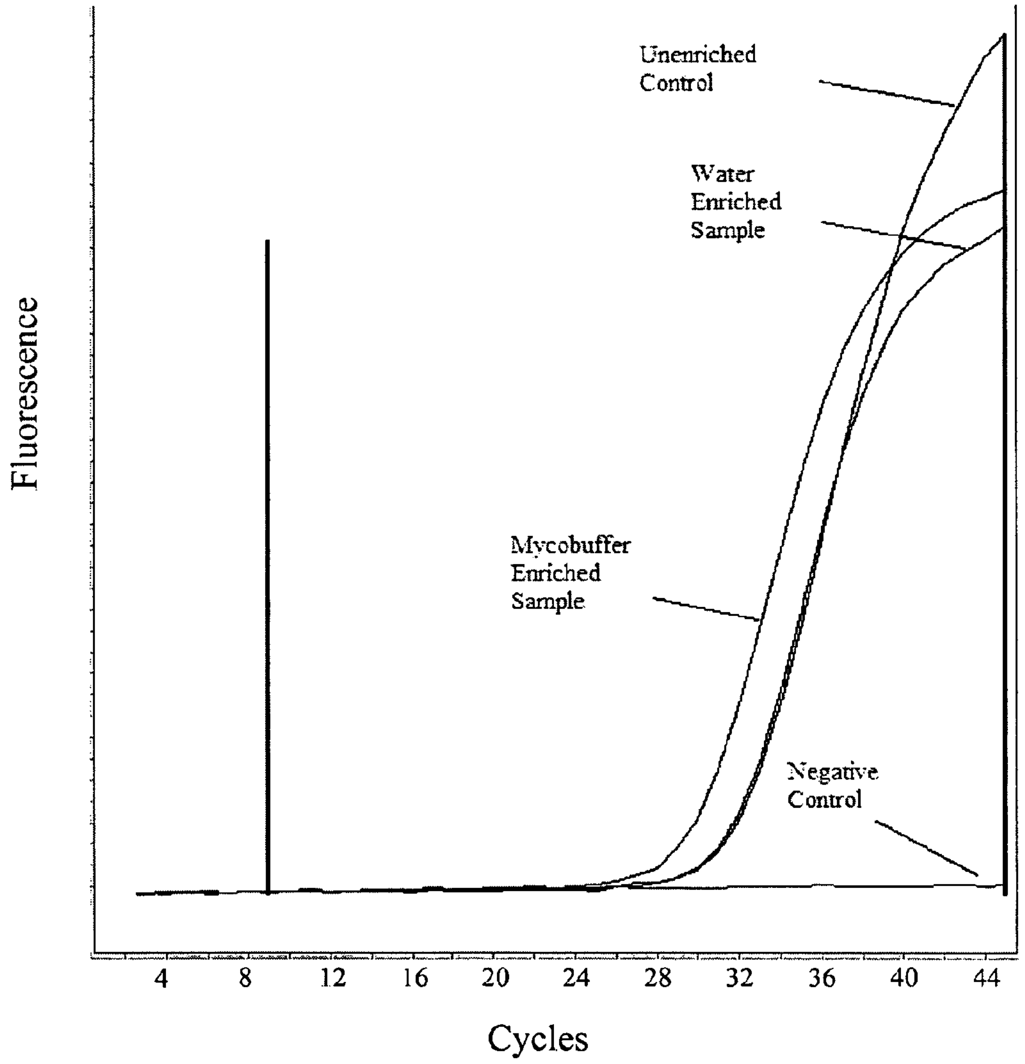
Figure 5D:
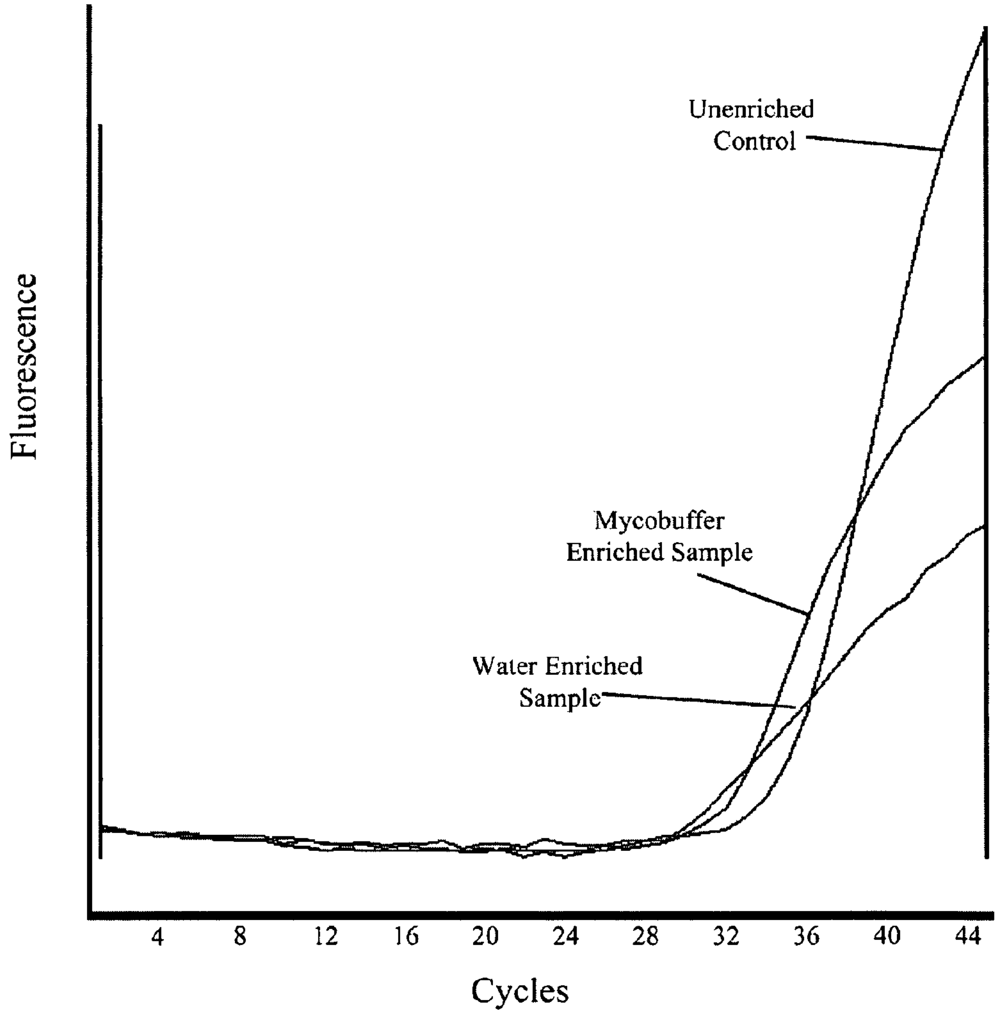
Figure 5E:
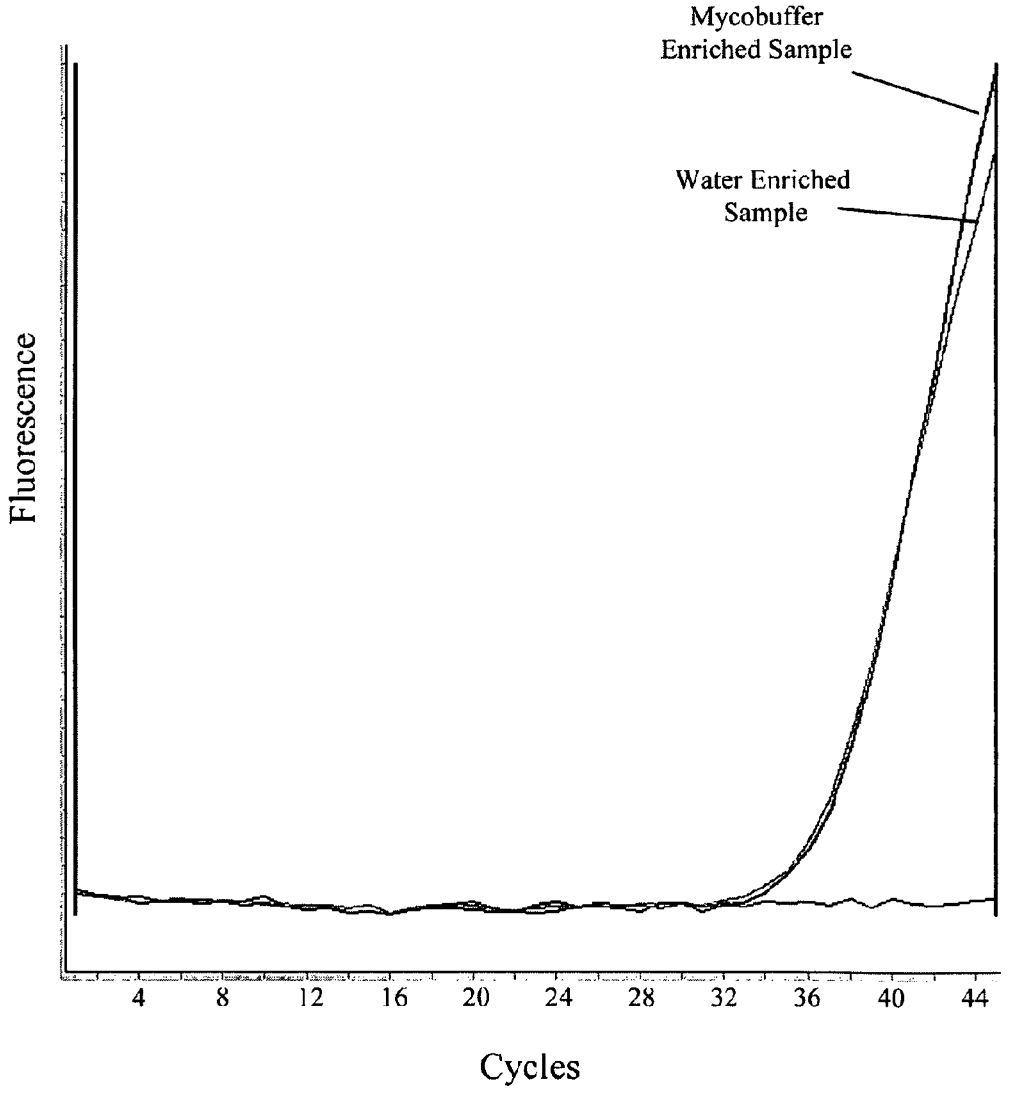

FIG. 5C is a graph that shows the results obtained from the btMTb target region of *Mycobacterium tuberculosis*, which compares the 22 base random primer mixed with samples in water or MycoBuffer. Yet again, the graph shows the MycoBuffer enriched sample trends upwards earlier and indicates a higher amount of starting material.

B. Sample Preparation

Using the Petroff method of sputum sample sterilization, MTb was separated from human cellular material. Briefly, the Petroff method is as follows: the Petroff method, sputum was homogenized for 15 min in a shaker by using an equal volume of 4% sodium hydroxide. After centrifugation at 3,000 rpm for 15 min in a Megafuge 1.0 (Heraeus), the deposit was neutralized with about 20 ml of sterile distilled water. Samples were again centrifuged. The 'deposit' or pelleted material is transferred to a microcentrifuge tube and lysed with Mycobuffer (RAOGene, Inc, Milford, Pa.) according to the manufacturer's instructions. The supernatant material from this lysis protocol contains the Mycobacterial DNA, and is transferred to a fresh microcentrifuge tube.

C. Primary Screen for the Presence of *M. tuberculosis* DNA in a Sample

Non-quantitative screening for Mycobacterial DNA in sample using the Fluoresentric MTb Screen (HTPCR method) was performed by combining the following ingredients in a 20 uL reaction, the products can be detected by real-time PCR with probes, or electrochemical detection, or by gel electrophoresis, or any other suitable method. Here we describe the use of real-time PCR to detect the product formation:

Combine:

10× FI15 Buffer: (500 mM Tris-HCl (pH 8.0); 5 mg/mL Bovine Serum Albumin (nonacetylated); 10 mM MgCl2, 40% Dimethylsulfoxide) use at 1× final concentration.

10× deoxynucleotide triphosphates (2 mM each) use at 1×.

10× LC Green I (Idaho Technology, Inc.) use at 0.5×.

Thermo-stable DNA polymerase (Tfi (exonuclease−) (Invitrogen Corp, Carlsbad, Calif.) use 2.5 U/reaction.

Oligonucleotide primers designed to have temperature overlap with the gene encoding the PPE Family Protein. Primers for amplified product:

```
                                     (SEQ ID NO. 205)
FI15-MTb FOR: CCGGAAACGTCGGCATCGCAAACTC

                                     (SEQ ID NO. 206)
FI15-MTb REV: TGCCCGTGTTGTAGAAGCCCGTGTTGAA
```

PPE Family gene

Add Mycobuffer/DNA sample to reaction.

Amplify according to the following protocol:

95 C denaturation: 1 min

75 C activation: 10 minutes 90 cycles of:

85 C for 30 s

75 C for 30 s with a fluorescent acquisition

1 Melt cycle:

95 C for 10 s

60 C for 10 s

Ramp to 95 C taking fluorescence acquisitions along the temperature ramp to generate a melting curve of the product.

Figure 8:
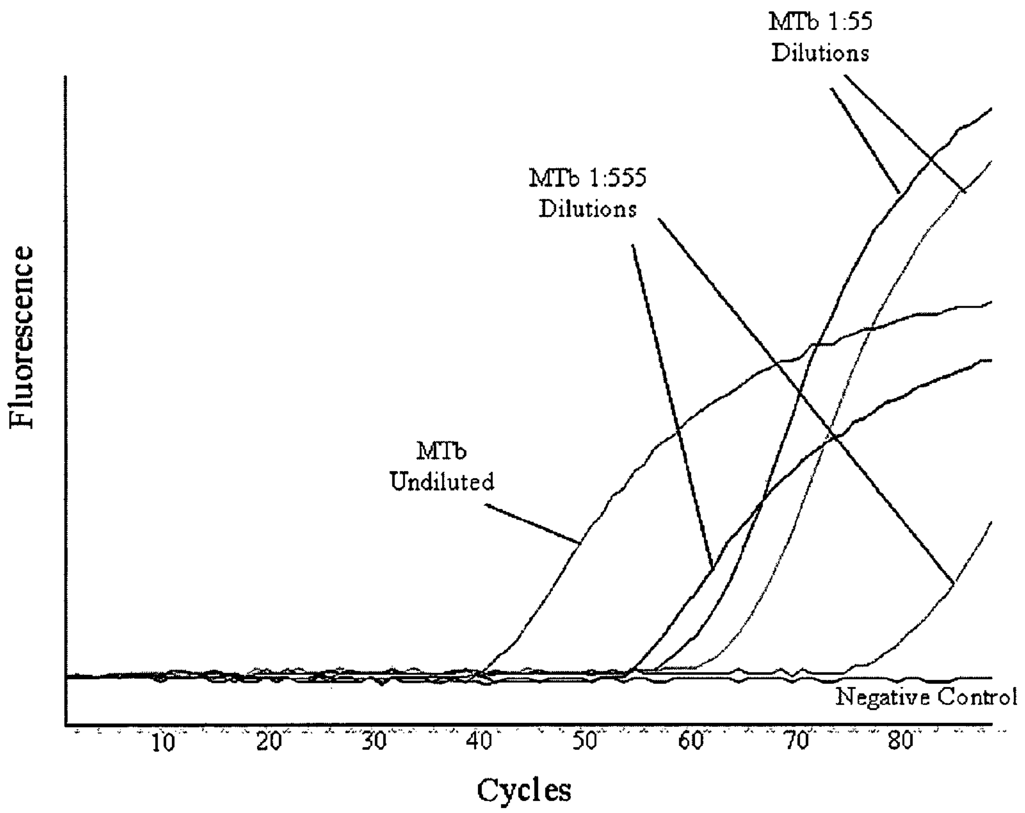
FIG. 8: Graphical representation showing different fluorescent curves for different nucleic acids.
Figure 9:
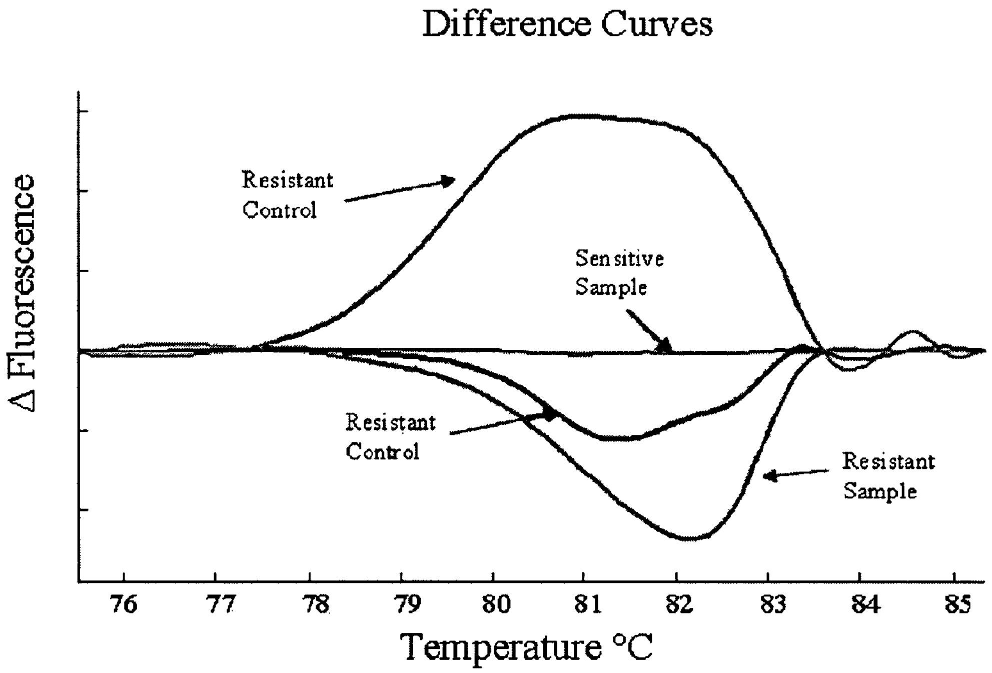
FIG. 9: Graphical representation of difference curve analysis between control, resistant and sensitive samples.

Final products may demonstrate variable melting profiles, as shown in FIG. 8. Those reactions that amplify a specific product are indicative of the presence of MTb DNA in a test sample.

D. Alternative Detection Method for Amplified Product

Alternative to real-time PCR detection: electrochemical detection

Using the same basic primers with the following addenda:

```
FI15-MTb FOR:
                                     (SEQ ID NO. 205)
Biotin-CCGGAAACGTCGGCATCGCAAACTC

FI15-MTb REV:
                                     (SEQ ID NO. 206)
Fluorescein-TGCCCGTGTTGTAGAAGCCCGTGTTGAA
```

Perform amplification as above. Remove sample and perform electrochemical detection according to manufacturer's directions (Anzenbio). Briefly, place in electrochemical detector chip (AnzenBio), incubate 20 minutes. The neutravidin chip binds to the biotin on the forward (or reverse primer . . . depending on the ultimate design) and the chip is washed with 1× Phosphate buffered saline+1% Tween 20 (PBST), 3 times. Add anti-fluorescein antibody conjugated to Horse Radish Peroxidase, incubate 20 minutes. Wash plate 3× with 1×PBST, add TMB (electrochemical detection buffer) and incubate 1 minute. Measure signal formation with PSD-8 detector. Signals in excess of 5 are scored as positive, those less than 5 are scored as negative. A reference negative sample, and positive sample should be included to confirm these results.

Alternative detection, the products can be visualized by gel electrophoresis, any product formation other than those seen in the negative control sample should be considered suspect of being positive for MTb.

Alternative detection, using capillary gel electrophoresis. Same as gel electrophoresis.

Alternative detection, HPLC, Mass Spectroscopy, Spectroscopy, Fluorimetry, and the like. Detection of the presence of an amplified PCR product in a sample can be achieved using any available techniques, preferably those that can differentiate amplified products by size as opposed to just quantity. The presence of an amplified product, especially one in the expected size range, is indicative of the presence of *Mycobacterium tuberculosis* (MTb) in a test sample.

E. Molecular Enrichment by Whole Genome Amplification

Molecular Enrichment Protocol:

Although most samples tested to date have had sufficient DNA for direct amplifications of target drug sensitivity regions, some samples of MTb DNA will contain very small quantities of DNA for use in the MTb Drug Resistance Screen. To overcome this problem a basic technique to enrich the samples using a modified whole genome amplification procedure has been employed. Basically, the samples are subjected to the following protocol:

DNA solution in Mycobuffer is added to random oligonucleotides. The solution is denatured and cooled to room temperature (allows random binding of oligonucleotides throughout the genome of the MTb). The solution is then mixed with whole genome amplification mixture and incubated for 8 hours to produce a whole genome enrichment, on average the genome is enriched 100× over the raw sample.

DNA incubation solution is:

1-5 uL of DNA

1× Thermopol buffer (New England Biolabs)

100 uM random 22-mer primers (final concentration).

In a total volume of 15 uL

Denature for 2 minutes at 96 C

Cool to Room Temp for 10 minutes

Place on ice

Add 35 uL of molecular enrichment mix (whole genome amplification mix)

Final concentrations of ingredients are:

400 uM dNTPs

1× Thermopol buffer 0.35 U/uL of BST thermo stable polymerase (*Bacillus stearothermophillus*) large fragment (exonuclease−)

4% Dimethyl sulfoxide

T4 gene 32 protein (30 ng/ul)

Incubate 8 hrs @ 50 C

Incubate 15 minutes @ 80 C

Hold at 4 C until use.

Samples are then purified by a modified filter binding assay. Briefly, this method can be employed at any stage in the process where DNA is to be separated from the solution . . . a quick method to buffer and primer exchange the DNA. We have found the Direct binding of the Mycobuffer solution+Binding Mix works well for earlier stage purification is needed or desired.

Sample DNA in Mycobuffer is mixed 1:1 with Binding Mix (4M Guanidinium HCl, 12.5 mM Tris-HCl, pH 6.8, 0.5% NP40 detergent, 50% Ethanol)

Samples are loaded onto a Whatman GF/F 1.0 um glass fiber filter 96 well long drip filter plate, and incubated at room temperature for 2 minutes. The filter plate is stacked on a 96×2 mL waste collection plate.

Samples are centrifuged (1800 rpm for 10 minutes) or vacuum filtered (slowly), remove plates from centrifuge or vacuum system.

200 uL of Wash Buffer I (1.6 M Guanidinium HCl, 10 mM Tris-HCl, pH 6.8, and 0.1% NP40, 70% Ethanol) is added and centrifuged or vacuum filtered. Plates are removed from centrifuge or vacuum system.

400 uL of Wash Buffer II (50 mM NaCl, 10 mM Tris-HCl, pH 7.5, 60% Ethanol) is centrifuged or vacuumed. Followed by a second wash with 200 uL Wash Buffer II, Collection reservoir is emptied, and entire system is either vacuum dried or dried by air, at RT for 2 hrs, or at 56 C for 20 minutes.

A fresh collection plate is stacked with filter plate, and 100 uL of Elution Buffer (DNase, RNase Free sterile water) is added to the filters. Samples incubate at RT for 2 minutes, and are centrifuged, or vacuum filtered.

This entire system is a modification of existing methods using these 96 well filter plates.

Sample DNA is in the eluate. Alternatively, the amplified genome products can be used directly without purification for further amplification procedures if the genomic reaction contents and random primers don't interfere with subsequent specific amplifications.

This material is used for downstream processes.

The sample DNA is then evaluated with QPCR to confirm the amount of DNA present in the sample. This serves three purposes: 1 is to perform a secondary screen for the presence of MTb in the sample; 2 is to verify the molecular enrichment; and 3 is to establish an overall quantification of the amount of DNA present in the sample. This method as previously developed has demonstrated a consistency of enrichment of no more than 3 fold variation in the enriched sample DNA. Our method uses three genes to confirm the enrichment. One gene result is used for additional downstream processing.

F. Real Time Amplification of Samples Containing *M. tuberculosis* DNA

Each sample is subjected to real-time PCR quantification of the enriched sample DNA. Using a fluorogenic probe system (5' nuclease assay, TaqMan) as the signal generating moiety.

The reaction components are as follow:

Reaction mix:

10×PCR buffer (500 mM Tris-HCl, pH 8.5, 5 mg/ml BSA (non-acetylated), 40 mM MgCl2)

10× dNTP 2 mM Each (also may use 4 mM dUTP for contamination clean up purposes) Enzyme (Thermostable DNA Polymerase) Tfi exonuclease+(invitrogen, Carlsbad, Calif.)

And oligonucleotide primers (three different reactions possible per sample), use primers at 0.5 uM final, and fluorogenic probes at 0.2 uM Final.

Pan *Mycobacterium* Assay: MTb27.3 (conserved protein):

```
                                      (SEQ ID NO. 207)
CFP32 FOR: TCGTTCATCACCGATCC

                                      (SEQ ID NO. 208)
CFP32 REV: GTGAGCAGTTCGTTCCA

                                      (SEQ ID NO. 209)
CFP32 TM: FLUORESCEIN-TCAACGAGACGGGCACGCT-BHQ1
```

IS6110 Transposase:

```
IS6110 FOR;
                                      (SEQ ID NO. 210)
TGCGAGCGTAGGCGTC

IS6110 REV:
                                      (SEQ ID NO. 211)
GTCCAGCGCCGCTTC

IS6110 TM;
                                      (SEQ ID NO. 212)
FLUORESCEIN-CTGCTACCCACAGCCGGTTAGGT-BHQ1
```

PPE Family Protein Gene:

```
                                      (SEQ ID NO. 213)
BTTb FOR;    GCCAGCATTGAGGAT

                                      (SEQ ID NO. 214)
BTTb REV;    CAATTCGGGCACCAATAA

                                      (SEQ ID NO. 215)
BTTb TM;     FLUORESCEIN-TGCGATGCCGACGTTTCCG-BHQ1
```

IS6110 is a target that is not reliable for quantification as it is present in the genome of MTb>1/genome.

BTTb and cfp32 genes are used for establishing enrichment in the assay, both have similar signal crossing values at cycle 34, versus the unenriched samples which are either "flat" for BTTb or are 100× (>6 cycles) later than the enriched sample (cfp32).

Each reaction has 1-5 uL of purified or prepared DNA solution added to the final reaction mix. The volume information must be noted in the reaction setup, as the exact volume will become a numerical divisor for downstream processing. It is important to determine the relative quantity of MTb DNA in a sample for subsequent mixing steps.

Amplification and Melting Analysis of MTb DNA Sample and Controls

The enriched sample DNA is then analyzed with the drug sensitivity marker assays. This assay is based on the following information: hybridized DNA which is perfectly matched by Watson/Crick base pairing rules will generate a characteristic melting curve of the melting DNA. When the same sequence is hybridized with a similar sequence of DNA that contains 1 or more 'mis-matched' bases along the length, the characteristic melting curve is no longer generated, but rather a new curve is generated that indicates the difference in the melting characteristics for the mismatched strands of DNA. To generate the mismatched sequences it is not simply sufficient to use the amplified DNA for the sample in question, rather it is necessary to also include a sample of DNA that contains a sequence of DNA that is the 'unmodified' DNA. Such that, when the two are mixed in nearly equal proportions prior to, during, or at the end of an amplification reaction, and they are hybridized together a significant percentage of the hybridized templates are in 'mis-matched' hybridizations. Such that a melting curve can be generated that will indicate the presence of a 'mutation' in the sample sequence. If these sample sequences that are being amplified are designed to surround the nucleic acid sequences of genes that are either themselves or their gene products are the target of antimicrobial drugs. Then any aberrant melting behavior from the samples will make suspect the use of a particular drug for the treatment of the microbiological infection as the organisms DNA will indicate, or at least suggest, that the drug will be ineffective. This may potentially be applied to cancer chemotherapy, viral drug resistance, and antimicrobial drugs.

The process for performing this screen is as follows. Using the results from the three secondary screens for MTb following molecular enrichment of the samples, the results from the Cfp32 sample are used to calculate the amount of DNA present in the sample. Alternatively, any MTb amplicon can be used to determine the quantity of DNA in the MTb sample relative to control DNA as long as the amplicon is present in both. Further, separate control and unknown amplicons could be assessed for determining the relative DNA concentrations in control and test samples. Our purpose for using only one has been for ease of calculation.

The calculated crossing threshold from the Roche LightCycler 480 instrument, or virtually any real-time PCR machine, is used to calculate the concentration of 'wild-type' RPOB (Rifampicin) drug target to add to the screening reaction. The control stock solution (1:1,000,000 dilution of master stock) is diluted 10× for every 4 cycles that the sample crosses baseline after cycle 18, in the case of the example above with a CT value of 32, this is 14 cycles or a 5000× dilution (10^3.69). This can be easily presented as a chart for the user or as a simple piece of software that will calculate the volumes to be mixed prior to amplification and/or melting.

The sample DNA and an equal amount of RPOB 'normal, wild type, unmutated, non-resistant DNA' is added to the reaction. The reaction consists of the following components:

10×PCR buffer (500 mM Tris-HCl, pH 8.5, 5 mg/ml BSA, 30 mM MgCl2)

10×dNTP mix (No dUTPs)

Oligonucleotides at 0.5 uM (final) each

LCGreen+ or LCGreen Dye (Idaho Technology, Inc)

Enzyme (Tfi (exo+)) or other thermostable polymerase with proofreading activity.

*Mycobacterium* RpoB gene, target of Rifampicin (Antibiotic):

```
RPOB FOR: CAAGGAGTTCTTCG-        (SEQ ID NO. 13)
GCACC

RPOB REV: GGACCTCCAGCCCGGCA      (SEQ ID NO. 14)
```

A control reaction with only the RPOB sample as well as 1,2 or more 'resistant' controls can and should also be performed simultaneously, in separate reactions. We have two control reactions where we have mixed in equal proportions the RPOB normal control with one of the following: 1 a single point mutation in the target region, or 2 a 3 base deletion of the target region. These three samples serve to ensure the assay is performing as expected, controls for each drug target should be included and would essentially have similar characteristics.

The samples are amplified by the following protocol, on a LightCycler 480 instrument.

95 C for 10 minutes 40 cycles of:

95 C for 10 s

57 C for 10 s

72 C for 40 s

1 Cycle of Melting:

95 C for 10 s

50 C for 10 s

70 C for 30 s

95 C for 0 s with fluorescence acquisitions set to 25-35 acquisitions/degree C. (High Resolution melting). The data can then be analyzed using the soon to be released High Resolution Melting curve module for the LC 480 instrument or by using the LightScanner software from (Idaho Technology, Inc.). Both packages allow one to set the baseline samples (the positive control samples, as standards). Further, any device that can measure the quantity of double stranded DNA (dsDNA) at specific temperatures during the melting can be used to generate melting curves. The default curve settings are usually sufficient, though occasionally the settings must be modified to be sure that the control samples are being accurately called. If control samples are accurately called then the reaction results can be deemed acceptable and the diagnostic call can be made. Thus, a difference between the control wild-type melting curve and a melting curve from an unknown sample is indicative of a point mutation or polymorphism between the samples. In this case, with the rpoB region of MTb, the difference between melting curves is indicative of the presence of Rifampicin resistant DNA in a test sample, and thus can be used to diagnose the presence of Rifampicin resistant MTb in a sample. In a similar manner, this technique can be applied to analyze any DNA region where there are known mutations that correlate with a change in a phenotype, and is especially powerful for the assessment of drug resistance or sensitivity.

Example 2

Determination of Drug Resistance or Sensitivity in Human MTb Samples

The purpose of these experiments was to demonstrate that clinical samples previously tested and confirmed to contain MTb could be rapidly assessed for drug resistance or sensitivity. Blinded clinical samples from MTb patients were obtained that had been prepared by the Petroff method and were resuspended in MGIT buffer (Becton Dickinson). Samples were assessed for Rifampicin and Streptomycin resistance using primer pairs, amplicons and melting temperatures listed in Tables 2 and 3.

MTb test protocol:

Run samples against H37RV standard sample using cfp32 Taqman assay to quantitate samples.

Mastermix: 1× Kappa without Sybr buffer (Kappa Biosystems SYBRG1 master mix without SYBR), 1 ul cfp32 oligo, 1.75 mM MgCl, QS to 9 ul with water Place 18 ul of mastermix per sample into 384 well plate.

Add 2 ul of samples.

Place a plate seal on plate and spin plate

Run in LC480 under cfp32 run protocol.

Denature 10 min at 95 C

Amplify: 95 C for 10 sec, 59 C for 40 sec (50 cycles)

From cfp32 assay determine dilution factor needed for samples using the equation C=S*E^N where

C=10000000

E=Standard curve efficiency

N=Cp value

Dilute samples to lowest concentration sample in Myco buffer.

Run diluted samples in 80 bp rpob assay to determine resistance.

Mastermix: 1× Kappa without Sybr, 0.5 ul 80 bp Oligo, 1× Eva green dye, QS to 9 ul with water Place 9 ul of mastermix per sample into 384 well plate.

Add samples 0.5 ul of H37RV+0.5 ul of samples into well.

Place a plate seal on plate and spin down

Run in LC480 under rpob run protocol.

Denature: 10 min at 95 C amplification: 95 C for 10 sec

57 C for 10 sec

72 C for 40 sec with single acquisition

Run samples until all samples have reached plateau for 2 or 3 cycles (approx. 30 cycles).

End amplification protocol and all samples to go through melting protocol.

Remove plate from LC480 and centrifuge to collect any condensation from top.

Melting protocol ramp to 95 C for 1 sec

50 C for 1 sec

70 C for 30 sec Start collecting melt data continuously at 30 acquisitions/degree C.

End data collection at 95 C

Melt samples on HR-1 instrument.

Move samples from 384 well plate to 20 ul capillary tubes.

Briefly spin labelled capillaries in centrifuge to collect samples at bottom.

Using HR-1 instrument control software, melt samples individually using the FI LAB MTb Opt Melt protocol.

Ramp rate 0.07 acquisition start at 80 C with target Fluorescence of 90%

End acquisition at 96 C

Cool to 40 C

Note: Run 2 samples prior to data collection to allow instrument to warm up properly.

Data Analysis

Open up HR-1 Melt Analysis tool software.

Open folder containing data files and click "select current directory"

Select samples to analyze and click "continue"

Under "analyze" select normalize

Adjust left two cursors to approximately one degree before melt begins

Adjust left two cursors to approximately one degree after melt ends

Click OK

Under "Analyze" select temperature shift.

Under samples select a wild type sample to standardize to.

Adjust cursors to magnify melt region.

Select OK

Under "Analyze" select difference plot

Select wild type sample to standardize to.

Move cursors to select region of interest click OK

Samples showing peaks on a curve difference plot above or below a fluorescence level of 1.5 to 2 is considered resistant.

Figure 10A:
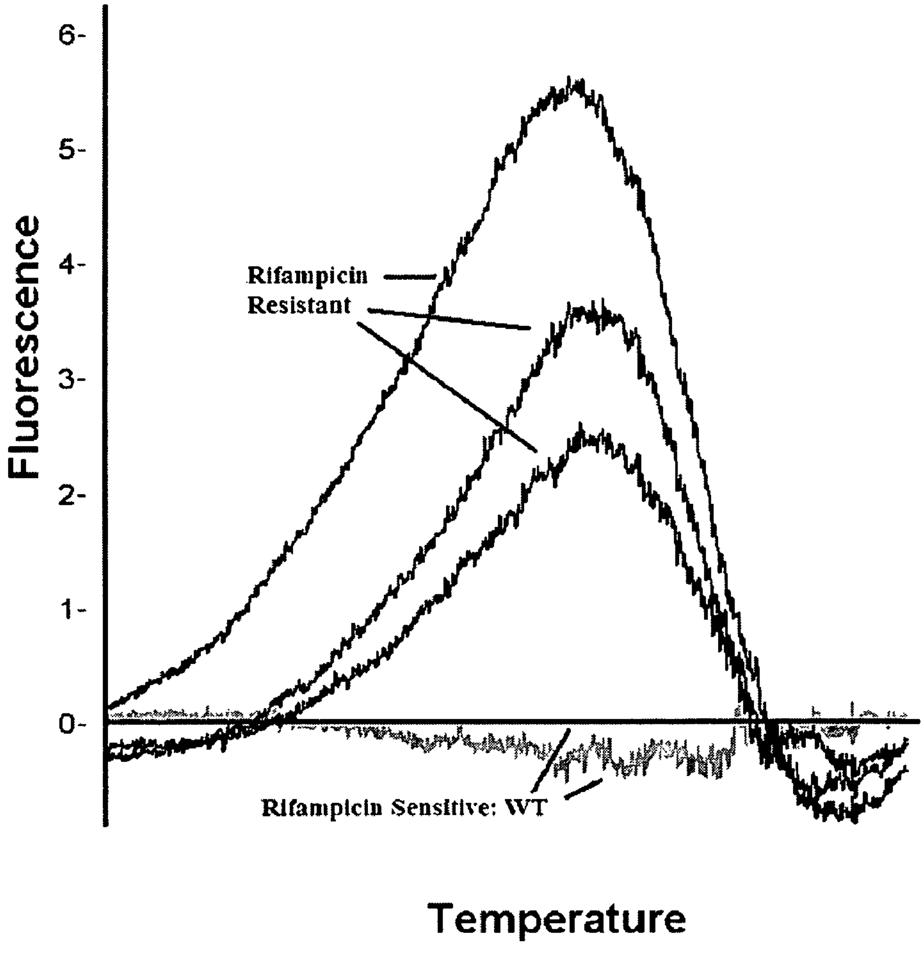
FIG. 10: A. Difference curve analysis of Rifampicin sensitive and resistant samples from *M. tuberculosis*. B. Difference curve analysis of Streptomycin sensitive and resistant samples from *M. tuberculosis.*
Figure 10B:
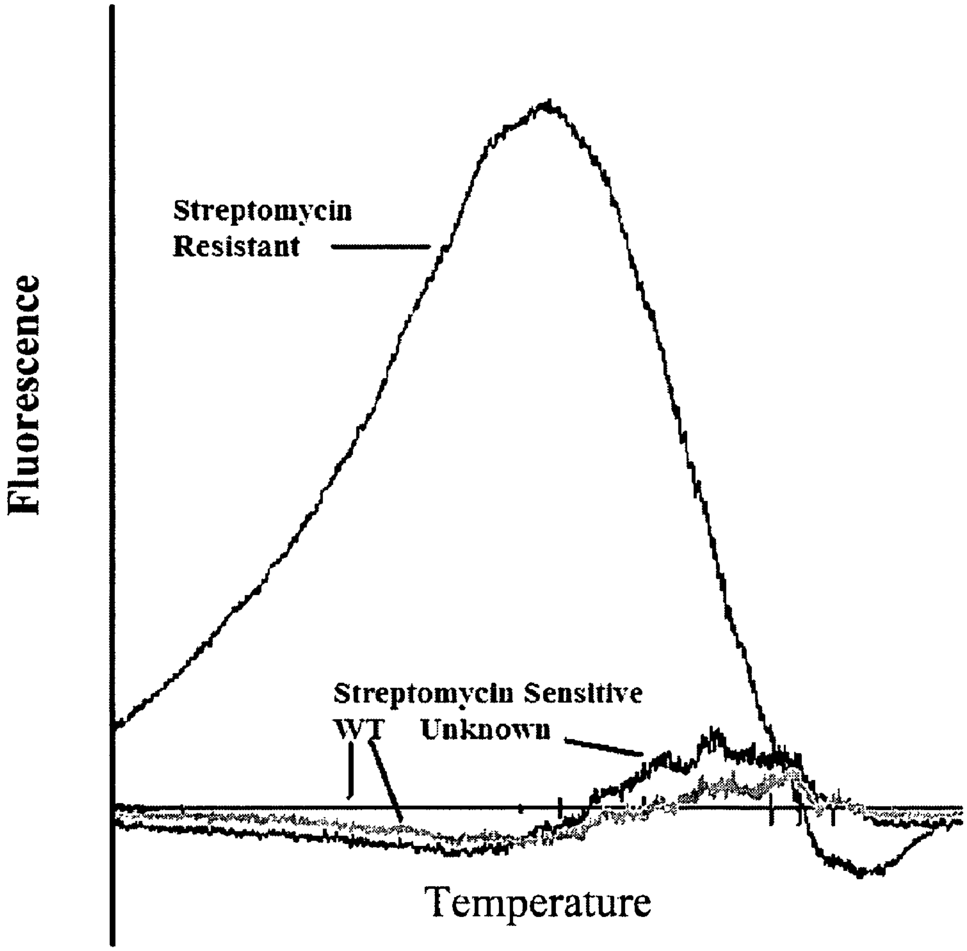

FIG. 10 shows the results of this procedure in curve difference plot formats using primers from Table 2 for the amplification and the corresponding amplicon from Table 3 for the annealing and melting analysis. FIG. 10A shows the analysis of 4 samples for rifampicin resistance or sensitivity along with the control (wt1). FIG. 10B demonstrates the ability to identify Streptomycin resistance in MTb samples. These data demonstrate that this technique can successfully differentiate between regions of DNA that are correlated with Drug sensitivity and those containing polymorphisms correlated with Drug Resistance. In a similar manner, the methods and reagents disclosed herein can be used to assess sensitivity or resistance to all of the first line antibiotics used to treat MTb infections.

Example 3

Determination of Resistance to Anti_Fungal Agents

Fungal and yeast infections are responsible for a large number of diseases in humans. Some brief examples of clinically significant fungi include:

*Malassezia furfur* and *Exophiala wemeckii* (superficial skin)

*Piedraia hortae* and *Trichosporon beigelii* (hair)

*Microsporum* species, (skin and hair)

*Epidermophyton* species (skin and nails)

*Trichophyton* species (skin, hair, and nails)

*Sporothrix schenckii, Cladosporium* species, *Phialophora* species, and

*Fonsecaea* species (subcutaneous/lymphatic tissues—chromoblastomycosis)

*Histoplasma capsulatum, Coccidioides immitis, Fusarium* species, *Penicillium* species (systemic respiratory)

*Blastomyces dermatitidis* (subcutaneous/respiratory)

*Cryptococcus neoformans* (respiratory/CNS)

*Aspergillus* species, *Mucor* species, *Candida* species, and *Rhizopus* species (opportunistic involving various body sites)

Further, fungi are often responsible for common infections such as yeast infections, jock itch, athletes foot, and other dermatological issues. Resistance to antifungal agents will make treatment ineffective, so identification of appropriate drugs is useful.

Figure 11:
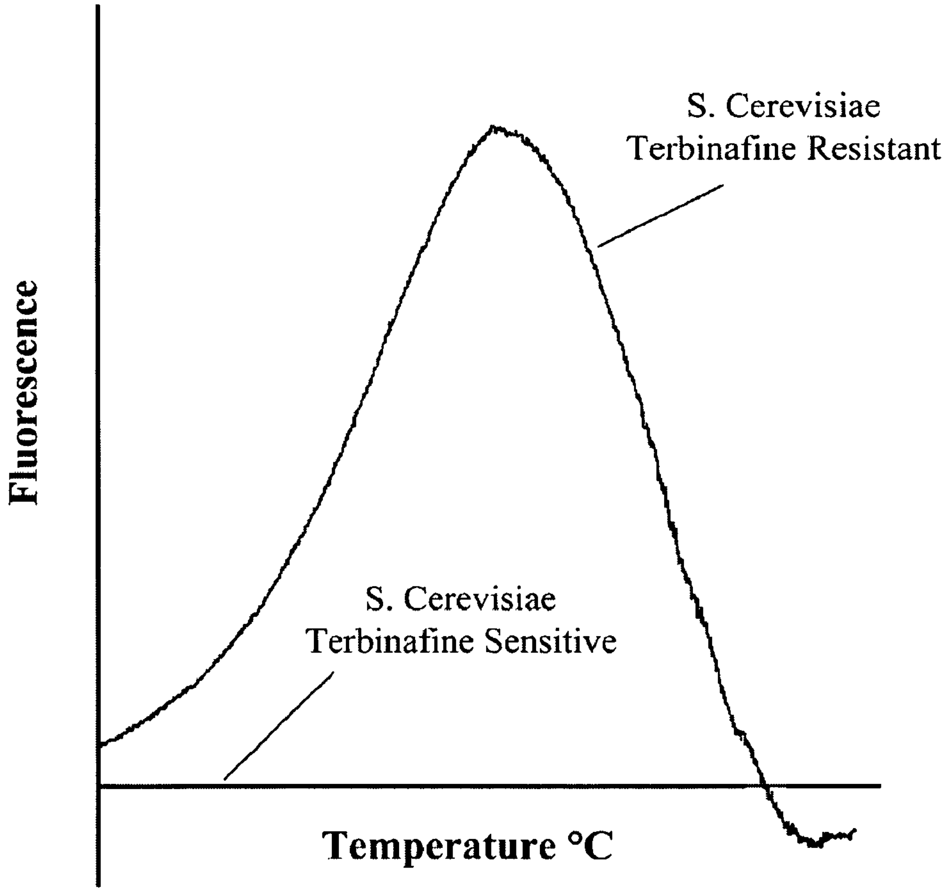
FIG. 11: Difference curve analysis of Terbinafine resistant samples from *S. cerevisiae.*

In order to determine the resistance pattern to terbinafine, a common antifungal agent used for *Saccharomyces* and *Candida* infections, primers from Table 2 were used to amplify the corresponding amplicon from Table 3 using the method presented in Example 2. DNA isolated from wild-type *S. cerevisiae* or a template containing a mutation in the ERG1 gene that confers terbinafine resistance were used as the starting materials, and the results of the melting curve difference analysis are shown in FIG. 11. The mutated sequence is easily discerned from the wild type sequence. Thus, this method can be used to determine drug resistance or sensitivity in fungal infections as well as other pathogenic infections.

Example 4

Figure 12:
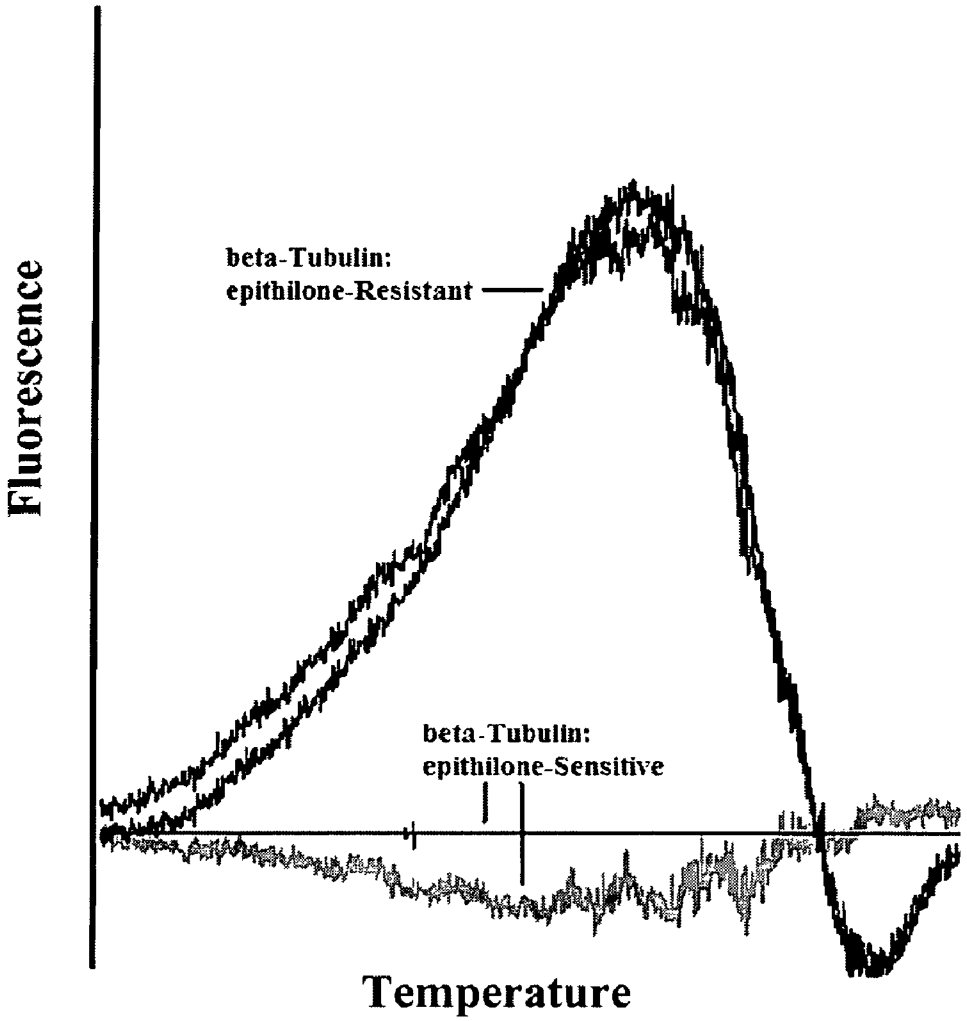
FIG. 12: Difference curve analysis of Taxane sensitive and resistant samples from humans.

Determination of Resistance and Sensitivity Patterns for Human Cancers to Chemotherapeutic Taxanes Taxanes such as taxol, paclitaxel and docetaxel are potent chemotherapeutic agents used to treat wide varieties of cancers. Their mechanism of action is shared by epithilones and work by binding and stabilizing tubulin polymers in cells. The binding sites for these drugs on tubulin has been described (Rao, S., Orr, G. A., Chaudhary, A. G., Kingston, D. G., and Horwitz, S. B. (1995) J. Biol. Chem. 270:20235-20238) and mutations in this region or beta tubulin can cause resistance to taxanes (Table 3). Template DNA was purified by standard means and subjected to the method presented in Example 2, using primers from Table 2 to amplify the corresponding regions in Table 3. Two amplicons with mutations that caused resistance to taxanes (B-tub R282Q and B-tub T247I) were easily distinguishable from two independent reactions with wild type DNA (wt1 and wt2; FIG. 12) using this methodology. Thus, this method could be used to diagnose sensitivity or resistance to chemotherapeutic agents to allow physicians the opportunity to better understand the nature of the cancer and what treatments are likely to be effective or ineffective.

Example 5

Malaria is an infectious disease caused by the parasite called Plasmodia. There are four identified species of this parasite causing human malaria, namely, *Plasmodium vivax, P. falciparum, P. ovale* and *P. malariae.* 300-500 Million people are infected each year. The most common treatment is chloroquine, but resistance to chloroquine has been emerging. Currently, the World Health Organization (WHO) utilizes a method to detect chloroquine resistant mutations that takes 28 days.

Figure 13:
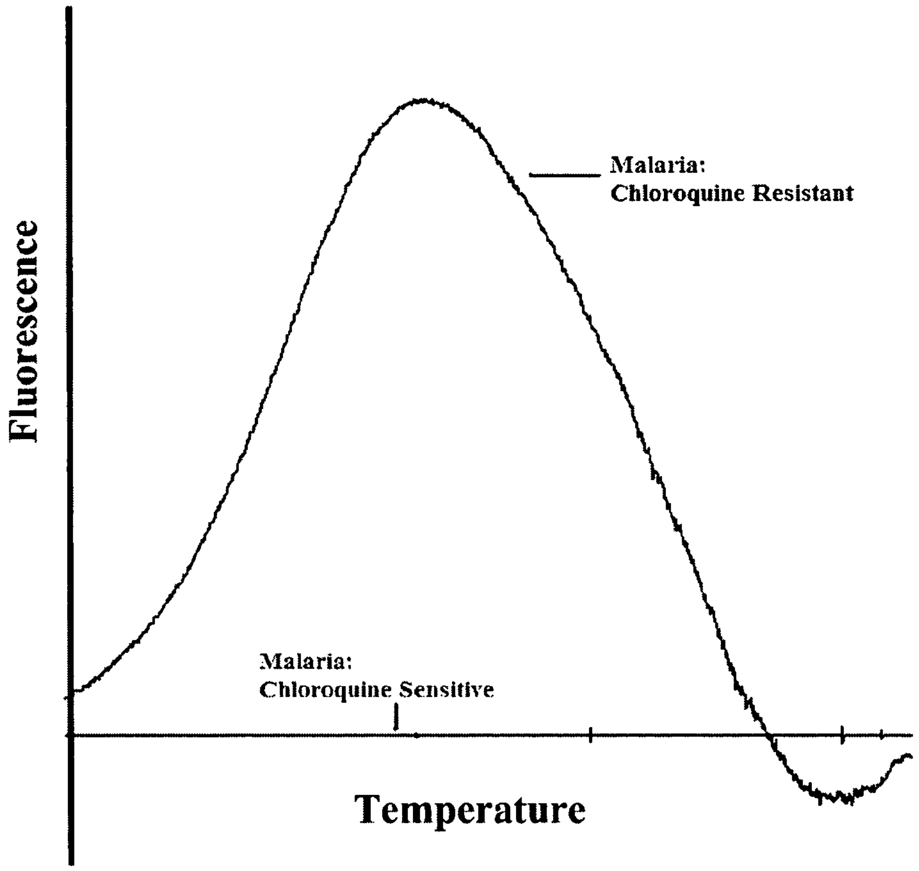
FIG. 13: Difference curve analysis of chloroquine resistant samples from Malaria infections.

The method described in Example 2 was similarly applied to determine its ability to differentiate between chloroquine resistant and chloroquine sensitive DNA. The primers presented in Table 2 were used to amplify the amplicon presented in Table 3. FIG. 13 shows the results of this assay, which demonstrate that the method can readily identify a mutation in this region that results in Chloroquine resistance versus a normal chloroquine sensitive region. Thus, this method could be used to assess the drug sensitivity of parasite infections and allow better treatments. Further, this assay can be performed in less than a day, which is significantly faster than current methods (http://www.malariasite.com/MALARIA/DrugResistance.htm).

Example 6

Determination of Drug Resistance in HIV Infected Individuals

Zidovudine (INN) or azidothymidine (AZT) (also called ZDV) is an antiretroviral drug, the first approved for treatment of HIV. Its mechanism of action is through blockage of the HIV reverse transcriptase, which prevents replication of the viral genetic material. Mutations in regions of the HIV reverse transcriptase have rendered the viruses resistant to these first line drugs.

Figure 14:
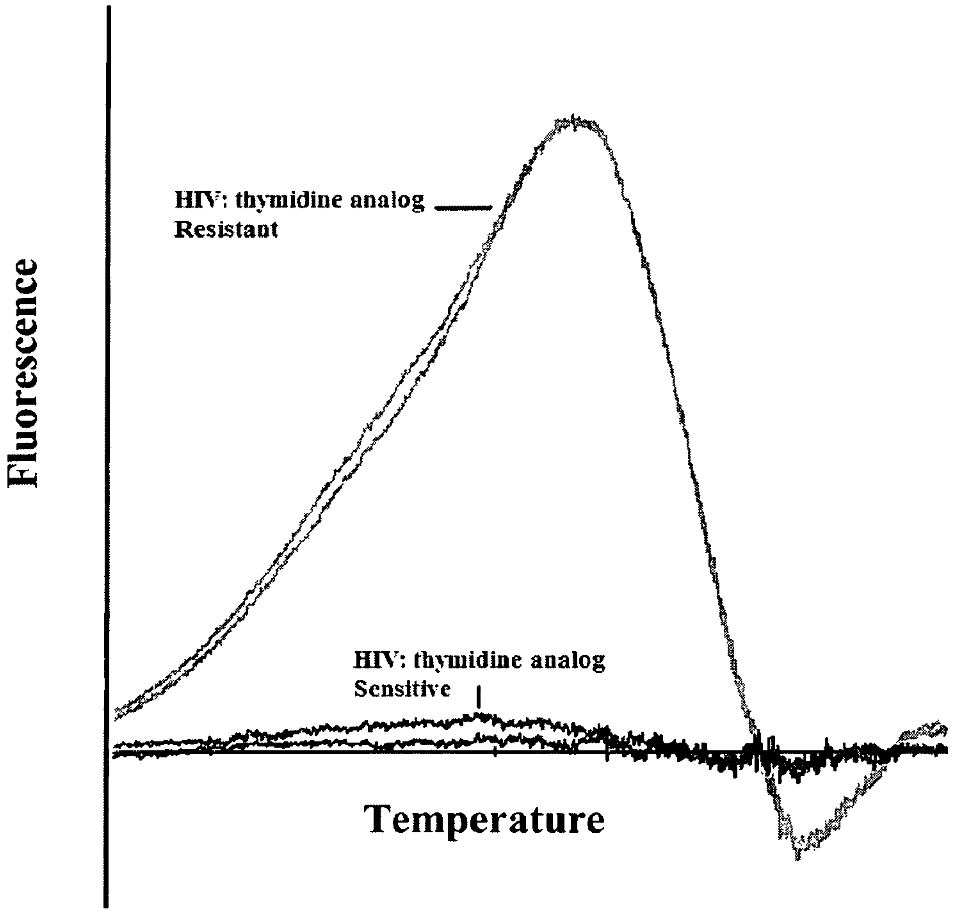
FIG. 14: Difference curve analysis of Zidovudine sensitive and resistant samples from HIV.

FIG. 14 shows the melting curve difference plots of 2 independent runs using the method presented in Example 2 to discriminate between wild type and ZDV-resistant DNA. The primers presented in Table 2 were used to amplify the regions presented in Table 3. This example clearly demonstrates that this method is applicable to determining drug resistance or sensitivity in viral pathogens as well.

Example 7

Determination of Methicillin Resistance in *Staphylococcus aureus* Infections Methicillin-resistant *Staphylococcus aureus* (MRSA) infection is caused by *Staphylococcus aureus* bacteria—often called "*staph*." Decades ago, a strain of *staph* emerged in hospitals that was resistant to the broad-spectrum antibiotics commonly used to treat it. Dubbed methicillin-resistant *Staphylococcus aureus* (MRSA), it was one of the first germs to outwit all but the most powerful drugs. MRSA infection can be fatal. Because of this, it is important to determine whether a given *staph* infection is multi drug resistant so that proper treatment can be administered. Generally, *staph* is collected from tissues or nasal secretions, but can also be isolated from throat samples or open wounds. Standard methods are used to extract the DNA from the clinical sample.

Figure 15:
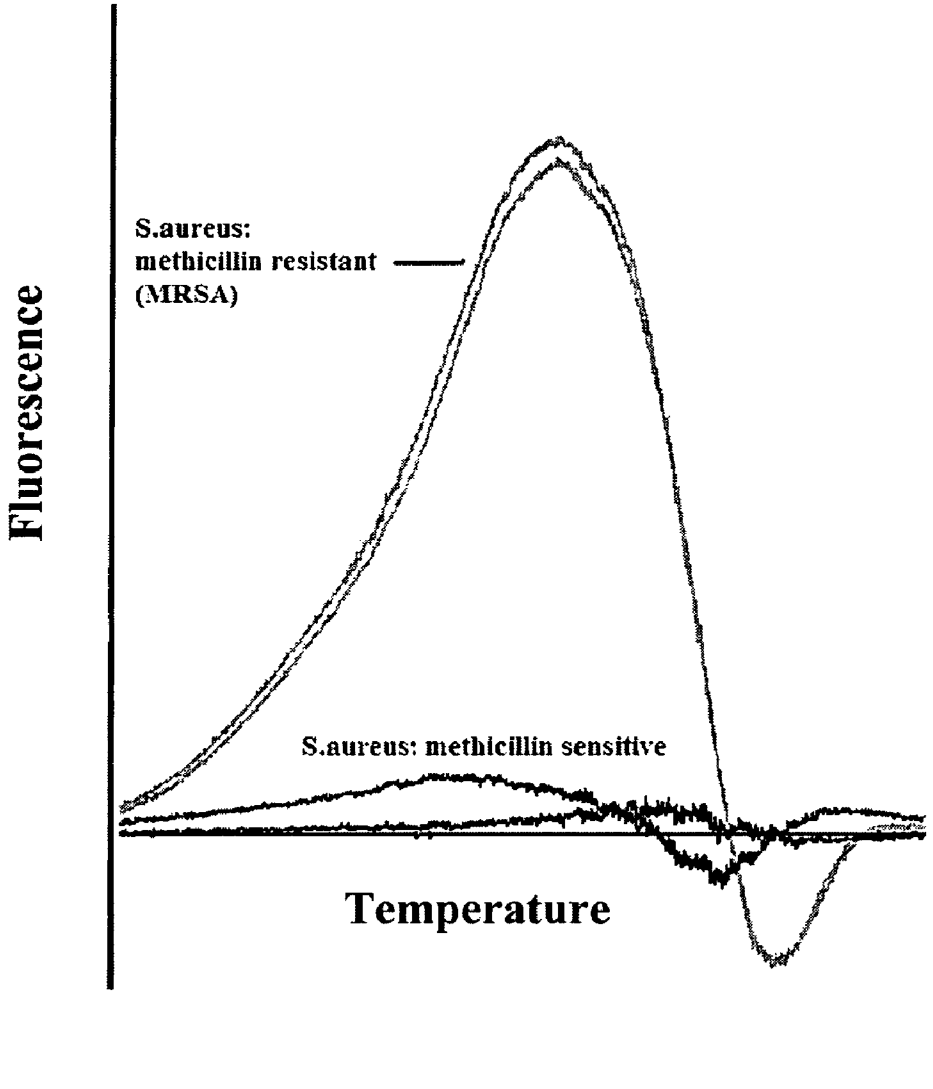
FIG. 15: Difference curve analysis of Vancomycin sensitive and resistant samples from *S. aureus.*

FIG. 15 demonstrates that this method can discriminate between multi drug resistant *staph* infections and normal *staph* infections. Using the primers presented in Table 2 to amplify the region disclosed in Table 3, with the method presented in Example 2, this method could discern between wild type regions of the *staph* DNA and regions with a single point mutation that results in multi drug resistance.

Example 8

Assessment of MTb Infection by Dynamic Flux Amplification

Biological samples suspected of being infected with MTb were assessed for the presence of MTb DNA using dynamic flux amplification. Human samples either positive or negative for MTb infection were treated using the following procedure:

Oligos are the FI-15 MTb primers (Example 1)
The reaction conditions are:
1: 10× FI-15 Buffer (50 mM Tris-HCl, 8.0; 0.25 mg/ml Native (non-acetylated BSA) 2 mM MgCl2; 4% DMSO; 2 mM each dNTPs)
2: Enzyme Gene-Choice HS-TaqPolymerase, although other thermostable DNA polymerases are acceptable.

3: Primers at 0.5 uM Final
4: Thermal cycling: 90–10 sec
Either 74, 76, 78, or 80° C.–10 sec (50+ cycles) (currently done in <1.25 hrs)

Figure 16:
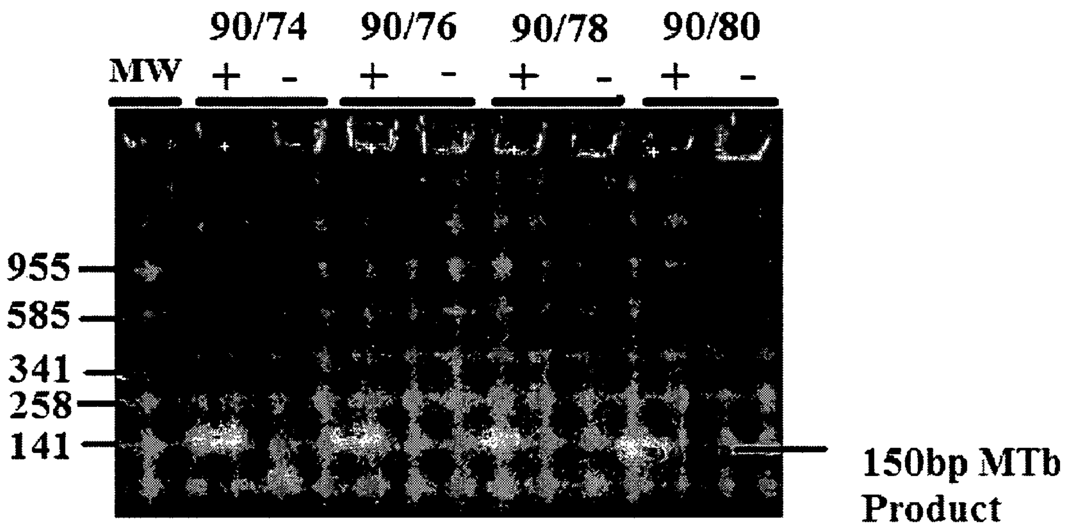
FIG. 16: Agarose gel analysis of *M. tuberculosis* DNA products amplified by dynamic flux amplification simulation.

FIG. 16 shows the results of this reaction at different temperatures for the thermocycling. This experiment was performed in a PCR to simulate the conditions of a heating block in the lab, which when set at 80° C. displayed a temperature cycle of +/−5° C. Each pair of wells performed at a single temperature contains a first reaction that uses a template positive for MTb DNA, and the second a template negative for MTb DNA prepared similarly. The expected 150 bp amplification product appears at all temperature cycling conditions tested only in samples positive for MTb, but is not amplified in control samples. Thus, a field DNA amplification test could be used to assess MTb infections in human samples, using only a standard sample collection and preparation protocol, a heating block to amplify a specific product, and a means to detect said product. This has the potential to allow field diagnosis of MTb infection without the need to send the samples to a designated testing center. Further, it can give a rapid result, requiring only a little over an hour of thermocycling time to amplify the product.

Example 9

Dynamic Flux Amplification to Identify the Presence of *Salmonella typhimurium* in a Test Sample The purpose of this example is to demonstrate that dynamic flux amplification can be used to amplify a specific region of DNA from a biological sample. Thus, instead of using a costly PCR machine, such reactions could take place in a heating block or any device that holds a temperature. If the hold is not highly accurate and maintains the temperature through cycling between heating and off phases, there is a natural flux in the temperature. This is true for heating blocks, heating ovens, and even refrigerators or freezers (although cooling instead of heating).

*Salmonella typhimurium* DNA was isolated from biological samples by standard methods. Samples or control DNA (no template or *E. coli* template) mixtures were prepared and subjected to the following conditions:

```
Forward primer:      caccacgctcaccgatgatgccctgctttg
Tm 77C

Reverser primer:     actgggagccattaaccgcatcggtgctg
Tm 75C
```

Template:

```
actgggagccattaaccgcatcggtgctgtccgcggccagggtgcctgcc
gccagattggtgattttgctggcgcttccgttacggctggcgctgaatgt
gccagaggctgcatcccaaagcagggcatcatcggtgagcgtggtg
Tm = 92C
```

Figure 17:
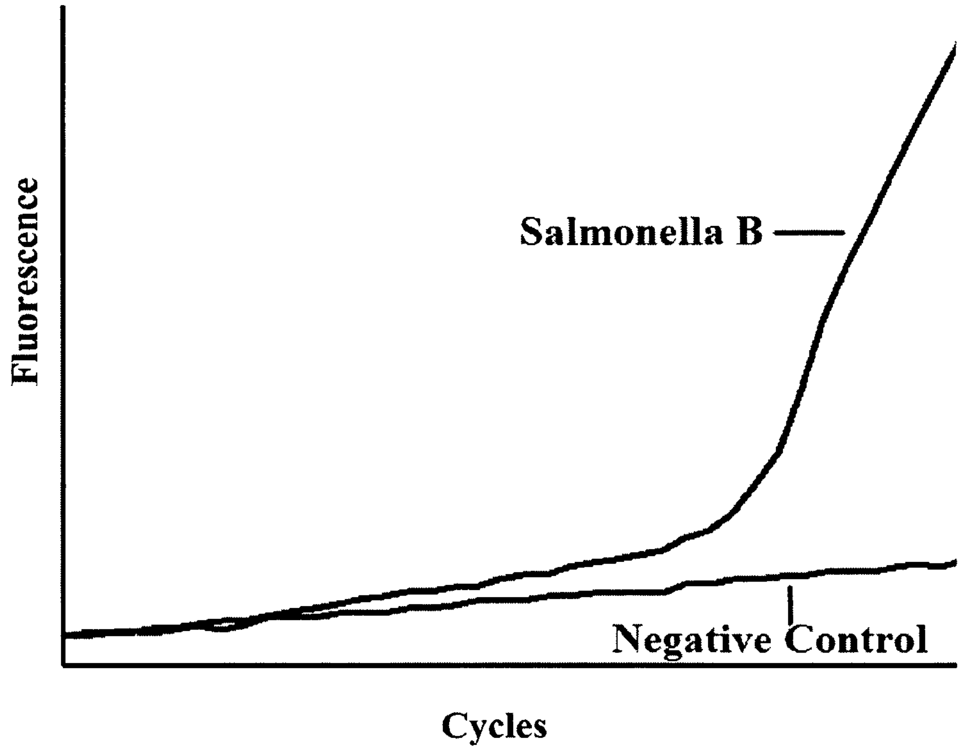
FIG. 17: Real time analysis of *S. tymphimurium* DNA amplification products by dynamic flux amplification.

Reagents:
10× buffer (same as before)
dNTPS (2 mM each)
3 mM MgCl
Primers @ 0.5 uM each
Dye: LC Green (Idaho Technology, Inc Salt Lake City, Utah)
Enzyme: Tfi (exo−) Invitrogen Thermal cycling conditions: initial hold at 79 C for 15 minutes (equivalent to the use of a heating block set to 77-78 degrees Celsius); 90 Cycles: 79 1 min; 76 1 min FIG. 17 shows that a specific product is amplified detectable at cycle 62 and higher. Amplification is only seen in the reaction containing *S. typhimurium* DNA and not in samples containing no DNA or *E. coli* DNA (not shown). Thus, this technology could be used to identify the presence of *S. typhimurium* in a biological sample and indication the presence of bacterial infection if the sample is of non-bacterial origin, such as a human sputum sample or throat swab. Advantageously, the above method can amplify DNA without the use of a thermocycler. Detection of amplified products can be assessed by any traditional methods, including, but not limited to, gel analysis or electrophoresis, UV detection, fluorescent detection, gold detection, capture of hybrids in a ELISA or rapid in vitro diagnostic assay, capture of amplified products by lateral flow, and the like. In some embodiments, primers may be labeled, especially at the 5' end or with internal labels, to allow detection of specific amplified products.

REFERENCES

The following U.S. patents and Pre-Grant Publications are each incorporated herein by specific reference; U.S. Pat. Nos. 4,683,195; 4,965,188; 6,214,587; 6,692,918; 5,219,727; 5,476,774; 5,314,809; 6,040,166; 6,197,563; 6,001,611; 6,617,137; 7,074,600; 6,977,148; 6,740,745; 6,033,881; 7,160,998; 7,081,226; 20070054311; 20050233363; 20050181394; 20040248105; and 20070020672.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:

1. A method for determining if a patient is amenable to treatment with a drug, comprising:

obtaining a biological sample from a patient, the sample containing *Mycobacterium tuberculosis* (MTb);

amplifying a segment of MTb DNA consisting of SEQ ID NO:142, the segment including at least one polymorphism associated with sensitivity of the MTb to an antibiotic drug; and assaying the amplified DNA segment for sequence variations relative to the corresponding sequence of SEQ ID NO:142, wherein a variation in the amplified DNA segment indicates sensitivity of MTb to the antibiotic drug.

2. The method of claim 1, wherein two or more variations in the amplified DNA segment indicates sensitivity of MTb to the antibiotic drug.

3. The method of claim 1, wherein the MTb DNA of SEQ ID NO:142 is amplified by PCR using the corresponding primers of SEQ ID NOS:11 and 12.

4. The method of claim 1, wherein a variation in the amplified DNA segment indicates sensitivity of MTb to rifampicin.

* * * * *

UNITED STATES PATENT AND TRADEMARK OFFICE

CERTIFICATE OF CORRECTION

PATENT NO. : 7,838,235 B2
APPLICATION NO. : 12/058637
DATED : November 23, 2010
INVENTOR(S) : Brian Erich Caplin It is certified that error appears in the above-identified patent and that said Letters Patent is hereby corrected as shown below:

Claim 1, Column 129, line 23, after "containing" delete "Mycobacterium" and insert --Myobacterium--.

Signed and Sealed this
Fifth Day of April, 2011

David J. Kappos
*Director of the United States Patent and Trademark Office*

UNITED STATES PATENT AND TRADEMARK OFFICE

CERTIFICATE OF CORRECTION

PATENT NO. : 7,838,235 B2
APPLICATION NO. : 12/058637
DATED : November 23, 2010
INVENTOR(S) : Brian Erich Caplin It is certified that error appears in the above-identified patent and that said Letters Patent is hereby corrected as shown below:

On the Cover Page, item [57], Abstract, line 6, after “resistant” delete “Myobacterium” and insert --Mycobacterium--.

Column 2, line 65, after “contains” delete “Myobacterium” and insert --Mycobacterium--.

Column 3, line 43, after “with” delete “Myobacterium” and insert --Mycobacterium--.

Claim 1, Column 129, line 23, after “containing” delete “Myobacterium” and insert --Mycobacterium --.

Signed and Sealed this
Fifth Day of July, 2011

David J. Kappos
*Director of the United States Patent and Trademark Office*